US012761217B2

(12) United States Patent
Krug

(10) Patent No.: US 12,761,217 B2
(45) **Date of Patent: *Oct. 13, 2026**

(54) CELL PROCESSING USING MAGNETIC PARTICLES

(71) Applicant: Inguran, LLC, Navasota, TX (US)

(72) Inventor: Kristie Krug, Upper Arlington, OH (US)

(73) Assignee: Inguran, LLC, Navasota, TX (US)

( * ) Notice: Subject to any disclaimer, the term of this patent is extended or adjusted under 35 U.S.C. 154(b) by 802 days.

This patent is subject to a terminal disclaimer.

(21) Appl. No.: 18/120,295

(22) Filed: Mar. 10, 2023

(65) Prior Publication Data

US 2023/0228750 A1 Jul. 20, 2023

Related U.S. Application Data

(63) Continuation of application No. 16/537,402, filed on Aug. 9, 2019, now Pat. No. 11,630,108, which is a (Continued)

(51) Int. Cl.
*G01N 33/543* (2006.01)
*B03C 1/01* (2006.01)
(Continued)

(52) U.S. Cl.
CPC ........... *G01N 33/5434* (2013.01); *B03C 1/01* (2013.01); *B03C 1/288* (2013.01); *C12N 13/00* (2013.01);
(Continued)

(58) Field of Classification Search
CPC ......... G01N 33/56966; G01N 33/5375; G01N 33/54333; G01N 33/5434;
(Continued)

(56) References Cited

U.S. PATENT DOCUMENTS

| | | |
|---|---|---|
| 3,917,538 A | 11/1975 | Rosensweig |
| 3,976,197 A | 8/1976 | Bhattacharya |

(Continued)

FOREIGN PATENT DOCUMENTS

| | | |
|---|---|---|
| EP | 0113452 A2 | 7/1984 |
| FR | 2811682 A3 | 1/2002 |

(Continued)

OTHER PUBLICATIONS

Reutelingsperger et al. Annexin V, the regulator of phosphatidylserine-catalyzed inflammation and coagulation during apoptosis. CMLS: Cell Mol. Life Sci. 53: 527-532 (1997).*

(Continued)

*Primary Examiner* — Gailene Gabel
(74) *Attorney, Agent, or Firm* — Ryan Christensen; Hashim Rahman

(57) ABSTRACT

The present invention relates to compositions comprising magnetic particles, the methods of using these compositions in processing animal sperm, the resulting sperm and embryo products, and the methods of use of these compositions to increase the efficiency, efficacy and/or speed of cell processing and artificial insemination techniques.

7 Claims, 36 Drawing Sheets

Related U.S. Application Data continuation of application No. 14/960,096, filed on Dec. 4, 2015, now Pat. No. 10,379,026, and a continuation-in-part of application No. 13/974,139, filed on Aug. 23, 2013, now Pat. No. 9,804,153.

(60) Provisional application No. 62/088,425, filed on Dec. 5, 2014, provisional application No. 61/694,756, filed on Aug. 29, 2012.

(51) Int. Cl.

| | |
|---|---|
| ***B03C 1/28*** | (2006.01) |
| ***C12N 13/00*** | (2006.01) |
| ***G01N 15/10*** | (2006.01) |
| ***G01N 33/537*** | (2006.01) |
| ***G01N 33/569*** | (2006.01) |

(52) U.S. Cl.

CPC ......... *G01N 15/10* (2013.01); *G01N 33/5375* (2013.01); *G01N 33/54333* (2013.01); *G01N 33/54346* (2013.01); *G01N 33/5438* (2013.01); *G01N 33/56966* (2013.01); *B03C 2201/18* (2013.01); *B03C 2201/26* (2013.01); *G01N 2015/1006* (2013.01); *G01N 2015/1028* (2024.01)

(58) Field of Classification Search

CPC ......... G01N 33/54346; G01N 33/5438; G01N 2015/1028; G01N 2015/1006

See application file for complete search history.

(56) References Cited

U.S. PATENT DOCUMENTS

| | | | |
|---|---|---|---|
| 4,083,957 | A | 4/1978 | Lang |
| 4,092,229 | A | 5/1978 | Bhattacharya |
| 4,276,139 | A | 6/1981 | Lawson |
| 4,554,088 | A | 11/1985 | Whitehead et al. |
| 4,698,302 | A | 10/1987 | Whitehead et al. |
| 4,927,749 | A | 5/1990 | Dorn |
| 5,466,574 | A | 11/1995 | Liberti et al. |
| 5,466,587 | A | 11/1995 | Fitzpatrick-McElligott et al. |
| 5,597,531 | A | 1/1997 | Liberti et al. |
| 6,153,373 | A | 11/2000 | Benjamin et al. |
| 7,169,548 | B2 | 1/2007 | Maxwell et al. |
| 7,699,979 | B2 | 4/2010 | Li et al. |
| 7,754,444 | B2 | 7/2010 | Xu et al. |
| 7,758,811 | B2 | 7/2010 | Durack |
| 7,776,580 | B2 | 8/2010 | Zhang et al. |
| 7,829,350 | B2 | 11/2010 | Josephson et al. |
| 9,157,063 | B2 * | 10/2015 | Prien ...................... C12M 47/04 |
| 9,804,153 | B2 * | 10/2017 | Krug ................ G01N 33/54333 |
| 10,324,086 | B2 * | 6/2019 | Krug ...................... C12N 13/00 |
| 10,379,026 | B2 * | 8/2019 | Krug ......................... B03C 1/01 |
| 11,531,026 | B2 * | 12/2022 | Krug ......................... B03C 1/02 |
| 11,630,108 | B2 * | 4/2023 | Krug ...................... G01N 15/10 435/7.1 |
| 11,662,344 | B2 * | 5/2023 | Krug ................ G01N 33/54333 435/173.9 |
| 2002/0034537 | A1 | 3/2002 | Schulze et al. |
| 2002/0182751 | A1 | 12/2002 | Herr et al. |
| 2004/0142384 | A1 | 7/2004 | Cohen et al. |
| 2005/0025971 | A1 | 2/2005 | Cho et al. |
| 2006/0141512 | A1 | 6/2006 | Sinha et al. |
| 2008/0044811 | A1 | 2/2008 | Haugland |
| 2008/0206771 | A1 | 8/2008 | Liu |
| 2008/0318250 | A1 | 12/2008 | Gilmer et al. |
| 2009/0023205 | A1 | 1/2009 | Dennig et al. |
| 2009/0042255 | A1 | 2/2009 | Liu |
| 2009/0101507 | A1 | 4/2009 | Aitken et al. |
| 2009/0208977 | A1 | 8/2009 | Hudson et al. |
| 2009/0306461 | A1 | 12/2009 | Oksenberg et al. |
| 2010/0081130 | A1 | 4/2010 | Lee et al. |
| 2010/0129808 | A1 | 5/2010 | Mirkin et al. |
| 2010/0200405 | A1 | 8/2010 | Lenz |
| 2011/0086336 | A1 | 4/2011 | Herickhoff et al. |
| 2011/0201047 | A1 | 8/2011 | Paduch |
| 2011/0256581 | A1 | 10/2011 | Gregory et al. |
| 2012/0100546 | A1 | 4/2012 | Lowery, Jr. et al. |
| 2012/0270204 | A1 * | 10/2012 | Fox ...................... C12N 5/0612 977/773 |
| 2019/0293638 | A1 | 9/2019 | Krug |
| 2020/0033331 | A1 | 1/2020 | Krug |

FOREIGN PATENT DOCUMENTS

| | | | |
|---|---|---|---|
| FR | 2827799 | A1 | 1/2003 |
| JP | 53056381 | A | 5/1978 |
| JP | 601564 | A | 1/1985 |
| JP | 2004073112 | A | 3/2004 |
| JP | 2012037259 | A | 2/2012 |
| WO | 8806632 | A1 | 9/1988 |
| WO | 9007380 | A2 | 7/1990 |
| WO | 9741224 | A1 | 11/1997 |
| WO | 9958977 | A1 | 11/1999 |
| WO | 2004029221 | A1 | 4/2004 |
| WO | 2005054808 | A2 | 6/2005 |
| WO | 2008095155 | A2 | 8/2008 |
| WO | 2010073014 | A1 | 7/2010 |

OTHER PUBLICATIONS

International Search Report for PCT/US13/56526 (Feb. 7, 2014).

Written Opinion for PCT/US13/56526 (Feb. 7, 2014).

Shannon, P. "Contribution of Seminal Plasma, Sperm Numbers and Gas Phase to Dilution Effects of Bovine Spermatozoa." J. Dairy Sci., 48: 1357 (1965).

Shannon, P. et al. "Toxic Effect and Action of Dead Sperm on Diluted Bovine Semen." J. Dairy Sci., 55: 615-620 (1972).

Lindemann, C. B. et al. "A Comparative Study of the Effects of Freezing and Frozen Storage on Intact and Demembranated Bull Spermatozoa." Cryobiology, 19: 20-28 (1982).

Saacke, R. G. et al. "Semen Quality Tests and Their Relationship to Fertility." Proc. 4th National Association of Animal Breeders, Tech. Conf. Artificial Insemination and Reproduction, Apr. 18-20, 1972, Madison, WI, National Association of Animal Breeders, Columbia, MO, pp. 22-27.

G.W. Salisbury, G. W. et al. "Physiology of Reproduction and Artificial Insemination of Cattle." second edition, Copyright 1961 & 1978. ISBN 0-7167-0025-5.

Schenk, J. L. et al. "Cryopreservation of Flow-Sorted Bovine Spermatozoa.", Theriogenology 52:1375-1391, 1999.

Parish, J. J. et al. "Capacitation of bovine sperm by Heparin", Biology of Reproduction 38:1171-1180, 1988.

Anzar, M. et al. "Filtration of Bovine Semen. I. Development of a Sephadex Ion-Exchange Filter." Anim. Reprod. Sci. 1993; 31:187-195.

Avery, B. et al. "Impact of Percoll on Bovine Spermatozoa Used for in Vitro Insemination." Theriogenology 1995; 44:871-788.

Correa, J. R. et al. "Preparation and Recovery of Frozen—Thawed Bovine Spermatozoa Via Various Sperm Selection Techniques Employed in Assisted Reproductive Technologies." Theriogenology 1996; 46:1225-1232.

Garner, D. L.et al. "Dual DNA Staining Assessment of Bovine Sperm Viability Using SYBR-14 and Propidium Iodide." J Andral 1994; 15:620-629.

Graham, E. F. et al. "The Effect of Whole Ejaculate Filtration on the Morphology and Fertility of Bovine Semen." J. Dairy Sci. 1990; 73:91-97.

Johnson, L. A. et al. "Sex Preselection in Rabbits: Live births from X and Y Bearing Sperm Separated by DNA and Cell Sorting." Biol Reprod 1989; 41:199-203.

Luderer, A. A. et al. "Separation of Bovine Spermatozoa by Density on Water Insoluble Newtonian Gels and Their Use or Insemination." Biol Reprod 1982; 26 (5):813-824.

Pasteur, X. et al. "Identification of Two Human Sperm Populations Using Flow and Image Cytometer." Molecular Reproduction and Development 1994; 38:303-309.

(56) References Cited

OTHER PUBLICATIONS

BcMagTm Carboxy-terminated Magnetic Beads. Product Manual. Bioclone, Inc. 2010 http://www.bioclone.us/files/BcMag_Carboxy-Terminated_Magnetic_Beads2.pdf.
BcMagTm Carboxy-terminated Magnetic Beads. Bioclone, Inc. 2010 http://www.bioclone.us/carboxyl-terminated-magnetic-beads-particle-resin-matrix.html.
BcMagTm SAX Magnetic Beads. Bioclone, Inc. 2010. http://www.bioclone.us/Strong-Anion-Exchange-magnetic-beads-particle-resin-matrix.html.
BcMagTm SAX Magnetic Beads. Product Manual. Bioclone, Inc. 2010 http://www.bioclone.us/files/BcMag_SAX_Magnetic_Beads.pdf.
Dynabeads SAX. Invitrogen Dynal Invitrogen Bead Separation; 2007. http://tools.thermofisher.com/content/sfs/manuals/105%2015D_16D_Dynabeads_SAX_rev002.pdf.
Dynabeads WCX. Invitrogen Dynal Invitrogen Bead Separation; 2008. http://tools.thermofisher.com/content/sfs/manuals/105%2011D12D%20%28001%29.pdf.
Dynabeads SCX. Invitrogen Dynal Invitrogen Bead Separation; 2007. http://tools.thermofishercom/content/sfs/manuals/105%2013D_14D%20Dynabeads%20SCX%28rev002%29.pdf.
M-Beads—Magnetic Silica Beads. MoBiTec; Magnetic Silica Beads. 2010.
Qiagen Purification Technologies. Qiagen anion-exchange, silica gel membrane, and magnetic particle technologies. 2012.
Propidium Iodide Staining Solution Technical Data Sheet. BD Pharmingen. BD Biosciences. 2006.
Dynabeads M-270 Carboxylic Acid. Invitrogen, 2012. https://tools.thermofishercom/content/sfs/manuals/dynabeads_m270carboxylicacid_man.pdf.
Australian Examination Report dated Oct. 27, 2015 for Appl. No. 2013309137.
Said et al. "Utility of Magnetic Cell Separation as a Molecular Sperm Preparation Technique." J Andral. 2008 ; 29(2):134-142.
Hofmo, Peer Ola "Sperm Sorting and Low-Dose Insemination in the Pig—An Update" Acta Veterinaria Scandinavica 2006, 48(Suppl 1):S11.
Clemente, Henry. "Does Mammalian Sperm have a Charge." ResearchGate. 2013. http://www.researchgate.net/post/Does_mammalian_sperm_have_a_charge.
Peter et al. "Fractionation of Bovine Spermatozoa for. Sex Selection: A Rapid Immunomagnetic Technique to Remove Spermatozoa That Contain the H-Y Antigen." Theriogenology 40:1177-1185, 1993.
EP Extended Search Report dated Feb. 17, 2016 for Appl. No. 13832402.5.
Zhaogang "Highly Magnetizable Superparamagnetic Iron Oxide Nanoparticles Embedded Mesoporous Silica Spheres and Their Application for Efficient Recovery of DNA from Agarose Gel" Journal of Materials Chemistry, vol. 19, No. 13, Jan. 1, 2009, p. 1811.
Bruce I J et al: "Synthesis, Characterisation and Application of Silicamagnetite Nanocomposites", Journal of Magnetism and Magnetic Materials, vol. 284, Dec. 1, 2004, pp. 145-160.
CA Examination Report dated Jan. 21, 2016 for Appl. No. 2,883,328.
JP Examination Report dated Feb. 29, 2016 for Appl. No. 2015-529882.
Van Wienen, Marjet et al. "Single Layer Centrifugation with Androcoll-P Can be Scaled-Up to Process Larger Volumes of Boar Semen." ISRN Veterinary Science. vol. 2011, Article ID 548385. pp. 8.
AU Examination Report dated Apr. 8, 2016 for Appl. No. 2013309137.
RU Examination Report dated May 10, 2016 for Appl. No. 2015111211.
AU Examination Report dated Jul. 8, 2016 for Appl. No. 2013309137.
RU Examination Report dated Oct. 4, 2016 for Appl. No. 2015111211.
JP Examination Report dated Oct. 4, 2016 for Appl. No. 2015-529882.
NZ Examination Report dated Nov. 17, 2016 for Appl. No. 705665.
Chan et al. A simple zeta method for sperm selection based on membrane charge. Fertility and Sterility. 85 (2):481-486 (Feb. 2006).
Khajavi et al. Can Zeta sperm selection method, recover sperm with higher DNA integrity compare to density gradient centrifugation. Iranian Journal of Reproductive Medicine 7 (2): 73-77 (2009).
CA Examination Report dated Nov. 25, 2016 for Appl. No. 2,883,328.
EP Examination Report dated Feb. 2, 2017 for Appl. No. 13832402.5.
New Zealand Notice of Acceptance issued on Aug. 21, 2017 for NZ Appl. No. 705665.
Said T., et al., "Utility of magnetic cell separation as a molecular sperm preparation technique," J Androl. 29:134-142 (2008).
Reutelingsperger &van Heerde, "Annexin V, the regulator of phosphatidylserine-catalyzed inflammation and coagulation during apoptosis," Cell Mol. Life Sci. 53(6):527-532 (1997).
Said, T., et al., "Effects of advanced selection methods on sperm quality and ART outcome: a systematic review," Human Reproduction Update 17:719-733 (2011) (Advance Access Publication Aug. 25, 2011).
European Intention to Grant Issued on Aug. 30, 2017 in related EP Appl. No. 13832402.5.
Australian Examination Report issued on Nov. 6, 2017 in related AU Appl. No. 2016247202.
Canadian Examination Report issued on Nov. 20, 2017 in related CA Appl. No. 2883328.
Notice of Allowance issued on Aug. 16, 2017 in related U.S. Appl. No. 13/974,139.
Office Action issued on Sep. 15, 2015 in related U.S. Appl. No. 13/974,139.
Final Office Action issued on Mar. 31, 2016 in related U.S. Appl. No. 13/974,139.
Office Action issued on Sep. 8, 2016 in related U.S. Appl. No. 13/974,139.
Final Office Action issued on Jan. 1, 2017 in related U.S. Appl. No. 13/974,139.
Office Action issued on May 3, 2017 in related U.S. Appl. No. 13/974,139.
US Notice of Allowance issued on Aug. 16, 2017 for U.S. Appl. No. 13/974,139.
Australian Examination Report Issued on May 15, 2018 in related AU Appl. No. 2016247202.
US Office Action Issued on Jun. 8, 2018 in related U.S. Appl. No. 14/960,096.
Extended European Search Report Issued on Feb. 19, 2017 in related EP Appl. No. 17208185.3.
Office Action issued on Feb. 8, 2017 in related U.S. Appl. No. 14/960,096.
Said et al. "Effects of advanced selection methods on sperm quality and ART outcome: a systematic review." Human Reproduction Update, vol. 17, No. 6, Nov. 2011, pp. 719-733.
European Decision to Grant Issued on Jan. 25, 2017 in related EP Appl. No. 13832402.5.
US Office Action Issued on Nov. 4, 2018 in related U.S. Appl. No. 14/960,096.
Indian Examination Report Issued on Dec. 6, 2018 in related IN Appl. No. 538/KOLNP/2015.
EPO Extended Search Report Issued on Dec. 12, 2018 in related EP Appl. No. 15866159.5.
Grunewald et al: "Enrichment of non-apoptotic human spermatozoa after cryopreservation by immunomagnetic cell sorting", Cell and Tissue Banking, 2(3), pp. 127-133. (2001).
Glander et al: "Deterioration of spermatozoal plasma membrane is associated with an increase of sperm lyso-phosphatidylcholines", Andrologia, 34(6), pp. 360-366. (2002).
Extended European Search Report Issued on Sep. 10, 2019 in related EP Appl. No. 19180225.5.
New Zealand Examination report Issued on Sep. 6, 2019 in related NZ Appl. No. 734393.
Berg et al. "The relationship between pH and zeta potential of ~ 30 nm metal oxide nanoparticle suspensions relevant to in vitro toxicological evaluations." Nanotoxicology, Dec. 2009; 3(4): 276-283.

(56) References Cited

OTHER PUBLICATIONS

US Office Action issued on Jun. 9, 2022 in related U.S. Appl. No. 16/443,281.
Australian Examination report issued on May 28, 2020 in related AU Appl. No. 2015357516.
Australian Examination report issued on Jun. 10, 2020 in related AU Appl. No. 2019246835.
Brazil examination report issued on Jul. 9, 2020 in related BR Appl. No. BR112015004374-7.
European examination report issued on Jul. 6, 2020 in related EP Appl. No. 19180225.5.
Third-Party Preissuance Submission Under 37 C.F.R. 1.290 issued Feb. 3, 2022 in related U.S. Appl. No. 16/443,281.
Reutelingsperger et al. "Annexin V, the regulator of phosphatidylserine-catalyzed inflammation and coagulation during apoptosis", CMLS, Cell mol. life sci, 53 (1997) 527-532.

* cited by examiner

| | Zeta Potential (nanoComposix) | | | | ICP (Elemental Analysis) | |
|---|---|---|---|---|---|---|
| | Result Quality | Zeta Potential (mV) | CV | Quality factor | ICP mg/mL | YIELD |
| Lot 1 | Good | -26.8 | 23.0% | 3.83 | 7.1 | 82.8% |
| Lot 2A | Good | -35.4 | 13.2% | 5.75 | 14 | 94.0% |
| Lot 2B | Good | -29.6 | 14.0% | 3.27 | 16 | 90.0% |
| Lot 3 | Good | -28.6 | 16.0% | 3.57 | 36 | 87.5% |

Fig. 2

| | Sort rate x | % Oriented | % Dead | %PVR |
|---|---|---|---|---|
| CONTROL | 7522 | 70.10 | 7.67 | 41.84 |
| Lot 1 | 8192 | 74.06 | 2.82 | 44.16 |
| Lot 2A | 8047 | 73.64 | 3.68 | 46.11 |
| Lot 2B | 8310 | 74.53 | 3.02 | 43.06 |
| Lot 3 | 8199 | 74.25 | 3.41 | 42.10 |

Fig. 3

| Average 5 Bulls | Concentration | % Dead | % Dead Removed | % Sperm Removed | % "Other" Sperm Removed | Ratio (Other Sperm removed for every dead) | Relative % of DEAD Sperm Removed | Relative % of Other Sperm Removed |
|---|---|---|---|---|---|---|---|---|
| CONTROL | 115.3 | 7.7% | | | | | | |
| Lot 1 | 99.0 | 2.8% | 4.8% | 14.2% | 10.4% | 1.73 | 88.4% | 9.7% |
| Lot 2A | 97.8 | 3.7% | 4.0% | 16.2% | 12.0% | 2.34 | 56.3% | 11.5% |
| Lot 2B | 99.6 | 3.2% | 4.7% | 13.7% | 10.0% | 1.70 | 86.1% | 9.3% |
| Lot 3 | 103.7 | 3.4% | 4.3% | 10.1% | 6.1% | 1.18 | 80.1% | 8.9% |

Fig. 4

| | 0 Hour | | | | | 3 Hour | | | | |
|---|---|---|---|---|---|---|---|---|---|---|
| | Visual | Analytical sorter | | IVOS II | | Visual | Analytical sorter | | IVOS II | |
| | Motility | Viable | PIA | MOTILE | PROGRESSIVE | Motility | Viable | PIA | MOTILE | PROGRESSIVE |
| CONTROL | 49 | 27.91 | 43.22 | 23.24 | 16.22 | 21 | 15.14 | 25.27 | 9.14 | 2.20 |
| LOT1 | 50 | 29.23 | 47.32 | 22.18 | 14.26 | 25 | 18.79 | 31.09 | 11.22 | 2.96 |
| LOT 2A | 55 | 30.16 | 47.94 | 26.08 | 17.32 | 27 | 19.31 | 30.07 | 11.70 | 4.24 |
| LOT 2B | 46 | 25.96 | 42.51 | 20.58 | 12.88 | 24 | 19.33 | 29.76 | 9.53 | 2.05 |
| LOT 3 | 49 | 30.22 | 49.04 | 21.78 | 13.20 | 24 | 20.44 | 31.24 | 16.70 | 5.08 |

| | Sort rate x | % Oriented | % Dead | %PVR |
|---|---|---|---|---|
| AV CONTROL | 7200 | 68.63 | 9.22 | 41.1 |
| AV REGULAR | 8150 | 72.90 | 4.10 | 41.4 |
| AV SONICATED | 8161 | 75.12 | 1.93 | 39.8 |

Fig. 6

| Average 5 Bulls | Concentration | % Dead | % Dead Removed | % Sperm Removed | % "Other" Sperm Removed | Ratio (Other Sperm removed for every dead) | Relative % of DEAD Sperm Removed | Relative % of Other Sperm Removed |
|---|---|---|---|---|---|---|---|---|
| Control | 119.18 | 9.2% | | | | | | |
| Regular | 102.422 | 4.1% | 5.1% | 14.8% | 9.8% | 1.93 | 61.8% | 8.1% |
| Sonicated | 98.696 | 1.9% | 7.3% | 17.3% | 11.6% | 1.38 | 82.5% | 10.8% |

Fig. 7

Post-Thaw QC – Average 5 Bulls

| | 0 Hour | | | 3 Hour | | |
|---|---|---|---|---|---|---|
| | Visual | Analytical Sorter | | Visual | Analytical Sorter | |
| | Motility | Viable | PIA | Motility | Viable | PIA |
| CONTROL | 64.2 | 44.442 | 69.378 | 50 | 39.378 | 54.772 |
| REGULAR | 63.2 | 44.714 | 70.168 | 50 | 35.424 | 52.58 |
| SONICATED | 65.6 | 46.53 | 71.292 | 51.2 | 36.024 | 53.074 |

| | | Concentration | PV | %Oriented | % Dead | Sort Speed |
|---|---|---|---|---|---|---|
| AVERAGE | CONTROL | 179.4 | 1.51 | 45% | 31% | 2600 |
| | TREATED | 107 | 1.29 | 59% | 12% | 3167 |

| % Dead Removed | Sperm Removed (Million) | % Sperm Removed | Number of sperm unaccounted | % Other sperm removed |
|---|---|---|---|---|
| 19% | 72.4 | 40% | 29.10 | 16% |

| | Bull 1 | Bull 2 | Bull 3 | Bull 4 | Bull 5 |
|---|---|---|---|---|---|
| Control | 42.5 | 51 | 13 | 5 | 0 |
| Treated | 42.5 | 35 | 11.5 | 10 | 5 |

| AVERAGE (n=8) | | Concentration after staining | PV | %Oriented | % Dead | Sort Speed |
|---|---|---|---|---|---|---|
| | CONTROL | 148 | 1.61 | 54% | 21% | 4099 |
| | TREATED | 100 | 1.47 | 61% | 11% | 4500 |

Post Thaw Motilities VISUAL (average of 2 straws)

| Bull | Part | 0 Hour | 3 Hour |
|---|---|---|---|
| 1 | C | 63.5 | 55 |
| 1 | T | 67.5 | 60 |
| 2 | C | 65 | 60 |
| 2 | T | 62.5 | 60 |
| 3 | C | 62.5 | 60 |
| 3 | T | 57.5 | 55 |
| 4 | C | 65 | 45 |
| 4 | T | 62.5 | 50 |
| 5 | C | 61 | 54 |
| 5 | T | 65 | 52 |
| 6 | C | 53.5 | 50 |
| 6 | T | 55 | 50 |
| 7 | C | 55 | 45 |
| 7 | T | 55 | 42.5 |
| 8 | C | 61 | 51 |
| 8 | T | 61.5 | 49 |

Fig. 17

Quality Control

0 & 3 hour motility 3 hour %PIA

| Bull # | Bull Code | Motility | PRI. | SEC. | pH | |
|---|---|---|---|---|---|---|
| BULL1 | JE1032 | 70 | 10 | 6 | 6.5 | |
| BULL2 | BS1137 | 65 | 12 | 9 | 6.7 | |
| BULL3 | JE1249 | 70 | 9 | 8 | 6.08 | |
| BULL4 | KB1333 | 70 | 8 | 7 | 6.27 | |
| BULL5 | AN1315 | 70 | 8 | 9 | 6.05 | |
| BULL6 | AN1317 | 70 | 12 | 11 | 6.11 | BULK SORT |
| BULL7 | JE1223 | 80 | 3 | 7 | 6.2 | |
| BULL8 | KB1327 | 75 | 2 | 9 | 6.9 | |

Fig. 19

| | Concentration | % Oriented | % Dead |
|---|---|---|---|
| Control | 162.3 | 63.4 | 17.4 |
| Treatment | 82.1 | 67.2 | 7.2 |

| | X Sort Rate | Abort Rate |
|---|---|---|
| Control | 5917 | 2270 |
| Treatment | 6232 | 2291 |

POST THAW QC

| | | 0Hr Pt | 3Hr PT | 3Hr PIA |
|---|---|---|---|---|
| Average (n=8) | Control | 55.0 | 40.0 | 63.6 |
| | Treatment | 56.8 | 41.6 | 64.6 |

Fig. 23

IVF Results

| | # put into culture | Embryo % |
|---|---|---|
| SUM Control | 1531 | 12% |
| SUM Treated | 1469 | 13% |

Fig. 24

Monomodal Analysis Results

| | |
|---|---|
| Result quality: | Good |
| Zeta Potential (mV): | -32.4 |
| Standard Deviation (mV): | 6.79 |
| QualityFactor: | 3.61 |

Titration - Average 15 Bulls

| | %ORIENTED | % improvement in orientation | % Dead | % Dead Removed | % number of sperm unaccounted for |
|---|---|---|---|---|---|
| Control | 50.2% | 0.0% | 22.4% | 0.0% | 0.0% |
| 3.5mg Treated | 64.1% | 14.0% | 5.0% | 17.4% | 19.0% |
| 3.0mg Treated | 62.8% | 12.7% | 6.2% | 16.3% | 17.3% |
| 2.5mg Treated | 61.6% | 11.5% | 7.6% | 14.8% | 16.0% |
| 2.0mg Treated | 62.4% | 12.2% | 7.4% | 15.1% | 16.6% |
| 1.0mg Treated | 59.8% | 9.6% | 10.1% | 10.1% | 10.6% |

| | Part | % Dead | % Dead Removed | % sperm unaccounted for | Ratio (Other Sperm removed for every dead) | Relative Percentage of DEAD Sperm Removed | Relative Percentage of Other (LIVE) Sperm Removed | Selectivity Factor |
|---|---|---|---|---|---|---|---|---|
| A | Control | 12.7% | | | | | | |
| | 1mg | 7.7% | 5.0% | 6.3% | 1.05 | 46.9% | 7.2% | 6.54 |
| | 2mg | 4.6% | 8.2% | 6.0% | 0.68 | 69.4% | 6.9% | 10.04 |
| | 3mg | 3.6% | 9.1% | 9.8% | 1.00 | 77.1% | 11.3% | 6.86 |

| | Part | % Dead | % Dead Removed | % number of sperm unaccounted for | Ratio (Other Sperm removed for every dead) | Relative Percentage of DEAD Sperm Removed | Relative Percentage of Other (LIVE) Sperm Removed | Selectivity Factor |
|---|---|---|---|---|---|---|---|---|
| 3A:1B | Control | 31.5% | | | | | | |
| | 1mg | 10.5% | 21.1% | 10.9% | 0.44 | 78.6% | 15.9% | 4.94 |
| | 2mg | 5.6% | 26.0% | 11.2% | 0.40 | 89.3% | 16.4% | 5.45 |
| | 3mg | 4.7% | 26.9% | 16.5% | 0.57 | 91.9% | 24.1% | 3.82 |

| | Part | % Dead | % Dead Removed | % number of sperm unaccounted for | Ratio (Other Sperm removed for every dead) | Relative Percentage of DEAD Sperm Removed | Relative Percentage of Other (LIVE) Sperm Removed | Selectivity Factor |
|---|---|---|---|---|---|---|---|---|
| 2A:2B | Control | 48.9% | | | | | | |
| | 1mg | 21.2% | 27.7% | 12.8% | 0.33 | 78.9% | 25.1% | 3.15 |
| | 2mg | 9.8% | 39.1% | 14.8% | 0.33 | 91.9% | 28.9% | 3.18 |
| | 3mg | 8.0% | 40.9% | 16.8% | 0.37 | 93.9% | 32.8% | 2.86 |

| | Part | % Dead | % Dead Removed | % number of sperm unaccounted for | Ratio (Other Sperm removed for every dead) | Relative Percentage of DEAD Sperm Removed | Relative Percentage of Other (LIVE) Sperm Removed | Selectivity Factor |
|---|---|---|---|---|---|---|---|---|
| 1A:3B | Control | 73.7% | | | | | | |
| | 1mg | 42.0% | 31.7% | 5.2% | 0.09 | 79.3% | 19.8% | 4.01 |
| | 2mg | 22.4% | 51.3% | 9.5% | 0.14 | 93.4% | 36.1% | 2.59 |
| | 3mg | 16.4% | 57.3% | 10.1% | 0.14 | 95.7% | 38.5% | 2.48 |

Fig. 28

| JE968 | Concentration | % Dead | PVR |
|---|---|---|---|
| Control | 171 | 15.32 | 62 |
| Beads before incubation | 126.6 | 1.8 | 61 |
| Beads during incubation | 114.8 | 1.4 | 63 |
| Beads after incubation | 131.1 | 2.6 | 62 |

| KB1333 | Concentration | % Dead | PVR |
|---|---|---|---|
| Control | 156.5 | 6.7 | 56 |
| Beads before incubation | 133 | 1.9 | 57 |
| Beads during incubation | 146.5 | 2.1 | 56 |
| Beads after incubation | 137 | 2.3 | 56 |

| BN1362 | Concentration | % Dead | PVR |
|---|---|---|---|
| Control | 128.9 | 29.5 | 52 |
| Beads before incubation | 76.8 | 2.5 | 50 |
| Beads during incubation | 86.59 | 3.8 | 47 |
| Beads after incubation | 81.09 | 3.6 | 46 |

| HO945 | Concentration | % Dead | PVR |
|---|---|---|---|
| Control | 141.8 | 6.82 | 60 |
| Beads before incubation | 128.2 | 3.81 | 62 |
| Beads during incubation | 125 | 3.48 | 67 |
| Beads after incubation | 121.2 | 2.95 | 68 |

| RB1401 | Concentration | % Dead | PVR |
|---|---|---|---|
| Control | 157.9 | 12.91 | 51 |
| Beads before incubation | 126.6 | 4.3 | 50 |
| Beads during incubation | 124.7 | 2.11 | 48 |
| Beads after incubation | 116.8 | 2.33 | 49 |

| JE588 | Concentration | % Dead | PVR |
|---|---|---|---|
| Control | 145.2 | 9.17 | 54 |
| Beads before incubation | 104.6 | 3.47 | 59 |
| Beads during incubation | 104.9 | 2.14 | 60 |
| Beads after incubation | 102.2 | 1.77 | 56 |

Fig. 29

| | Sample | Concentration | % Dead | Relative Percentage of DEAD Sperm Removed | Relative Percentage of Other Sperm Removed |
|---|---|---|---|---|---|
| Average | Control | 150 | 13.40% | | |
| | Beads before incubation | 116 | 2.96% | 82.9% | 13.5% |
| | Beads during incubation | 117 | 2.51% | 85.4% | 12.2% |
| | Beads after incubation | 115 | 2.59% | 85.2% | 14.0% |

Fig. 30

| | | % Dead | Concentration |
|---|---|---|---|
| Bull 1 | Control | 15.81 | 128.8 |
| | Treated | 5.31 | 107.1 |
| Bull 2 | Control | 20.16 | 114.6 |
| | Treated | 9.12 | 86.39 |
| Bull 3 | Control | 14.64 | 109.3 |
| | Treated | 12.4 | 97.51 |
| Bull 4 | Control | 13.67 | 105.5 |
| | Treated | 3.92 | 99.5 |
| Bull 5 | Control | 50.29 | 128.8 |
| | Treated | 9.67 | 53.85 |

Fig. 31

| | Part | Concentration | % Dead | Ratio (Other Sperm removed for every dead) | Relative % DEAD Removed | Relative % of Other Sperm Removed |
|---|---|---|---|---|---|---|
| 1 | Control | 128.80 | 15.81% | | | |
| | Beads before incubation | 107.10 | 5.31% | 0.48 | 72.1% | 6.5% |

| | Part | Concentration | % Dead | Ratio (Other Sperm removed for every dead) | Relative % DEAD Removed | Relative % of Other Sperm Removed |
|---|---|---|---|---|---|---|
| 2 | Control | 114.60 | 20.16% | | | |
| | Beads before incubation | 86.39 | 9.12% | 0.85 | 65.9% | 14.2% |

| | Part | Concentration | % Dead | Ratio (Other Sperm removed for every dead) | Relative % DEAD Removed | Relative % of Other Sperm Removed |
|---|---|---|---|---|---|---|
| 3 | Control | 109.30 | 14.64% | | | |
| | Beads before incubation | 97.51 | 12.40% | 2.02 | 24.4% | 8.4% |

| | Part | Concentration | % Dead | Ratio (Other Sperm removed for every dead) | Relative % DEAD Removed | Relative % of Other Sperm Removed |
|---|---|---|---|---|---|---|
| 4 | Control | 105.50 | 13.67% | | | |
| | Beads before incubation | 94.00 | 3.92% | 0.07 | 74.4% | 0.8% |

| | Part | Concentration | % Dead | Ratio (Other Sperm removed for every dead) | Relative % DEAD Removed | Relative % of Other Sperm Removed |
|---|---|---|---|---|---|---|
| 5 | Control | 128.80 | 50.29% | | | |
| | Beads before incubation | 53.85 | 9.67% | 0.26 | 92.0% | 24.0% |

Fig. 32

| | Part | Concentration | % Dead | % number of sperm unaccounted for | Ratio (Other Sperm removed for every dead) | Relative Percentage of DEAD Sperm Removed | Relative Percentage of Other (LIVE) Sperm Removed |
|---|---|---|---|---|---|---|---|
| 1 | Control | 130.5 | 12.20% | | | | |
| | Treated | 105.7 | 3.19% | 9.4% | 0.98 | 78.8% | 10.7% |
| 2 | Control | 134.6 | 14.96% | | | | |
| | Treated | 99.29 | 3.13% | 13.6% | 1.07 | 84.6% | 16.0% |
| 3 | Control | 115.5 | 12.03% | | | | |
| | Treated | 108.3 | 4.26% | -1.8% | -0.22 | 66.8% | -2.0% |
| 4 | Control | 137.3 | 6.26% | | | | |
| | Treated | 113.4 | 2.38% | 13.1% | 3.05 | 68.6% | 14.0% |
| 5 | Control | 125.3 | 13.72% | | | | |
| | Treated | 108 | 2.86% | 2.6% | 0.23 | 82.0% | 3.0% |

Fig. 33

After wash 1

| | | % Dead | Concentration |
|---|---|---|---|
| Bull 1 | Control | 12.2 | 130.5 |
| | Treated | 3.19 | 105.7 |
| | Beads | 74.37 | |
| Bull 2 | Control | 14.96 | 134.6 |
| | Treated | 3.13 | 99.29 |
| | Beads | 72.81 | |
| Bull 3 | Control | 12.03 | 115.5 |
| | Treated | 4.26 | 108.3 |
| | Beads | 62.07 | |
| Bull 4 | Control | 6.26 | 137.3 |
| | Treated | 2.38 | 113.4 |
| | Beads | 45.11 | |
| Bull 5 | Control | 13.72 | 125.3 |
| | Treated | 2.86 | 108 |
| | Beads | 66.71 | |

After wash 1

| | | % Dead | Concentration |
|---|---|---|---|
| AVERAGE | In Control | 11.83 | 128.64 |
| | In Treated | 3.16 | 106.94 |
| | In Beads | 64.21 | |

After wash 2

| | | % Dead | % Live |
|---|---|---|---|
| Bull 1 | In beads | 95.8 | 3.83 |
| | In live recovery | 18.87 | 80.31 |
| | Mixed with collection #1 | 4.67 | 94.63 |
| Bull 2 | In beads | 98.46 | 1.32 |
| | In live recovery | 15.49 | 83.44 |
| | Mixed with collection #1 | 5.57 | 92.69 |
| Bull 3 | In beads | 97.81 | 2.06 |
| | In live recovery | 11.01 | 88.2 |
| | Mixed with collection #1 | 6.05 | 91.8 |
| Bull 4 | In beads | 87.8 | 8.1 |
| | In live recovery | 11.01 | 88.2 |
| | Mixed with collection #1 | 3.73 | 93.99 |
| Bull 5 | In beads | 97.11 | 2.71 |
| | In live recovery | 13.62 | 85.51 |
| | Mixed with collection #1 | 4.19 | 94.08 |

After wash 2

| | | % Dead | % Live |
|---|---|---|---|
| AVERAGE | In beads | 95.40 | 3.60 |
| | In live recovery | 14.00 | 85.13 |
| | Mixed with collection #1 | 4.84 | 93.44 |

Fig. 34

| Animal ID | Event Rate AV | Abort Rate AV | Sort Rate X AV | Oriented AV | Dead AV | X AV | PVR | Over Range |
|---|---|---|---|---|---|---|---|---|
| Beads Bull 1 Control | 36455 | 2701 | 4754 | 54.86 | 15.01 | 42.18 | 51.18 | 3.92 |
| Beads Bull 1 Treatment | 37429 | 3177 | 6071 | 64.97 | 5.30 | 42.18 | 61.05 | 3.55 |
| Beads Bull 2 Control | 40983 | 3432 | 5610 | 59.86 | 13.69 | 41.00 | 63.68 | 2.92 |
| Beads Bull 2 Treatment | 41357 | 3603 | 6335 | 68.17 | 3.18 | 40.35 | 61.93 | 2.82 |
| Beads Bull 3 Control | 43384 | 3724 | 5823 | 62.60 | 9.89 | 40.17 | 58.53 | 2.91 |
| Beads Bull 3 Treatment | 42386 | 3647 | 5958 | 67.85 | 3.34 | 37.24 | 56.45 | 3.23 |
| Beads Bull 4 Control | 37778 | 2707 | 4608 | 56.85 | 14.45 | 38.63 | 45.58 | 6.36 |
| Beads Bull 4 Treatment | 37792 | 3085 | 5615 | 63.36 | 4.88 | 39.88 | 49.36 | 4.01 |
| Beads Bull 5 Control | 36566 | 2728 | 4736 | 58.46 | 7.89 | 38.28 | 45.83 | 8.65 |
| Beads Bull 5 Treatment | 37580 | 2961 | 5236 | 62.53 | 1.41 | 38.18 | 43.93 | 8.44 |

Fig. 35

| | Part | Concentration | % Dead | % Dead Removed | % unaccounted for | Ratio (Other Sperm removed for every dead) | Relative % of DEAD Sperm Removed | Relative % of Other Sperm Removed |
|---|---|---|---|---|---|---|---|---|
| Bull 1 | Control | 139 | 16.00% | | | | | |
| | Treated | 112.9 | 4.80% | 11.2% | 6.7% | 0.55 | 75.6% | 7.9% |

| | Part | Concentration | % Dead | % Dead Removed | % unaccounted for | Ratio (Other Sperm removed for every dead) | Relative Percentage of DEAD Sperm Removed | Relative Percentage of Other (LIVE) Sperm Removed |
|---|---|---|---|---|---|---|---|---|
| Bull 2 | Control | 120.8 | 13.40% | | | | | |
| | Treated | 102.8 | 3.40% | 10.0% | 4.4% | 0.42 | 78.4% | 5.1% |

| | Part | Concentration | % Dead | % Dead Removed | % unaccounted for | Ratio (Other Sperm removed for every dead) | Relative Percentage of DEAD Sperm Removed | Relative Percentage of Other (LIVE) Sperm Removed |
|---|---|---|---|---|---|---|---|---|
| Bull 3 | Control | 123.3 | 9.80% | | | | | |
| | Treated | 115.3 | 4.00% | 5.8% | 0.4% | 0.07 | 61.8% | 0.5% |

| | Part | Concentration | % Dead | % Dead Removed | % unaccounted for | Ratio (Other Sperm removed for every dead) | Relative Percentage of DEAD Sperm Removed | Relative Percentage of Other (LIVE) Sperm Removed |
|---|---|---|---|---|---|---|---|---|
| Bull 4 | Control | 156.3 | 14.70% | | | | | |
| | Treated | 134.6 | 4.80% | 9.9% | 3.3% | 0.31 | 71.9% | 3.9% |

| | Part | Concentration | % Dead | % Dead Removed | % number of sperm unaccounted for | Ratio (Other Sperm removed for every dead) | Relative Percentage of DEAD Sperm Removed | Relative Percentage of Other (LIVE) Sperm Removed |
|---|---|---|---|---|---|---|---|---|
| Bull 5 | Control | 112.8 | 7.90% | | | | | |
| | Treated | 102.6 | 1.50% | 6.4% | 2.5% | 0.38 | 82.7% | 2.7% |

| | Part | Concentration | % Dead | % Dead Removed | % unaccounted for | Ratio (Other Sperm removed for every dead) | Relative Percentage of DEAD Sperm Removed | Relative Percentage of Other (LIVE) Sperm Removed |
|---|---|---|---|---|---|---|---|---|
| Average | Control | 130 | 12.4% | | | | | |
| | Treated | 114 | 3.7% | 8.7% | 3.5% | 0.35 | 74.1% | 4.0% |

Fig. 36

| | | % Motile 0Hr | % Motile 3Hr | % Viable | % Purity |
|---|---|---|---|---|---|
| Bull 1 | Control | 70% | 52% | 33% | 90% |
| | Treated | 70% | 63% | 32% | 96% |
| Bull 2 | Control | 70% | 61% | 48% | 95% |
| | Treated | 65% | 58% | 46% | 95% |
| Bull 3 | Control | 75% | 40% | 38% | 95% |
| | Treated | 75% | 50% | 47% | 96% |
| Bull 4 | Control | 60% | 58% | 27% | 96% |
| | Treated | 58% | 45% | 36% | 94% |
| Bull 5 | Control | 68% | 63% | 35% | 95% |
| | Treated | 65% | 50% | 38% | 97% |

Fig. 37

| Animal ID | Event Rate | Abort Rate | Sort Rate X | % Oriented | % Dead | % X Region | % PVR | % Over Range |
|---|---|---|---|---|---|---|---|---|
| **Bull 1 Control** | 33832 | 2529 | 4819 | 53.52 | 9.68 | 43.95 | 59.73 | 9.17 |
| **Bull 1 Treatment** | 36010 | 2762 | 5209 | 55.68 | 3.34 | 44.05 | 58.31 | 5.66 |
| **Bull 2 Control** | 43201 | 3720 | 5823 | 56.23 | 8.48 | 43.71 | 49.47 | 4.23 |
| **Bull 2 Treatment** | 43136 | 3807 | 6078 | 60.47 | 3.55 | 42.06 | 50.26 | 4.83 |
| **Bull 3 Control** | 45296 | 3799 | 5704 | 57.24 | 4.90 | 41.88 | 43.97 | 3.93 |
| **Bull 3 Treatment** | 45065 | 3839 | 5884 | 60.15 | 1.76 | 39.79 | 43.59 | 3.38 |
| **Bull 4 Control** | 37218 | 2833 | 4998 | 58.98 | 9.72 | 39.87 | 40.71 | 4.14 |
| **Bull 4 Treatment** | 37836 | 3065 | 5499 | 62.25 | 4.40 | 39.83 | 40.60 | 2.63 |
| **Bull 5 Control** | 40301 | 3265 | 4951 | 60.65 | 11.44 | 36.36 | 39.36 | 1.35 |
| **Bull 5 Treatment** | 39019 | 3279 | 5329 | 68.66 | 3.19 | 34.68 | 38.74 | 1.52 |

Fig. 38

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Bull 1 | Control | 127.3 | 9.82% | | | | | |
| | Treated | 110.4 | 3.38% | 6.4% | 6.4% | 0.93 | 70.1% | 7.1% |

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Bull 2 | Control | 123.7 | 9.17% | | | | | |
| | Treated | 111.1 | 3.54% | 5.6% | 4.2% | 0.70 | 65.3% | 4.6% |

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Bull 3 | Control | 134.1 | 4.60% | | | | | |
| | Treated | 121.6 | 1.72% | 2.9% | 6.3% | 2.07 | 66.1% | 6.6% |

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Bull 4 | Control | 147.9 | 10.18% | | | | | |
| | Treated | 119.1 | 4.30% | 5.9% | 12.8% | 1.90 | 66.0% | 14.2% |

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Bull 5 | Control | 119.8 | 11.89% | | | | | |
| | Treated | 105 | 3.42% | 8.5% | 3.5% | 0.39 | 74.8% | 3.9% |

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Bull 6 | Control | 127.6 | 4.58% | | | | | |
| | Treated | 122.7 | 1.80% | 2.8% | 1.0% | 0.35 | 62.2% | 1.0% |

| | Part | Concentration | % Dead | % Dead Removed | % number of sperm unaccounted for | Ratio (Other Sperm removed for every dead) | Relative Percentage of DEAD Sperm Removed | Relative Percentage of Other Sperm Removed |
|---|---|---|---|---|---|---|---|---|
| Average | Control | **130.1** | **8.37%** | | | | | |
| | **Treated** | **115.0** | **3.03%** | **5.3%** | **5.7%** | **1.05** | **67.4%** | **6.2%** |

Fig. 39

| | % Dead in Beads |
|---|---|
| Bull 1 | 91.42 |
| Bull 2 | 90.22 |
| Bull 3 | 82.38 |
| Bull 4 | 81.42 |
| Bull 5 | 94.05 |
| Bull 6 | 84.9 |

Average: 87.9 % Dead in Matrix (12% "other" sperm)

| After Second Wash of Beads | % Dead |
|---|---|
| In beads | 95.40 |
| In live recovery | 14.00 |

Fig. 40

| | | % Motile 0Hr | % Motile 3Hr | % Viable | % Purity |
|---|---|---|---|---|---|
| Bull 1 | Control | 45 | 35 | 20.8 | 95 |
| | Treated | 45 | 30 | 30.33 | 95 |
| Bull 2 | Control | 73 | 58 | 41.22 | 94 |
| | Treated | 70 | 62 | 26.39 | 92 |
| Bull 3 | Control | 70 | 60 | 32.61 | 93 |
| | Treated | 68 | 57 | 32.1 | 94 |
| Bull 4 | Control | 75 | 68 | 32.69 | 94 |
| | Treated | 78 | 70 | 47.79 | 95 |
| Bull 5 | Control | 69 | 67 | 49.75 | 95 |
| | Treated | 65 | 65 | 45.35 | 94 |
| Bull 6 | Control | 60 | 50 | 39.29 | 96 |
| | Treated | 68 | 56 | 32.21 | 95 |

Fig. 41

IVF Results

Set 1

| | Oocytes put into culture |
|---|---|
| TOTAL Control | 2782 |
| TOTAL Treated | 2841 |

| | % Oocyte to Embryo | % Morula to Embryo |
|---|---|---|
| TOTAL Control | 4.89% | 11.45% |
| TOTAL Treated | 4.86% | 11.98% |
| | 99% | 105% |

Set 2 – Under stressing situations (High $CO_2$ levels at IVF lab)

| | Oocytes put into culture |
|---|---|
| TOTAL Control | 1784 |
| TOTAL Treated | 1858 |

| | % Oocyte to Embryo | % Morula to Embryo |
|---|---|---|
| TOTAL Control | 1.46% | 3.62% |
| TOTAL Treated | 3.93% | 10.20% |
| | 270% | 282% |

Fig. 42

CELL PROCESSING USING MAGNETIC PARTICLES

The present invention relates to compositions comprising magnetic particles, the methods of using these compositions in processing animal sperm, the resulting sperm and embryo products, and the methods of use of these compositions to increase the efficiency, efficacy and/or speed of cell processing and artificial insemination techniques.

BACKGROUND

Assisted reproductive technology (ART) includes such techniques as in vitro fertilization (IVF), artificial insemination (AI), intracytoplasmic sperm injection (ICSI) (other techniques using enucleated cells) and multiple ovulation and embryo transfer (MOET) (as well as other embryo transfer techniques) and is used across the animal kingdom. ART methods are generally expensive, time consuming and marginally successful given the inherent fragility of gametes when outside of their natural environments. Furthermore, the use of ART within the animal breeding industry in a commercially feasible manner is additionally challenging due to the limited availability of genetically desirable gametes (sperm or oocytes). One way to lower the cost of ART and to improve its commercial feasibility is to increase the efficiency of the involved processes by improving the viability and overall quality of gametes used in ART. Although there has been a growing interest in this field over the course of the last decade or so, there still remains a strong need to increase the overall quality of gametes for use in ART, especially when breeding focuses on pre-natal gender selection, including improving gametes viability, motility and fertility, as well as other longevity characteristics.

For example, in conventional AI, one problem limiting its commercial application in certain species is the need to use extremely high number of sperm per AI dose to ensure successful fertilization currently. In swine in particular, the need for improved sperm quality is especially strong since the typical dose of boar sperm required for successful fertilization using conventional artificial insemination techniques, such as intra-cervical insemination, is currently $1\times10^9$ sperm to $3\times10^9$ sperm.

Processing gametes such as flushed oocytes or sperm, both conventional and sex sorted, before their use in ART may add a tremendous amount of stress on the gamete cell(s) and often negatively impacts their cellular integrity and membrane structure, which in turn may be reflected in decreased viability, motility and fertility. An example of processing gametes prior to their use in ART is the sorting of sperm based on sex (known as “gender enrichment” or “sex sorting”), which is a now commonly used procedure to minimize wasted births of the wrong sex for selective breeding in the livestock industry. In some species, however, it is still cost prohibitive and can represent a financial risk to those with smaller breeding herds. Sex sorting includes processes that physically separate X and Y bearing sperm from each other into separate subpopulations, as well as processes in which sperm bearing the undesired sex chromosome in a sperm sample are selectively killed, compromised, disabled, rendered immotile, or otherwise rendered infertile by, for example, laser ablation/photo damage techniques to render a gender enriched population of sperm.

The sex sorting process severely stresses and damages the cells and produces a low percentage of useful sperm, which although capable of fertilizing matured oocytes, may have reduced viability, motility and fertility compared to unprocessed cells. Typically, sex sorting involves many harsh steps including but not limited to: the initial collection and handling of sperm ejaculate, which naturally starts to deteriorate rapidly upon collection; the staining of sperm, which involves binding of an excitable dye to the DNA or a harmful membrane selection procedure; the physical sorting of the sperm using high energy fluorescence that physically energizes the dye that is bound to the DNA, forced orientation through a narrow orifice, and application of an electrical charge to the cell; the physical collection of the cells into a receiving container, which often shocks the fragile cell upon contact; the osmotic stresses associated with dilution of the sperm droplet in collection media; and the storage of the sorted sperm usually by freezing, which is well known to raise havoc with the cell's membrane systems. Each step places the processed sperm under abnormal stress that diminishes the overall motility, viability and/or fertility of the sperm. The result can lead to less efficient samples for use in ART, such as IVF and AI, and other types of subsequent or further processing.

Even non-sorted processed sperm exhibits significant losses in fertility, viability and motility when being collected, handled and transported without freezing, and noticeably experiences significant stress when mixed with cryoprotectant and frozen and thawed. Many in the field have tried to improve methods for the use on unsorted, conventional semen to minimize loss in the handling processes associated with in vitro handling, preservation and use of semen samples.

Regardless of the processing, sperm lose their potential to fertilize when exposed to: elevated temperatures, abnormal buffers, stains, altered pH systems, physical pressurized orientation as when forced through a nozzle or when oscillated to form drops in a flow cytometer, radiation used to illuminate the DNA binding dye, physical stressors associated with separation and collection techniques, cryoprotectants, freezing, thawing and micromanipulation by the handler.

There remains a continuing need to improve current methods of ART to reduce the cost and to make the procedures more dependable, efficient, fast and efficacious and commercially feasible to those on a restricted budget, especially for smaller breeders for whom sex-selection breeding may be a high risk and expensive option. Accordingly, there is a significant need for improved sperm processing techniques.

SUMMARY OF THE INVENTION

A broad object of the present invention is to provide improvements in the motility, viability, fertility and overall integrity of processed sperm, particularly sperm that undergo analysis and/or sex sorting. In order to achieve such improvements, one aspect of the present invention broadly encompasses compositions comprising magnetic particles and the use of such compositions in the cell sorting process. Other aspects of the invention encompass methods of using sperm processed with magnetic particles in various ART procedures, including but not limited to, IVF, AI, ICSI and MOET.

In one embodiment, the invention comprises a composition for magnetic cellular manipulation comprising a plurality of particles. Each particle in the plurality of particles may include a magnetic substrate. The magnetic substrate may be characterized by a magnetic susceptibility greater than zero. Such particles are generally referred to hereinafter as particles or magnetic particles. Each particle in the plurality of particles may also include a chargeable silicon-containing compound. The chargeable silicon-containing compound may coat at least a portion of the magnetic substrate.

In another embodiment, a method for magnetic cellular manipulation is provided. The method may include contacting a composition with a biological sample to form a mixture. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate. The biological sample may include cells, such as sperm and/or cellular structures. The method may also include applying a magnetic field to the mixture to manipulate the composition.

In one embodiment, a kit for magnetic cellular manipulation is provided. The kit may include instructions. The instructions may include contacting a composition with a biological sample to form a mixture. The instructions may also include applying a magnetic field to the mixture to manipulate the composition. The kit may also include the composition. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate.

In certain embodiments of the invention, compositions comprising magnetic particles comprise sperm at a concentration of $500\times10^6$ cells/ml or less; $400\times10^6$ cells/ml or less; $300\times10^6$ cells/ml or less; $200\times10^6$ cells/ml or less; $180\times10^6$ cells/ml or less; $160\times10^6$ cells/ml or less; $120\times10^6$ cells/ml or less; $100\times10^6$ cells/ml or less; or $50\times10^6$ cells/ml or less.

In other embodiments of the invention, compositions comprising magnetic particles comprise 0.01-3 mg of magnetic particles per 100 million sperm; 0.1-2 mg of magnetic particles per 100 million sperm; 0.1-2 mg of magnetic particles per 100 million sperm; 0.2-1.8 mg of magnetic particles per 100 million sperm; 0.5-1.6 mg of magnetic particles per 100 million sperm; 0.7-1.5 mg of magnetic particles per 100 million sperm; 1.0-1.4 mg of magnetic particles per 100 million sperm; 1.1-1.3 mg of magnetic particles per 100 million sperm; or 1.125 mg of magnetic particles per 100 million sperm.

In some embodiments of the invention, the magnetic particles have a size distributions from about 300 nm to about 800 nm; about 50 nm to about 400 nm; about 1 nm to about 1 μm; from about 10 nm to about 900 nm; from about 10 nm to about 700 nm; from about 10 nm to about 500 nm; from about 10 nm to about 400 nm; from about 10 nm to about 300 nm; from about 10 nm to about 250 nm; from about 10 nm to about 200 nm; from about 10 nm to about 190 nm; from about 10 nm to about 180 nm; from about 10 nm to about 150 nm; from about 20 nm to about 700 nm; from about 20 nm to about 500 nm; from about 20 nm to about 400 nm; from about 20 nm to about 300 nm; from about 20 nm to about 250 m; from about 20 nm to about 200 nm; from about 20 nm to about 190 nm; from about 20 nm to about 180 nm; from about 20 nm to about 150 nm; from about 30 nm to about 500 nm; from about 30 nm to about 400 nm; from about 30 nm to about 300 nm; from about 30 nm to about 250 m; from about 30 nm to about 200 nm; from about 30 nm to about 190 nm; from about 30 nm to about 180 nm; from about 30 nm to about 150 nm. In a further embodiment of the invention, the magnetic particles exclude particles having a size of 200 nm.

In certain embodiments of the invention, sex sorting of sperm may be accomplished using any process or device known in the art for cell analysis, sorting and/or population enrichment including but not limited to use of a flow cytometer or use of a microfluidic chip. As contemplated herein, sex sorting in addition to encompassing techniques for physically separating, or isolating, X and Y bearing sperm from each other as with droplet sorting and fluid switching sorting, also encompasses techniques for gender enrichment in which sperm bearing the undesired sex chromosome are killed, immobilized, or otherwise rendered infertile, such as by use of laser ablation/photo damage techniques.

In one embodiment of the invention, compositions comprising magnetic particles may comprise one or more buffers, including but not limited to carbonates, phosphates, citrates, acetates, lactates, and combinations thereof, or a solution containing a salt, a carbohydrate, or a combination thereof can be employed in some of the embodiments of the invention, such as, but not limited to, Tris (Tris(hydroxymethyl)aminomethane), TES (Tris-EDTA-Sucrose), HEPES (4-(2-Hydroxyethyl)-1-piperazine-1-ethanesulfonic acid), TALP (Tyrode's albumin lactate pyruvate), TCA (Tris-egg yolk A), PBS (phosphate-buffered saline), citrate, milk and derivatives thereof, as discussed in detail in U.S. Pat. No. 7,208,265 the contents of which is hereby incorporated by reference in its entirety.

In certain embodiments, compositions comprising magnetic particles may comprise one or more chelators, including but not limited to, deferoxamine, deferasirox, penicillamine, alpha lipoic acid, DMPS (2,3-Dimercapto-1-propanesulfonic acid), DMSA (2,3-Dimercaptosuccinic acid), dimercaprol and aminopolycarboxylic acids (complexones), including but not limited to Fura-2 ($C_{29}H_{22}N_3O_{14}K_5$), IDA (Iminodiacetic acid), NTA (Nitrilotriacetic acid), EDTA (ethylenediaminetetraacetic acid), DTPA (diethylenetriaminepentaacetic acid), EGTA (ethylene glycol-bis(β-aminoethyl ether)-N,N,N',N'-tetraacetic acid), BAPTA (1,2-bis(o-aminophenoxy) ethane-N,N,N',N'-tetraacetic acid), NOTA (1,4,7-triazacyclononane-1,4,7-triacetic acid), DOTA (tetraxetan), and nicotianamine, and derivatives thereof.

In certain embodiments, compositions comprising magnetic particles may comprise low sugar media. The term "sugar" as used herein refers to mono- or di-saccharides that are generally metabolized by mammalian sperm, e.g., glucose and fructose. The term "sugar additive" as used herein means sugar that is added to a media as a discrete compound and not as a naturally occurring component of another additive in the media such as egg yolk, seminal fluid or milk.

In certain embodiments of the invention, low sugar media comprises less than about 50 mM, 45 mM, 40 mM, 35 mM, 30 mM, 25 mM, 20 mM, 19 mM, 18 mM, 17 mM, 16.5 mM, 16 mM, 15.5 mM, 15 mM, 14.5 mM, 14 mM, 13.5 mM, 13 mM, 12.5 mM, 12 mM, 11.5 mM, 11 mM, 10.9 mM, 10.8 mM, 10.7 mM, 10.6 mM, 10.5 mM, 10.4 mM, 10.3 mM, 10.2 mM, 10.1 mM, 10.0 mM, 10 mM, 9.75 mM, 9.5 mM, 9.25 mM, 9.0 mM, 9 mM, 5 mM of sugar additive. In other embodiments of the invention, low sugar media comprises about 1-5 mM, 5-10 mM, 10-15 mM, 15-20 mM, 20-25 mM, 25-30 mM, 35-40 mM, or 45-50 mM of sugar additive. In further embodiments of the invention, low sugar media comprises about 1-5 mM, 1-10 mM, 1-15 mM, 1-20 mM, 1-25 mM, 1-30 mM, 1-35 mM, 1-40 mM, 1-45 mM, or 1-50 mM of sugar additive. In yet further embodiments of the invention, low sugar media comprises about 0.1 ppm to about 5 mM, about 0.1 ppm to about 10 mM, about 0.1 ppm to about 15 mM, about 0.1 ppm to about 20 mM, about 0.1 ppm to about 25 mM, about 0.1 ppm to about 30 mM, about 0.1 ppm to about 35 mM, about 0.1 ppm to about 40 mM, about 0.1 ppm to about 45 mM, or about 0.1 ppm to about 50 mM of sugar additive. In other embodiments of the invention, low sugar media comprises about 1 mM, 2 mM, 3 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.0 mM, 5.1 mM, 5.2 mM, 5.3 mM, 5.4 mM, 5.5 mM, 5.6 mM, 5.7 mM, 5.8 mM, 5.9 mM, 6 mM, 7 mM, 8 mM, 9 mM, 9.1, 9.2, 9.3, 9.4, 9.5, 9.6, 9.7, 9.8, 9.9, 10 mM, 10.0, 10.1, 10.2, 10.3, 10.4, 10.5, 10.6, 10.7, 10.8, 10.9, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, or 50 mM of sugar additive. In a further embodiment of the invention, low sugar media comprises about 1-10 mM, 2-9 mM, 3-6 mM, 4-6 mM, or 4-5 mM of sugar additive. In yet another embodiment of the invention, low sugar media comprises about 5-15 mM, 6-14 mM, 7-13 mM, 8-12 mM, 9-11 mM or 9-10 mM of sugar additive. In yet another embodiment of the invention, low sugar media comprises no sugar additive or at most, trace amounts of sugar additive (i.e., no more than 0.1-20 ppm of sugar additive).

In certain embodiments of the invention, low sugar media comprises less than about 50 mM, 45 mM, 40 mM, 35 mM, 30 mM, 25 mM, 20 mM, 19 mM, 18 mM, 17 mM, 16.5 mM, 16 mM, 15.5 mM, 15 mM, 14.5 mM, 14 mM, 13.5 mM, 13 mM, 12.5 mM, 12 mM, 11.5 mM, 11 mM, 10.9 mM, 10.8 mM, 10.7 mM, 10.6 mM, 10.5 mM, 10.4 mM, 10.3 mM, 10.2 mM, 10.1 mM, 10.0 mM, 10 mM, 9.75 mM, 9.5 mM, 9.25 mM, 9.0 mM, 9 mM, 5 mM of sugar. In other embodiments of the invention, low sugar media comprises about 1-5 mM, 5-10 mM, 10-15 mM, 15-20 mM, 20-25 mM, 25-30 mM, 35-40 mM, or 45-50 mM of sugar. In further embodiments of the invention, low sugar media comprises about 1-5 mM, 1-10 mM, 1-15 mM, 1-20 mM, 1-25 mM, 1-30 mM, 1-35 mM, 1-40 mM, 1-45 mM, or 1-50 mM of sugar. In yet further embodiments of the invention, low sugar media comprises about 0.1 ppm to about 5 mM, about 0.1 ppm to about 10 mM, about 0.1 ppm to about 15 mM, about 0.1 ppm to about 20 mM, about 0.1 ppm to about 25 mM, about 0.1 ppm to about 30 mM, about 0.1 ppm to about 35 mM, about 0.1 ppm to about 40 mM, about 0.1 ppm to about 45 mM, or about 0.1 ppm to about 50 mM of sugar. In other embodiments of the invention, low sugar media comprises about 1 mM, 2 mM, 3 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.0 mM, 5.1 mM, 5.2 mM, 5.3 mM, 5.4 mM, 5.5 mM, 5.6 mM, 5.7 mM, 5.8 mM, 5.9 mM, 6 mM, 7 mM, 8 mM, 9 mM, 9.1, 9.2, 9.3, 9.4, 9.5, 9.6, 9.7, 9.8, 9.9, 10 mM, 10.0, 10.1, 10.2, 10.3, 10.4, 10.5, 10.6, 10.7, 10.8, 10.9, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, or 50 mM of sugar. In a further embodiment of the invention, low sugar media comprises about 1-10 mM, 2-9 mM, 3-6 mM, 4-6 mM, or 4-5 mM of sugar. In yet another embodiment of the invention, low sugar media comprises about 5-15 mM, 6-14 mM, 7-13 mM, 8-12 mM, 9-11 mM or 9-10 mM of sugar. In another embodiment of the invention, low sugar media comprises no sugar or at most, trace amounts of sugar (i.e., no more than 0.1-20 ppm of sugar).

In other embodiments, compositions comprising magnetic particles may comprise one or more "organic stress reducing" agents (OSRs), which may comprise an antioxidant, a vitamin or other organic molecule involved directly or indirectly in modulating physiological stresses in the cell. In certain embodiments, compositions comprising magnetic particles may comprise one or more OSRs, each in the concentration range of 0.01 mg/ml to 5 mg/ml. Various OSRs can be used in the context of the current invention, including but not limited to: catalase, superoxide dismutase (SOD), SOD mimics, glutathione, glutathione reductase, glutathione peroxidase, pyruvate, mercaptoethanol, butylated hydroxytoluene (BHT), lipoic acid, flavins, quinones, vitamin K (and related vitamers), vitamin B12 (and related vitamers), with 'vitamers' defined as compounds having the same vitamin activity (such as cobalamin, cyanocobalamin, methylcobalamin, adenosylcobalamin, hydroxocobalamin, and pseudo-B12), vitamin E (including its vitamers, tocopherols (α, β, γ), tocotrienols, and α-tocopheryl), alpha-ketoglutarate (also known as α-KG, AKG or oxo-glutarate) and various biological forms of AKG (such as arginine, aspartate, lysine, and similar derivatives), other compounds that regulate nitric oxide in the cell including malondialdehyde (MDA) and asymmetric dimethylarginine (ADMA), and biologically active derivatives thereof.

Certain embodiments of the invention utilize concentrations of OSRs selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In other embodiments, compositions comprising magnetic particles may comprise one or more tricarboxylic acid cycle intermediates, including but not limited to, pyruvate, acetyl-CoA, citrate, isocitrate, α-ketoglutarate, succinyl-CoA, succinate, fumarate, malate, oxaloacetate, and derivatives thereof, including but not limited to isomers and acids. In a particular embodiment, compositions comprising magnetic particles comprises two or more tricarboxylic acid cycle intermediates, including but not limited to, pyruvate, acetyl-CoA, citrate, isocitrate, α-ketoglutarate, succinyl-CoA, succinate, fumarate, malate, oxaloacetate, and derivatives thereof, including but not limited to isomers and acids.

Certain embodiments of the invention utilize concentrations of a tricarboxylic acid cycle intermediate selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In other embodiments, compositions comprising magnetic particles may comprise one or more cryoprotectants, including but not limited to, propylene glycol, dimethyl sulfoxide, ethylene glycol and glycerol, or a combination thereof. In certain embodiments, compositions comprising magnetic particles may comprise a concentration of cryoprotectant by percent volume selected from the following: less than 1%; 1-5%; 5%; 5 to 10%; 10%; 10 to 20%; 16.7%; 20%; 20 to 30%; or 30 to 40%.

In a further embodiment, compositions comprising magnetic particles may comprise one or more antioxidants, including but not limited to catalase, superoxide dismutase (SOD), SOD mimics, glutathione, glutathione reductase, glutathione peroxidase, pyruvate, mercaptoethanol, butylatedhydroxytoluene (BHT), lipoic acid, flavonoids, phenolic acids and their esters, quinines, vitamin A (and related vitamers), vitamin C (and related vitamers), vitamin K (and related vitamers), vitamin B12 (and related vitamers), with "vitamers" defined as compounds having the same vitamin activity (such as cobalamin, cyanocobalamin, methylcobalamin, adenosylcobalamin, hydroxocobalamin, and pseudo-B12), vitamin E (including its vitamers, tocopherols (α, β, γ), tocotrienols, and α-tocopheryl), α-ketoglutarate (also known as α-KG, AKG or oxo-glutarate) and various biological forms of AKG (such as arginine, aspartate, lysine, and similar derivatives), coenzyme Q, manganese, iodide, melatonin and carotenoid terpenoids.

Certain embodiments of the invention utilize concentrations of an antioxidant selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In yet another embodiment, compositions comprising magnetic particles may comprise one or more protein sources, including but not limited to, egg yolk, egg yolk extract, milk (including heat homogenized and skim), milk extract, soy protein, soy protein extract, serum albumin, bovine serum albumin, human serum substitute supplement, seminal proteins, such as, for example, whole seminal plasma or seminal plasma extracts, and derivatives thereof.

In certain embodiments, compositions comprising magnetic particles may comprise a concentration of protein source by percent volume selected from the following: 1-5%; 5%; 5 to 10%; 10%; 10 to 20%; 16.7%; 20%; 20 to 30%; or 30 to 40%.

In a further embodiment of the invention, compositions comprising magnetic particles may comprise one or more antimicrobial or antibiotic agents, including but not limited to, tylosin, gentamicin, lincomycin, spectinomycin, Linco-Spectin® (lincomycin hydrochloride-spectinomycin), penicillin, streptomycin, ticarcillin, polymyxin B, and their derivatives. If included, the antibiotics may be present in a concentration of about 50 μg to about 800 μg per ml of semen. In another embodiment compositions comprising magnetic particles may comprise a detergent, including but not limited to, an alkyl ionic detergent such as sodiumdodecyl sulfate (SDS).

In another embodiment, compositions comprising magnetic particles may comprise one or more salts, including but not limited to, NaCl, KCl, $MgCl_2$, $CaCl_2$) and any combination of a salt-forming anion, including but not limited to acetate ($CH_3COO^-$), carbonate ($CO_3^{2-}$), chloride ($Cl^-$), citrate ($HOC(COO^-)(CH_2COO^-)_2$), fluoride (F), nitrate ($NO_3^-$), nitrite ($NO_2^-$), phosphate ($PO_4^{3-}$) and sulfate ($SO_4^{2-}$) and a salt-forming cation, including but not limited to, ammonium ($NH_4^+$), calcium ($Ca_2^+$), iron ($Fe_2^+$ and $Fe_3^+$), magnesium ($Mg_2^+$), potassium ($K^+$), pyridinium ($C_5H_5NH^+$), quaternary ammonium ($NR_4^+$) and sodium ($Na^+$).

In yet another embodiment, compositions comprising magnetic particles may comprise one or more growth factors including but not limited to transforming growth factors ("TGF"), such as, for example, TGFβ-1 and TGFβ-2, and insulin-like growth factors ("IGF"), such as for example, IGF-1.

Another embodiment of the invention encompasses a staining solution comprising magnetic particles and a DNA selective dye. DNA selective dyes for use with the invention include but are not limited to UV light excitable, selective dyes, such as Hoechst 33342 (bisBenzimide H 33342) and Hoechst 33258 (bisBenzimide H 33258) and visible light excitable dyes, such as SYBR®-14 and bisbenzimide-BODIPY® conjugate 6-{[3-((2Z)-2-{[1-(difluoroboryl)-3,5-dimethyl-1H-pyrrol-2yl]methylene}-2H-pyrrol-5-yl) propanoyl]amino}-N-[3-(methyl{3-[({4-[6-(4-methylpiperazin-1-yl)-1H,3'H-2,5'bibenzimidazol-2'-yl] phenoxy}acetyl)amino]propyl}amino)propyl]hexanamide. Each of these dyes may be used alone or in combination. In another embodiment, the staining solution further comprises one or more dye quenchers, including but not limited to F&DC red food dye No. 40 and yellow food dye No. 4. In yet another embodiment, the staining solution further comprises one or more OSRs.

In one embodiment of the invention, the concentration of dye in the staining solution is from about 0.1 μM to about 1.0M; from about 0.1 μM to about 1000 μM; from about 100 μM to about 500 μM; from about 200 μM to about 500 μM; from about 300 μM to about 450 μM; about 350 μM; about 400 μM; or about 450 μM.

The pH of compositions comprising magnetic particles of the invention may be maintained at any of a range of pHs suitable for the particular process and sperm type. In certain embodiments, this will be in the range of about 5.0 to about 9.0; in the range of 5.5 to about 7.8; from about 5.0 to about 7.0; from about 6.0 to about 7.0; from about 6.0 to about 6.5; from about 6.0 to about 8.0; from about 6.5 to about 7.5; from about 6.8 to about 7.4; from about 7.0 to about 9.0; from about 7.0 to about 8.0; from about 7.0 to about 7.5; about 6.2, about 6.5; about 6.6; about 6.7; about 6.8; about 6.9; about 7.0; about 7.1; about 7.2; about 7.3; about 7.35; about 7.4; or about 7.5; about 7.6, about 7.7, about 7.8, about 7.9; or about 8.0.

In certain embodiments, magnetic particles may be combined with a sperm sample to form a sperm composition. The term "sperm sample" may comprise a processed semen sample or an unsorted, conventional semen sample. In some embodiments of the invention, the sperm composition comprising magnetic particles is used to process sperm for use in ART. Such ART techniques involve different levels of gamete cell processing which in the case of sperm can entail, by example only and is not limited to one or more of the following: artificially collecting a semen sample from the male animal that may involve natural, electronic or other types of sexual stimulation; holding; transporting; buffering with different pHs; chilling; warming; staining; diluting; concentrating; energetically exciting as with a laser; electronic charging; deflecting; ablating to kill unwanted cells usually with targeted lasers; sorting; collecting; shaking; oscillating; magnetically separating; oxygenating as associated with microchip sorting procedures; labeling; precipitating; centrifuging; resuspending; mixing; dialyzing; cryostabilizing; freezing; vitrifying; cryopreserving; thawing; culturing; inseminating; microinjecting; microfluidic processing; microchip processing; jet and air processing; flow cytometry processing; and similar handling techniques. Whereas a single processing step may exert only minimal stress on a sperm, others or a combination may add significant stress, often killing the cell. An example is the sex sorting process used to separate X- from Y-chromosome bearing cells; the sorting process combines a large number of independent stressful steps that may compromise the overall integrity of the sorted sperm population.

In some embodiments of the invention, a sperm composition comprising a sperm sample and magnetic particles can be used immediately or processed within the first few minutes after the magnetic particles are added to the sperm sample for whatever processing step is needed, whereby the holding period would be in the range of 1 to 2 seconds; 1 to 10 seconds; 1 to 20 seconds; 20 to 30 seconds; 30 seconds to 1 minute; 1 to 2 minutes; 1 second to 3 minutes; 1 minute to 5 minutes; or 1 minute to 10 minutes. In other embodiments, holding periods can be longer, as in the range of a 1 minute to 15 minutes, the range of 15 minutes to 1 hour or up to about 8 hours or overnight for extensive processing such as with sex sorting techniques.

In some embodiments of the invention, magnetic particles are used several times during a complex processing procedure. In other embodiments, magnetic particles are used only at one or more particular steps. By way of example, magnetic particles can be used during the staining process during sex sorting, which is often performed at non-physiological pH and at elevated temperatures. Similarly, magnetic beads can be used just prior to cryopreservation of sperm or after thawing of cryopreserved sperm.

A further embodiment of the present invention provides a method of improving the motility, viability and/or fertility of a sperm sample that has already undergone a sorting process, including but not limited to sex sorting, comprising the step of contacting or adding a sorted sperm sample to magnetic particles and then subsequently removing the magnetic particles.

Another broad object of the present invention is to improve the motility, viability (including longevity and ability to survive environmental stress) and fertility of processed and/or sorted sperm for use in ART such as IVF, AI, ICSI (as well as other techniques using enucleated cells), and MOET (as well as other embryo transfer techniques). Some embodiments of the invention encompass compositions comprising magnetic particles comprising a sorted or processed sperm sample, and optionally at least one OSR in the range of 0.01 mg/ml to 5 mg/ml, for use in ART.

A further embodiment of the invention resides in a method of making an embryo comprising mixing at least one egg with one or more sperm from a sperm sample that has been contacted with magnetic particles. The embryos produced by this method constitute a further embodiment of the invention.

Another embodiment of the invention includes a method for inseminating an organism through an AI technique using a processed or sorted sperm sample contacted with magnetic particles. The progeny of the organism that results from the aforementioned AI method also constitutes an embodiment of the invention. A further embodiment of the invention encompasses a method for recovering embryos that are produced from the aforementioned AI method.

Embodiments of the invention can include sperm, or spermatozoa, collected from numerous species of male animals, and the invention should be understood not to be limited to the species of male animals described by the specific examples within this application. Rather the specific examples within this application are intended to be illustrative of the varied and numerous species of male animals from which semen can be collected and utilized in certain embodiments of the invention. Embodiments of the invention, for example, may include the sperm of humans as well as animals having commercial value for meat or dairy production such as swine, ovine, bovine, equine, deer, elk, buffalo, or the like (naturally the mammals used for meat or dairy production may vary from culture to culture). It may also include the sperm of various domesticated mammalian species encompassed by canines and felines, as well as sperm of primates, including but not limited to chimpanzees, gorillas, or humans and the spermatozoa from whales, dolphins and other marine mammals. It may also include frozen-thawed sperm from all the various mammals above-described and further, including but not limited to, the sperm of deceased donors, from rare or exotic mammals, zoological specimens, or endangered species.

A particular embodiment of the invention comprises a method of sorting a sperm sample to form one or more subpopulations comprising the steps of providing a sperm sample, sorting the sperm sample to form one or more subpopulations and using magnetic particles during one or more of the aforementioned sorting steps. In the context of sorting sperm using a flow cytometer, for example, magnetic particles may be used in a diluent for diluting sperm, a staining solution for staining the sperm with, for example, a DNA selective dye, a sheath fluid for encapsulating the core stream containing the sperm as it passes through the flow cytometer, a catch media for receiving one or more of the sorted sperm subpopulations, or a resuspension media for resuspending processed sperm.

Another embodiment of the invention encompasses a composition comprising a gender enriched sperm population, created for example by way of separation or photo/laser ablation, and magnetic particles.

Another embodiment of the invention encompasses a method of processing sperm comprising the steps of forming a composition comprising said sperm and magnetic particles; removing said magnetic particles from said composition; forming a stream comprising said sperm; determining a property of said sperm in said stream; and selecting sperm having a property of interest from said sperm in said stream. In a further embodiment, the steps of forming a composition comprising said sperm and magnetic particles and removing said magnetic particles from said composition are performed after the step of selecting sperm having a property of interest from said sperm in said stream. In yet another embodiment, the steps of forming a composition comprising said sperm and magnetic particles and removing said magnetic particles from said composition are performed before the step of forming a stream comprising said sperm. In a further aspect of the invention, magnetic particles that have been removed from a composition comprising sperm are washed one or more times in a suitable media in order to extract any viable and/or uncompromised sperm that may have adhered to the particles.

BRIEF DESCRIPTION OF THE DRAWINGS

In order that the invention may be more clearly understood, various embodiments of the present invention will now be described by way of example only with reference to the accompanying sheets of drawings wherein:

FIG. 2 shows the results of ICP and Zeta analysis of multiple lots of magnetic particles.

FIG. 3 shows various sort parameters and percentage of dead sperm removed by magnetic particles in Example 2.

FIG. 4 shows the percentage of dead sperm removed by magnetic particles in Example 2.

FIG. 6 shows various sort parameters and percentage of dead sperm removed by sonicated and non-sonicated magnetic particles in Example 2

FIG. 7 shows the percentage of dead sperm removed by sonicated and non-sonicated magnetic particles in Example 2.

FIG. 17 shows 0- and 3-hour post-thaw motility of sperm treated with magnetic particles in Example 6.

FIG. 19 shows quality control analysis results for 8 bulls used in Example 7.

FIG. 23 shows post-thaw motility and viability of sperm treated with magnetic particles in Example 7.

FIG. 24 shows IVF trial results using sperm treated with magnetic particles in Example 7.

FIG. 28 shows the percentage of dead sperm removed by magnetic particles in Example 11.

FIG. 29 shows various sort parameters and percentage of dead sperm removed by magnetic particles in Example 12.

FIG. 30 shows the percentage of dead sperm removed by magnetic particles in Example 12.

FIG. 31 shows the percentage of dead sperm removed by magnetic particles in Example 13.

FIG. 32 shows the percentage of dead sperm removed by magnetic particles in Example 13.

FIG. 33 shows the percentage of dead sperm removed by magnetic particles in Example 14.

FIG. 34 shows the percentage of dead sperm removed by magnetic particles in Example 14.

FIG. 35 shows various sort parameters in Example 15.

FIG. 36 shows the percentage of dead sperm removed by magnetic particles in Example 15.

FIG. 37 shows post-thaw motility and viability of sperm treated with magnetic particles in Example 15.

FIG. 38 shows various sort parameters and percentage of dead sperm removed by magnetic particles in Example 15.

FIG. 39 shows the percentage of dead sperm removed by magnetic particles in Example 15.

FIG. 40 shows the percentage of dead sperm removed by magnetic particles in Example 15.

FIG. 41 shows post-thaw motility and viability of sperm treated with magnetic particles in Example 15.

FIG. 42 shows IVF trial results using sperm treated with magnetic particles in Example 15.

DETAILED DESCRIPTION OF THE INVENTION

Figure 1:
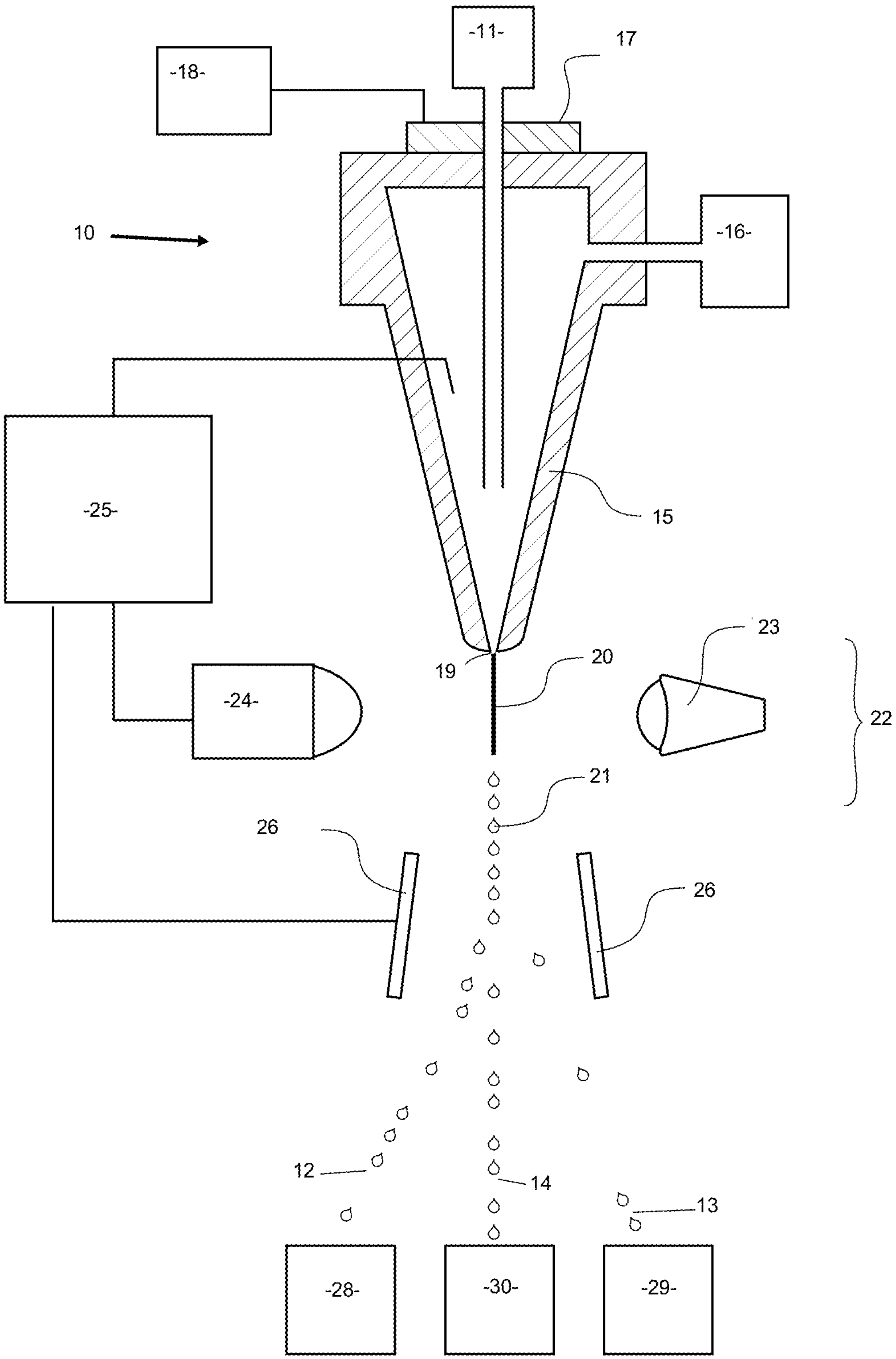
FIG. 1 is a schematic representation of part of a flow cytometer illustrating a method of sorting a sperm sample into one or more subpopulations according to some embodiments of the present invention.
Figure 5:
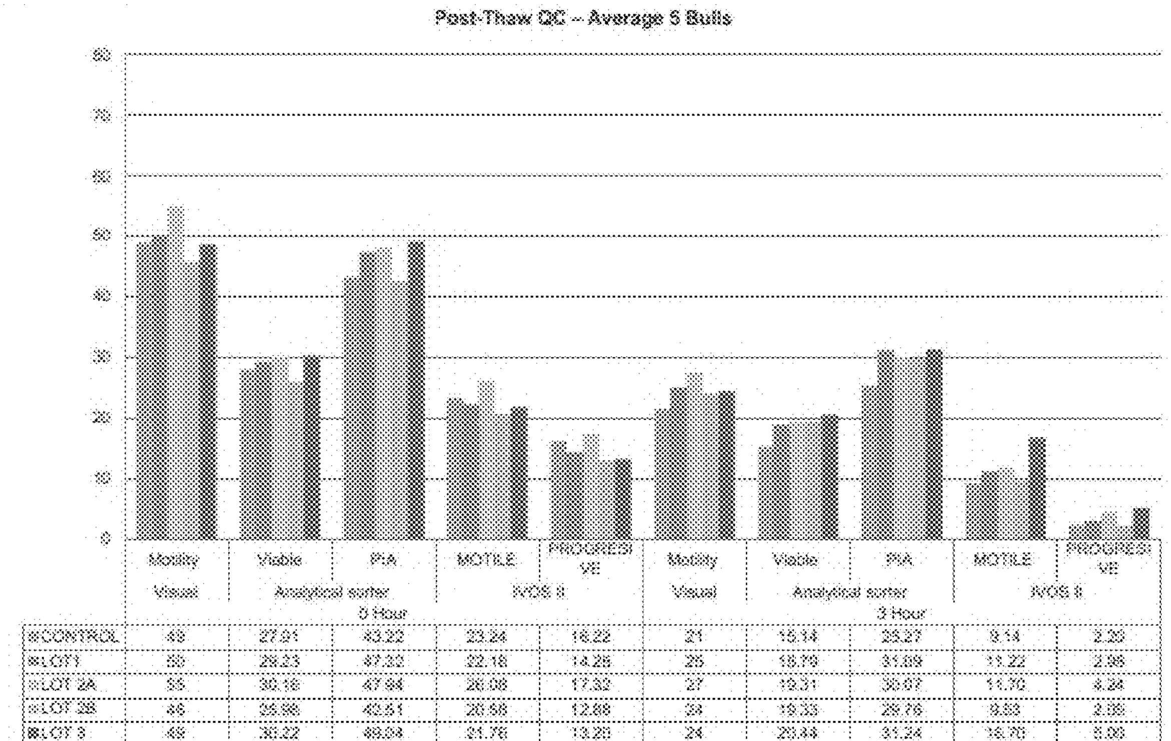
FIG. 5 shows post-thaw motility and viability of sperm treated with magnetic particles in Example 2.

The invention broadly encompasses methods and compositions comprising magnetic particles for processing sperm. It has been discovered that the use of magnetic particles for processing sperm improves the relative number of viable and/or uncompromised sperm relative to dead and/or compromised sperm in a sample, as well as the overall quality of the processed sperm, including but not limited to increased motility, viability and fertility. Furthermore, by decreasing the number of dead and/or compromised sperm in a sample prior to sex sorting, the overall speed and efficiency of the sex sorting process can be increased. The net result is higher quality, lower cost gender enriched sperm that can be used in ART.

Briefly described, embodiments of the described methods and processes include a method for removing or identifying cells or cellular structures having damaged membranes from those with intact membranes, thereby enriching sample, or cellular, viability and quality. The method may be applied to cells such as contained in freshly collected samples, after dilution, during and after cooling, or during and after other cell or system procedures that may be employed prior to, or after, cryopreservation, or to frozen/thawed cell samples. The method may also be used for samples that may be used immediately. The method may also be used for samples that may be held for a period of time or extended in buffers or other substances. For example, the method may also be used for samples that may be held at 4° C. to 40° C. for at least about 12, 24, 30, 36, 48, 60, 72 hours or more. The method may also be used for samples that include but are not limited to samples that have an osmolarity of 250-375 mOsm. The enriched cell populations may be used for routine procedures, prior to or after other processing techniques, prior to or after shipment of samples, and prior to or after long-term cryopreservation or other processes.

Embodiments related to sperm may include a method for removing sperm having damaged membranes from those with intact membranes to enrich sperm viability of a sperm sample. The method may be applied to sperm contained in freshly collected neat ejaculates, after dilution, during and after cooling, or during and after other semen processing procedures that may be employed prior to, or after, cryopreservation, or to frozen/thawed sperm. The method may also be used for neat or extended sperm samples to be used immediately. The method may also be used for neat or extended sperm samples held up to 30 h at 4° C. to 40° C., or extended in sperm rich buffers that have an osmolarity of 250-375 mOsm. The enriched sperm populations may be used for routine artificial insemination, prior to or after sperm sexing techniques, prior to or after shipment of semen for routine or sperm sexing purposes or cryopreservation purposes, or for in vitro fertilization, for all mammalian sperm.

In some embodiments, damage to the membranes of intact cells may be reduced by removing known harmful effects caused by damaged cells. For example, DNA fragmentation, oxidative damage caused by peroxidation, and the premature release of proteolytic and hydrolytic enzymes may be examples of effects attributable to membrane damage. Damage to cell sample integrity may reduce lifespan both in vitro and in vivo, may reduce desired cellular functional ability, and may cause poor resultant capabilities.

With respect to sperm as one, non-limiting example, damage to the membranes of intact sperm may be reduced by removing known harmful effects caused by damaged sperm. For example, DNA fragmentation, oxidative damage caused by peroxidation, and the premature release of proteolytic and hydrolytic enzymes may be examples of sperm damage caused by membrane damaged sperm. Damage to spermatozoal integrity may reduce sperm lifespan both in vitro and in vivo, may reduce fertilization ability, and likely causes poor embryo quality, which may be a major source of infertility in mammals.

Mammalian sperm with good fertility may exhibit a high frequency of morphologically-normal, viable sperm. Current procedures for semen processing for sex selection, cooling, or cryopreservation may have detrimental effects on the metabolism and motility of sperm, as well as on the status of sperm membrane domains. The net result of these effects may be reduced sperm functionality. Magnetic removal of damaged or compromised cells or cellular structures may reduce a detrimental effect on the quality of live and normal sperm that may be caused by dead and abnormal sperm.

In various embodiments, the described processes and methods may be used to differentiate necrotic, apoptotic, and normal cells. In the example discussed, the carboxyl modified silane surface binds to the membrane of the dead and dying sperm through an electrical charge interaction known as zeta potential. Material may spontaneously acquire a positive or negative surface electrical charge when brought into contact with a polar medium (e.g., water). For example, an interface in deionized water may be negatively charged. An ionization of surface groups to form a surface electrical charge may be observed with metal oxide surfaces (M-OH) as well as materials that may contain carboxyl and/or amino groups, such as proteins, ionic polymers, and polyelectrolytes. Ionization and/or dissociation, degree of charge development, net molecular charge, and sign, either positive or negative, may depend on the pH of the surrounding medium.

The conjugation of carboxyl group functional magnetic particles may additionally be applied to, for example, fluorescent stains. SYBR®-14 and bis-benzimide are example membrane permeable stains that may be used to distinguish cells from other background substances. In the sperm cell embodiment, such fluorescent stains may distinguish sperm cells from diluent particles frequently found in extenders employed in non-frozen storage or cryopreservation of sperm. Other examples of fluorescent probes may include JC-I and rhodamine 123, which may be used to assess the respiration rate of cell mitochondria; or fluorescently labeled agglutins from the pea (PSA) or peanut (PNA) that may be used to detect acrosome-reacted cells such as sperm. Other labels include but are not limited to acridine orange (e.g., to remove apoptotic cells); 7-aminoactinomycin D (7-AAD), which may be also a DNA intercalating agent in double stranded DNA with a high affinity for GC rich regions; food coloring such as Allum Red (FD&C Red #40), Sunset Yellow (FD&C Yellow #6), Indigo carmine (FD&C Blue #2), and Fast Green FCF (FD&C #3).

In some embodiments of the described methods and processes, cells with varying degrees of membrane damage may be labeled with magnetic particles containing a charged surface. This may be in contrast to the use of annexin-V/microbead magnetic cell sorting procedures that fail to identify and/or remove pre-capacitated or acrosomal reacted sperm because the PS does not become externalized in these examples. When membrane damaged sperm or cellular structures labeled with the surface charged magnetic particles are placed in a magnetic field, such cells or cellular structures may be eliminated from the general population. The resultant harvested sub-population of viable cells, perhaps such as sperm, may be further processed for cryopreservation, non-frozen transport and storage, functional utilization (such as sex selection for sperm), or used in related aspects, perhaps such as assisted reproductive technologies (ARTs) for sperm or the like.

Embodiments of the described methods and processes may be used with any type of magnetically identifying separating apparatus, including but not limited to devices incorporating columns, such as magnetic-activated cell sorting (MACS) products, devices using simple magnetic fields applied to test tubes or containers, or high throughput magnetic devices.

Targeted dead and dying cells labeled with magnetic particles and subjected to magnetic cell separation in an open, column-less magnetic system may be removed more efficiently and in greater numbers per time unit compared to flow cytometry. Magnetic cell separation may be utilized with no internal operating pressure, or if pressurized, a lower internal operating pressure; and the stream of fluid containing the cells may avoid being broken into cell damaging droplets as for flow cytometry. Further, the sheath fluid for flow cytometry may be generally a salt-based, lipoprotein-deficient physiological medium. Magnetic cell separation may allow some cells, such as sperm, to be bathed in nutrient-rich buffers that may promote and prolong cell viability during the separation procedure.

The described methods and processes may remove necrotic cells or cellular structures that have been traumatized during cell processing procedures such as cryopreservation, centrifugation, and staining. Necrotic damage may occur by different cellular processes than that caused in one example by sperm senescence, which may be a naturally occurring cause of cellular death.

In other magnetic cell separation applications, embodiments of the described methods and processes may be used to label cells uniquely, such as sperm, with one or more fluorochrome stains, targeting a specific cell or sperm attribute. The targeted cell or sperm cell may be selectively killed or rendered non-functional, with an energy source, including but not limited to an electrical charge or pulse of laser light. The described methods and processes may be used to magnetically label and ultimately remove the non-functional cell or sperm through magnetic cell separation procedures. The resultant desired sub-population of harvested cells may be selected for membrane intactness (viability) as well as for specific cellular attributes, including but not limited to, in the sperm example, chromosomal sex selection.

In various embodiments, a composition for magnetic cellular manipulation is provided. The composition may include a plurality of particles. Each particle in the plurality of particles may include a magnetic substrate. The magnetic substrate may be characterized by a magnetic susceptibility greater than zero. Each particle in the plurality of particles may also include a chargeable silicon-containing compound. The chargeable silicon-containing compound may coat at least a portion of the magnetic substrate.

"Magnetic susceptibility" means the response of a sample, such as the magnetic substrate, to an externally applied magnetic field. For example, a magnetic susceptibility of less than or equal to zero may be associated with diamagnetism. A magnetic susceptibility of greater than zero may be associated with magnetic properties other than diamagnetism. For example, in various embodiments, the magnetic substrate may be characterized by one or more of paramagnetism, superparamagnetism, ferromagnetism, or ferrimagnetism. The magnetic substrate may include a metal oxide, such as a transition metal oxide, for example, an iron oxide. In some examples, the magnetic substrate may include $Fe_3Q_4$.

A "chargeable silicon-containing compound" is any silicon containing molecule, polymer, or material that may be caused to acquire or hold a charge, e.g., via functionalization with charged or chargeable moieties. Chargeable/charged moieties may include, but are not limited to, species (and ions thereof) of: metals; oxides; carboxylates; amines; amides; carbamides; sulfates; sulfonates; sulfites; phosphonates; phosphates; halides; hydroxides; and combinations thereof. For example, the chargeable silicon-containing compound may include 2-(carbomethoxy)ethyltrimethoxysilane.

In various examples, the composition may include a zeta potential charge. For example, the chargeable silicon-containing compound may include a negative zeta potential charge. The chargeable silicon-containing compound may include a positive zeta potential charge. In some examples, at least a portion of the plurality of particles may include a first zeta potential charge. The portion of the plurality of particles may form a complex with one or more cells or cellular structures that include a second zeta potential charge. The second zeta charge may be opposite in sign compared to the first zeta charge. In several embodiments, at least a portion of the plurality of particles may include a negative zeta potential charge. The portion of the plurality of particles may form a complex with one or more sperm cells or sperm cellular structures that include a positive zeta potential charge.

In another embodiment, a method for magnetic cellular manipulation is provided. The method may include contacting a composition with a biological sample to form a mixture. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate. The biological sample may include cells and/or cellular structures. The method may also include applying a magnetic field to the mixture to manipulate the composition.

A "biological sample" may include any natural or prepared composition that includes the cells and/or cellular structures. Natural samples may include, for example, biological fluids containing cells or cellular structures, such as blood, lymphatic fluids, intestinal fluids, intercellular fluids, sweat, tears, urine, semen, mucosal secretions, synovial fluid, and the like. Natural samples may include fluids typically free of cells or cellular structures, but which may include cells or cellular structures as part of injury, illness, genetic defect, or other pathological conditions. Prepared samples may include any biopsy, tissue homogenate, or other prepared form of biological tissue. Typically, the biological sample will include at least one cell or cellular structure characterized by a zeta potential charge. The biological sample may include at least two or more cells or cellular structures characterized by zeta potential charges differing in sign or charge density. For example, a biological sample may include a first cell characterized by a first zeta potential charge and a second cell characterized by a second zeta potential charge opposite in sign to the first zeta potential charge.

In some embodiments, the method may include causing the chargeable silicon-containing compound to acquire a first zeta potential charge. The first zeta potential charge may be opposite in sign compared to a second zeta potential charge comprised by the cells and/or cellular structures in the biological sample. Causing the chargeable silicon-containing compound to acquire the first zeta potential charge may include contacting the chargeable silicon-containing compound to a polar medium, as described herein.

In several embodiments, the method may include causing the composition and at least a portion of the cells and/or cellular structures in the biological sample to form a complex.

Applying the magnetic field to the mixture to manipulate the composition may manipulate the complex.

In some embodiments, at least a portion of the plurality of particles further comprises at least one of a protein, an antibody, and a dye.

In several embodiments, the biological sample may include viable cells and damaged or compromised cells or cellular structures. The composition may selectively form a complex with one of the viable cells or the damaged or compromised cells or cellular structures, for example according to a first zeta potential charge on the composition and an opposite second zeta potential charge on one of the viable cells or the damaged or compromised cells or cellular structures. The method may further include separating the viable cells from the damaged or compromised cells or cellular structures by applying the magnetic field to the mixture. Because the composition may selectively form a complex with one of the viable cells or the damaged or compromised cells or cellular structures, the portion of the biological sample forming the complex with the composition may be magnetically manipulated and separated from portions of the biological sample not forming the complex with the composition. The method may therefore be a method for selectively and magnetically separating portions of the biological sample according to zeta potential charge.

In various embodiments, the biological sample may include viable sperm cells and damaged or compromised sperm cells or sperm cellular structures. The composition may form a complex with the damaged or compromised sperm cells or sperm cellular structures. The method may further include separating the viable sperm cells from the complex including the damaged or compromised sperm cells or sperm cellular structures by applying the magnetic field to the mixture. Because the composition may selectively form a complex with the damaged or compromised sperm cells or sperm cellular structures, the complex with the damaged or compromised sperm cells or sperm cellular structures may be magnetically manipulated and separated from the viable sperm cells. The method may therefore be a method for selectively and magnetically separating viable sperm cells from the damaged or compromised sperm cells or sperm cellular structures according to zeta potential charge.

In several embodiments, the method may include subjecting the sperm sample to detection, for example fluorescence detection as described herein.

In various embodiments, a kit for magnetic cellular manipulation is provided. The kit may include instructions. The instructions may include contacting a composition with a biological sample to form a mixture. The instructions may also include applying a magnetic field to the mixture to manipulate the composition. The kit may also include the composition. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate.

In some embodiments of the kit, the biological sample may include viable cells and damaged or compromised cells or cellular structures. The composition may form a complex with one of the viable cells or the damaged or compromised cells or cellular structures. The instructions may further include separating the viable cells from the damaged or compromised cells or cellular structures by applying the magnetic field to the mixture.

In several embodiments of the kit, the composition may be configured for forming a complex with damaged or compromised sperm cells or sperm cellular structures. The instructions may further include selecting the biological sample comprising viable sperm cells and damaged or compromised sperm cells or sperm cellular structures. The instructions may also include separating the viable sperm cells from the complex including the damaged or compromised sperm cells or sperm cellular structures by applying the magnetic field to the mixture.

Processing steps to which sperm are commonly subjected, and with which the invention may be used before, during or after, include, but are not limited to, collecting from a male animal, which may involve natural, electronic or other types of sexual stimulation; holding; transporting; buffering; chilling; warming; staining; diluting; concentrating; energetically exciting (as with a laser, for example); electronic charging; deflecting; ablating to kill unwanted cells usually with targeted lasers; sorting; collecting; shaking; oscillating; magnetically separating; oxygenating as associated with microchip sorting procedures; labeling; precipitating; centrifuging; resuspending; mixing; dialyzing; cryostabilizing; freezing; vitrifying; cryopreserving; thawing; culturing; inseminating; microinjecting; microfluidic processing; microchip processing; jet and air processing; flow cytometry processing; and similar handling techniques.

Regardless of how sperm are to be ultimately utilized, the initial processing step is typically collection of a sperm sample from a male. Generally, the sperm sample is collected into an extender or diluent designed to sustain the cells until further processing or use. Alternatively, semen is collected and then subsequently diluted with an extender after collection. One embodiment of the invention encompasses processing collected semen with magnetic particles during or subsequent to collection.

Whereas a single processing step, such as collection, may exert only minimal stress on sperm, others or a combination may add significant stress, often killing the cells. An example is the sex sorting process used to separate X- from Y-chromosome bearing cells; the sorting process combines a large number of independent stressful steps that compromise the overall integrity of the sorted sperm population. Accordingly, in a particular embodiment of the invention, compositions comprising magnetic particles are used in the sorting process, including but not limited to the staining solution, sheath fluid and catch media, and prior to and after cryopreservation of such processed cells.

I. Collecting Sperm

It is contemplated that intact viable bovine, porcine, equine, ovine, *cervine*, murine or other mammalian sperm, may be collected and contacted with magnetic particles. Various methods of collection of viable sperm are known and include, for example, the gloved-hand method, use of an artificial vagina, and electro-ejaculation. As an example, a bovine sperm sample, typically containing about 0.5 to about 10 billion sperm per milliliter, may be collected directly from the source mammal, or from more than one source mammal of the same species, into a vessel containing magnetic particles to form a sperm composition. The sperm composition may optionally comprise one or more OSRs, which may be present as constituents of the composition comprising magnetic particles prior to contacting with the sperm, or which may be added to the sperm composition, each OSR in the concentration range of 0.01 mg/ml to 5 mg/ml. The magnetic particles may be subsequently removed from the sperm composition prior to any further processing steps.

Once the sperm composition is in the laboratory, various quality checks can be conducted, including checking the motility (e.g., via CASA System), viability (e.g., via flow cytometer), morphology (e.g., via microscopy) and concentration (e.g., via NucleoCounter). Sperm compositions that pass these quality checks can then be prepared for further processing, such as sorting. A comparison of viewing chambers and slides can be done in a variety of IVOS instruments, which for example only can be a Hamilton-Thome IVOS (Hamilton-Thome, Beverly, MA). Instrument settings may be set as follows: image capture; frames per second=60; number of frames=30; cell detection; minimum contrast=50; minimum cell size=5; defaults, cell size=5; cell intensity=50; progressive cells, path velocity=50 μm/s; straightness 2: 70%; slow cells (um/s); average path velocity (VAP, <30 μm/s), straight-line velocity (VSL, <15 μm/s). The CASA motility variables measured can be a percentage of total motile sperm (motile), percentage of progressively motile sperm (progressive), VAO, VSL, curvilinear velocity (VCL, um/s), average lateral head displacement (ALK, um) and the number of times the sperm head crosses the mean path/s (BCF, Hz), straight-line sperm motility (STR, %), and linear sperm motility (LIN, %). See for instance, Lenz, R W, et al., J AnimSci (2011) 89:383-388, incorporated by reference herein in its entirety.

Various OSRs can be used in the context of the current invention, including but not limited to catalase, superoxide dismutase (SOD), SOD mimics, glutathione, glutathione reductase, glutathione peroxidase, pyruvate, mercaptoethanol, butylated hydroxytoluene (BHT), lipoic acid, flavins, quinines, vitamin K (and related vitamers), vitamin B12 (and related vitamers), with 'vitamers' defined as compounds having the same vitamin activity (such as cobalamin, cyanocobalamin, methylcobalamin, adenosylcobalamin, hydroxocobalamin, and pseudo-B12), vitamin E (including its vitamers, tocopherols (a, 'y), tocotrienols, and α-tocopheryl), alpha-ketoglutarate (also known as α-KG, AKG or oxo-glutarate) and various biological forms of AKG (such as arginine, aspartate, lysine, and similar derivatives), other compounds that regulate nitric oxide in the cell including malondialdehyde (MDA) and asymmetric dimethylarginine (ADMA); and biologically active derivatives thereof.

Alternatively, the semen sample may be collected into an empty vessel and then subsequently contacted with magnetic particles within several minutes to hours after collection to form the sperm composition. In addition to a buffer, the sperm composition may also contain a range of additives, including but not limited to the aforementioned OSRs, chelators, tricarboxylic acid cycle intermediates, cryoprotectants, sterols, lipids, fatty acids, protein sources, antibiotics, growth factors, caproic acid, catalase, Caprogen (caproic acid, catalase, and 5% egg yolk) detergents, including alkyl ionic detergents such as sodiumdodecyl sulfate (SDS). It should be noted that certain substances may be classified in one or more of the above listed categories of additives. For example, citrate may be considered both a tricarboxylic acid cycle intermediate and a buffer.

Exemplary buffers for use in the invention include, but are not limited to, carbonates, phosphates, citrates, acetates, lactates, and combinations thereof. Specific buffers that may be used include, but are not limited to, Tris, TES, Pipes, HEPES, TALP, TCA, PBS, citrate, milk and derivatives thereof, which are discussed in detail in U.S. Pat. No. 7,208,265 the contents of which is hereby incorporated by reference in its entirety.

Exemplary chelators for use in the invention include, but are not limited to, deferoxamine, deferasirox, penicillamine, alpha lipoic acid, DMPS, DMSA, dimercaprol and aminopolycarboxylic acids (complexones), including but not limited to Fura-2, IDA, NTA, EDTA, DTPA, EGTA, BAPTA, NOTA, DOTA and nicotianamine, and derivatives thereof.

Exemplary tricarboxylic acid cycle intermediates for use in the invention include, but are not limited to, pyruvate, acetyl-CoA, citrate, isocitrate, α-ketoglutarate, succinyl-CoA, succinate, fumarate, malate, oxaloacetate, and derivatives thereof, including but not limited to isomers and acids. In a particular embodiment, magnetic particles comprises two or more tricarboxylic acid cycle intermediates, including but not limited to, pyruvate, acetyl-CoA, citrate, isocitrate, α-ketoglutarate, succinyl-CoA, succinate, fumarate, malate, oxaloacetate, and derivatives thereof, including but not limited to isomers and acids.

Exemplary cryoprotectants for use in the invention include but are not limited to propylene glycol, dimethyl sulfoxide, ethylene glycol and glycerol, or a combination thereof. In certain embodiments, magnetic particles may comprise a concentration of cryoprotectant by percent volume (w/v) selected from the following: 1-5%; 5%; 5 to 10%; 10%; 10 to 20%; 16.7%; 20%; 20 to 30%; or 30 to 40%.

Exemplary protein sources for use in the invention include egg yolk, egg yolk extract, milk (including heat homogenized and skim), milk extract, soy protein, soy protein extract, serum albumin, bovine serum albumin, human serum substitute supplement, seminal proteins, such as, for example, whole seminal plasma or seminal plasma extracts (see, for example, Parks et al., Sperm Membrane Phospholipid Peroxidation and Fragmentation: Effects on Sperm Function and Role of Seminal Plasma PAF-Acetylhydrolase, Proceedings of the 16th Technical Conference on Artificial Insemination & reproduction, 1996, the content of which is hereby incorporated herein by reference), and combinations thereof. In certain embodiments, compositions comprising magnetic particles may comprise a concentration of protein source by percent volume selected from the following: 1-5%; 5%; 5 to 10%; 10%; 10 to 20%; 16.7%; 20%; 20 to 30%; or 30 to 40%. Albumin, and more particularly bovine serum albumin (BSA), is a commonly used protein source. For example, if included, BSA may be present in the sperm composition in an amount of, less than about 5.0% (w/v); less than about 2% (w/v); less than about 1% (w/v); or about 0.1% (w/v).

The use of a protein source, such as BSA, alone may initiate the process of capacitation in a percentage of the sperm in the composition. It is generally preferred that this process take place in the female reproductive tract. Therefore, in order to inhibit the initiation of capacitation during dilution, as well as during subsequent processing step such as staining and sorting, an alternative protein source or a protein substitute may be included in the sperm composition. The alternative protein source or protein substitute possess the advantageous effects of a typical protein source, such as BSA, in addition to the ability to inhibit the initiation of capacitation in a larger percentage of the cells in the sperm composition. Examples of alternative protein sources includes human serum substitute supplement (SSS) (Irvine Scientific, Santa Ana, CA) and cholesterol enhanced BSA, while an example of a protein substitute includes a polyvinyl alcohol, such as for example, a low to medium viscosity polyvinyl alcohol generally of a molecular weight of about 30,000 to about 60,000. Generally, if included, these compositions will be present in the same amounts as disclosed above with respect to BSA, with the total albumin content of the buffer or buffered solution generally not exceeding about 5.0% (w/v).

An antibiotic may be included in the sperm composition in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, polymyxin B, or any combination thereof. If included, the antibiotics may be present in a concentration of about 50 μg to about 800 μg per ml of semen, regardless of whether the semen is neat, buffered, or contains additional substances, such as for example, any of the additives mentioned herein. The Certified Semen Services (CSS) and National Association of Animal Breeders (NAAB) have promulgated guidelines regarding the use of antibiotics with respect to sperm collection and use.

A growth factor may be added to the sperm composition in order to help maintain the viability of the sperm. Exemplary growth factors include, for example, transforming growth factors ("TGF"), such as, for example, TGFβ-1 and TGFβ-2, and insulin-like growth factors ("IGF"), such as for example, IGF-1. Generally, TGF may be present in the sperm composition in the form of TGFβ-1 in a concentration of about 0.1 ng/L to about 10 μg/L or as TGFβ-2 in a concentration of about 0.1 ng/L to about 200 ng/L, and IGF may be present in the sperm composition in the form of IGF-1 in a concentration of about 0.1 ng/L to about 50 μg/L. The use of such growth factors is well known in the art and is disclosed, for example, in U.S. Patent Application Publication No. 2003/0157473, the content of which is hereby incorporated herein by reference.

In certain embodiments of the invention, the collection fluid comprises sperm at a concentration of $200 \times 10^7$ cells/ml or less; $100 \times 10^7$ cells/ml or less; $500 \times 10^6$ cells/ml or less; $400 \times 10^6$ cells/ml or less; $300 \times 10^6$ cells/ml or less; $200 \times 10^6$ cells/ml or less; $180 \times 10^6$ cells/ml or less; $160 \times 10^6$ cells/ml or less; $120 \times 10^6$ cells/ml or less; $100 \times 10^6$ cells/ml or less; or $50 \times 10^6$ cells/ml or less. Furthermore, in other embodiments of the invention, the staining solution comprises 0.01-3 mg of magnetic particles per 100 million sperm; 0.1-2 mg of magnetic particles per 100 million sperm; 0.1-2 mg of magnetic particles per 100 million sperm; 0.2-1.8 mg of magnetic particles per 100 million sperm; 0.5-1.6 mg of magnetic particles per 100 million sperm; 0.7-1.5 mg of magnetic particles per 100 million sperm; 1.0-1.4 mg of magnetic particles per 100 million sperm; 1.1-1.3 mg of magnetic particles per 100 million sperm; or 1.125 mg of magnetic particles per 100 million sperm.

Once collected, the sperm may be used, for example, in a staining process, a sorting process, or a fertilization process. If magnetic particles are used in the collection fluid, that may be removed prior to further processing. It is contemplated that any such further use and/or processing of the sperm may utilize magnetic particles.

II. Sorting of Collected Sperm

A Staining of the Cells

One embodiment of the invention encompasses the use of magnetic particles in a staining solution for sperm. A process of staining sperm typically comprises the formation of a staining solution containing intact viable sperm and a dye, sometimes referred to as a label. In this aspect of the invention, the magnetic particles may be contacted with the sperm to form a sperm composition, and then the sperm composition contacted with a DNA selective dye to form the staining solution. Alternatively, a DNA selective dye may be added to a magnetic particles to form a staining solution, with sperm subsequently added to the staining solution.

In this embodiment, the sperm source may be neat semen, or alternatively, a sperm-containing semen derivative obtained by centrifugation or the use of other means to separate semen into fractions.

The pH of the staining solution may be maintained at any of a range of pHs; typically this will be in the range of about 5.0 to about 9.0, or in the range of 5.5 to 7.8. The staining solution may be maintained at a slightly acid pH, i.e., from about 5.0 to about 7.0. Typically, the pH is from about 6.0 to about 7.0; from about 6.0 to about 6.5; about 6.2, about 6.5; about 6.6; about 6.7; about 6.8; about 6.9; or about 7.0. Alternatively, the staining solution may be maintained at a slightly basic pH, i.e., from about 7.0 to about 9.0. Typically, the pH is about 7.0 to about 8.0; about 7.0 to about 7.5; about 7.0; about 7.1; about 7.2; about 7.3; about 7.35; about 7.4; or about 7.5.

The staining solution may be formed by using one or more UV or visible light excitable, DNA selective dyes as previously described in U.S. Pat. No. 5,135,759 and WO 02/41906, the contents of each of which are hereby incorporated herein by reference. Exemplary UV light excitable, selective dyes include Hoechst 33342 and Hoechst 33258. Exemplary visible light excitable dyes include SYBR®-14 and bisbenzimide-BODIPY® conjugate 6-{[3-((2Z)-2-{[1-(difluoroboryl)-3,5-dimethyl-1H-pyrrol-2yl]methylene}-2H-pyrrol-5-yl) propanoyl]amino}-N-[3-(methyl{3-[({4-[6-(4-methylpiperazin-1-yl)-1H,3'H-2,5'bibenzimidazol-2'-yl] phenoxy}acetyl)amino]propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm to an unacceptable degree when used in concentrations which enable sorting or enrichment as described elsewhere.

The staining solution may also comprise a dye quencher in addition to a DNA selective dye. Staining protocols for sex sorting, or even bulk sorting, sperm typically rely upon the inclusion of F&DC red food dye No. 40 ("red food dye No. 40" or "red 40") and/or yellow food dye No. 4 as quenching dyes. The maximal absorbance wavelengths of these quenching dyes overlaps the maximal emissions wavelengths of fluorescent dyes, including Hoechst 33342 when bound to nuclear or chromosomal DNA Because red food dye No. 40 and yellow food dye No. 4 differentially permeate membrane-compromised sperm and overlap the emission spectra of the DNA selective fluorescent dye, FRET (florescence resonance energy transfer) between the light leaving the DNA-stain complex and the dead quenching dye reduces the overall detected intensity of the light emitted from membrane compromised sperm. The quenched, or dampened, fluorescence from these cells provide fewer photons to the detectors resulting in a distinctly lower signal. This distinctly lower signal results in a noticeable separated subpopulation which allows the exclusion ("gating out") of the membrane compromised sperm during the sorting procedure. Since membrane compromised sperm comprises largely non-viable sperm, excluding these cells from the analysis results in an enriched sperm subpopulation with respect to viability in the sex sorted subpopulation.

The staining solution may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., Proc. Natl. Acad. Sci. USA, 15 100(21): 12063-12068 (2003); Gygi, et al., Nucleic Acids Res., 30(13): 2790-2799 (2002); U.S. Pat. Nos. 5,998,140; 6,143,901; and 6,090,947, the content of each of which is hereby incorporated herein by reference.

Fluorescent nucleotide sequences may also be used to label the sperm. Such nucleotide sequences fluoresce when hybridized to a nucleic acid containing a target or complementary sequence, but are otherwise nonfluorescent when in a non-hybridized state. Such oligonucleotides are disclosed, for example, in U.S. Patent Application Publication No. 2003/0113765 (hereby incorporated herein by reference).

Sex specific antibodies may also be used to label the sperm in a staining solution. In this embodiment, for example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the nonfluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

Luminescent, color-selective nanocrystals may also be used to label sperm in a staining solution. Also referred to as quantum dots, these particles are well known in the art, as demonstrated by U.S. Pat. Nos. 6,322,901 and 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207,392 and 6,247,323, each of which is hereby incorporated herein by reference).

In certain embodiments of the invention, the staining solution comprises sperm at a concentration of 500×10$^6$ cells/ml or less; 400×10$^6$ cells/ml or less; 300×10$^6$ cells/ml or less; 200×10$^6$ cells/ml or less; 180×10$^6$ cells/ml or less; 160×10$^6$ cells/ml or less; 120×10$^6$ cells/ml or less; 100×10$^6$ cells/ml or less; or 50×10$^6$ cells/ml or less. Furthermore, in other embodiments of the invention, the staining solution comprises 0.01-3 mg of magnetic particles per 100 million sperm; 0.1-2 mg of magnetic particles per 100 million sperm; 0.1-2 mg of magnetic particles per 100 million sperm; 0.2-1.8 mg of magnetic particles per 100 million sperm; 0.5-1.6 mg of magnetic particles per 100 million sperm; 0.7-1.5 mg of magnetic particles per 100 million sperm; 1.0-1.4 mg of magnetic particles per 100 million sperm; 1.1-1.3 mg of magnetic particles per 100 million sperm; or 1.125 mg of magnetic particles per 100 million sperm.

The concentration of the DNA selective or of any other type of dye in the staining solution is a function of a range of variables which include the permeability of the cells to the selected dye, the temperature of the staining solution, the amount of time allowed for staining to occur, the concentration of sperm, and the degree of enrichment desired in the subsequent sorting or enrichment step. In general, the dye concentration is preferably sufficient to achieve the desired degree of staining in a reasonably short period of time without substantially detrimentally affecting sperm viability. For example, the concentration of Hoechst 33342, Hoechst 33258, SYBR®-14, or BBC in the staining solution will generally be between about 0.1 μM and about 1.0M; from about 0.1 μM to about 1 000 μM; from about 100 μM to about 500 μM; from about 200 μM to about 500 μM; or from about 300 μM to about 450 μM. Accordingly, under one set of staining conditions, the concentration of Hoechst 33342 is about 350 μM. Under another set of staining conditions, the concentration of Hoechst 33342 is about 400 μM. Under still another set of staining conditions the concentration is about 450 μM.

As another example, the concentration of a fluorescent polyamide, such as for example, those described in U.S. Application Publication No. 2001/0002314, will generally be between about 0.1 μM and about 1 mM; about 1 μM to about 1 mM; about 5 μM to about 100 μM; or about 10 μM.

Optionally, the staining solution may also contain additives to enhance sperm quality. Exemplary additives include one or more OSRs, an antibiotic, a growth factor or a composition which regulates oxidation/reduction reactions intracellularly and/or extracellularly as discussed above with respect to cell sample collection. These additives may be added to the collection fluid in accordance therewith.

Once formed, the staining solution may be maintained at any of a range of temperatures; typically, this will be within a range of about 4° C. to about 50° C. For example, the staining solution may be maintained at a relatively low temperature, i.e., a temperature of about 4° C. to about 30° C.; in this embodiment, the temperature is about 20° C. to about 30° C.; from about 25° C. to about 30° C.; or about 28° C. Alternatively, the staining solution may be maintained within an intermediate temperature range, i.e., a temperature of about 30° C. to about 39° C.; in this embodiment, the temperature is at about 34° C. to about 39° C.; about 35° C.; or about 37° C. In addition, the staining solution may be maintained within a relatively high temperature range, i.e., a temperature of about 40° C. to about 50° C.; in this embodiment, the temperature is from about 41° C. to about 49° C.; from about 41° C. to about 45° C.; from about 41° C. to about 43° C.; or about 41° C. Selection of a preferred temperature generally depends upon a range of variables, including for example, the permeability of the cells to the dye(s) being used, the concentration of the dye(s) in the staining solution, the amount of time the cells will be maintained in the staining solution, and the degree of enrichment desired in the sorting or enrichment step.

Uptake of dye by the sperm in the staining solution is allowed to continue for a period of time sufficient to obtain the desired degree of DNA staining. That period is typically a period sufficient for the dye to bind to the DNA of the sperm such that X and Y chromosome-bearing sperm may be sorted or enriched based upon the differing and measurable fluorescence intensity between the two. Generally, this will be no more than about 24 hours; no more 30 than about 10 hours; no more than about 2 hours; no more than about 90 minutes; no more than about 60 minutes; or from about 5 minutes to about 60 minutes. In a particular embodiment, the period is about 30 minutes or about 55 minutes.

The length of the staining period and the temperature at which staining occurs are related such that the longer the period of staining, the lower the temperature of staining temperature may be. For example, in one embodiment, the staining may occur at a relatively low temperature and for a period of about 3 hours to about 24 hours. Alternatively, the staining may occur at an intermediate temperature and for a period of about one half hour to about 3 hours. In addition, staining may occur at a relatively high temperature and for a period of about 10 minutes to about 90 minutes. In a particular embodiment, staining may occur at a temperature of about 4° C. for a period of about 24 hours. In another embodiment, staining may occur at a temperature of about 18° C. for a period of about 4 hours. In yet another embodiment, staining may occur at a temperature of about 41° C. for a period of about 30 minutes. In another embodiment, staining may occur at a temperature of about 35° C. for a period of about 55 minutes. Accordingly, in one embodiment, a staining solution is formed comprising magnetic particles, sperm and a dye in a concentration from about 100 μM to about 450 μM, and the staining mixture is held for a period of time at a temperature of about 28° C.; about 35° C.; or about 41° C. In another embodiment, the period of time is about 30 minutes; about 55 minutes; or about 3 hours.

If magnetic particles are used in the staining solution, it is contemplated that such magnetic particles may be removed prior to any further processing steps. Alternatively, in another embodiment the magnetic particles may remain in the staining solution for further processing including sorting on a flow cytometer.

B. Sorting or Enriching of the Stained Sperm

Some embodiments include use of one or more OSRs as pre-mixed components of the prepared buffers, extenders, stains, catch fluids, and/or cryo-extenders used in the sex sorting procedure. In some cases, when the sorting of sperm is not going to involve sex sorting, a quenching dye without the need for a DNA staining dye may be required, in which case the OSR will only be present with the quenching dye to form the stained sample. Commonly used and well known sorting methods include flow cytometry systems, as exemplified by and described in U.S. Pat. Nos. 5,135,759, 5,985,216, 6,071,689, 6,149,867, and 6,263,745; International Patent Publications WO 99/33956 and WO 01/37655; and U.S. patent application Ser. No. 10/812,351 (corresponding International Patent Publication WO 2004/088283), the content of each of which is hereby incorporated herein by reference. When sorting according to such methods, the sperm are introduced into the nozzle of a flow cytometer in a sample fluid. In one embodiment, the sample fluid may comprise magnetic particles and the stained sperm.

As noted above, in certain embodiments of the invention, sex sorting of sperm may be accomplished using any process or device known in the art for cell analysis, sorting and/or population enrichment including but not limited to use of a flow cytometer or use of a microfluidic chip, and encompasses techniques for physically separating X and Y bearing sperm from each other, as with droplet sorting and fluid switching sorting, and techniques for gender enrichment in which sperm bearing the undesired sex chromosome are killed, immobilized, or otherwise rendered infertile, such as by use of laser ablation/photo-damage techniques.

Generally, in certain embodiments, devices used with the invention determine a property of sperm based on fluorescence emitted by the sperm when passed before a source of illumination such as a laser beam. The presence or absence of X- or Y-bearing chromosomes are examples of such a property. Other properties include but are not limited to viability, motility, intact or damaged membranes, genetic defects, the presence or absence of specific genes or gene markers, morphology and fertility. In certain embodiments, the user decides the property or properties the device will analyze and select for, referred to as a property, or properties, of interest. For example, in one embodiment of the invention, if the property of interest is the presence of a Y-bearing chromosome in sperm, the devices used with the invention can analyze sperm and then select the sperm having the property of interest by, for example, photo-damaging/laser ablating the sperm having the property of interest. Alternatively, the devices used with the invention can photo-damage/laser ablate the sperm without the property of interest, leaving the sperm having the property of interest intact. In other embodiments, the devices of invention can select sperm having the property of interest by isolating the sperm having the property of interest, by for example, separating, or sorting, the sperm having the property of interest from sperm without the property of interest. Devices that may be used with the invention include but are not limited to those disclosed above as well as in US Patent Application Publication No. US 2008/0153087 at paragraphs 23-87; paragraphs 99-148; and FIGS. 1-5; and in U.S. Pat. No. 8,206,987 at column 28, line 17 to column 93, line 35; column 126, line 54 to column 130, line 3; and FIGS. 135-138; the disclosures of which are incorporated by reference herein.

Generally, sheath fluid is used to surround the stream of sample fluid as it travels through a flow cytometer or microfluidic chip. Furthermore, the sheath fluid may be introduced into a nozzle of a flow cytometer using pressurized gas or by a syringe pump. The pressurized gas is often carbon dioxide or nitrogen. In certain embodiments of the invention, a stream containing sperm to be analyzed may be comprised of a sample fluid and a sheath fluid, or a sample fluid alone.

Optionally, the sample fluid or sheath fluid may also contain an additive, such as, one or more OSRs, an antibiotic or a growth factor, as discussed above with respect to cell sample collection. Each of these additives may be added to either fluid in accordance therewith.

One embodiment of a sheath fluid comprises Tris(hydroxymethylaminomethane), sodium-citrate dihydrate and citric acid anhydrous. To prepare this low sugar sheath fluid, regardless of the intended volume of sheath fluid desired, the entire quantity of Tris and sodium-citrate are mixed with approximately 95% of the desired volume of $ddH_2O$. Three quarters of the citric acid is also concurrently added. A titration with the remaining quantity of citric acid is performed to reach a specific pH of 6.80. After pH adjustment, $ddH_2O$ is added until an osmolarity of 300 mOsm is obtained. One or more OSRs may also be added to this sheath fluid, typically in the range of 0.01 to 5.0 mg/ml.

FIG. 1 illustrates, in schematic form, part of a flow cytometer used to sort a sperm composition to form one or more subpopulations, the flow cytometer being generally referenced as 10. In this particular embodiment of the invention, sex sorting is taking place so the subpopulations are X-chromosome bearing sperm and Y-chromosome bearing sperm.

The flow cytometer 10 of FIG. 1 can be programmed by an operator to generate two charged droplet streams, one containing X-chromosome bearing sperm, charged positively, 12, one containing Y-chromosome bearing sperm, charged negatively 13 while an uncharged undeflected stream of dead cells 14 simply goes to waste.

An operator may also choose to program the flow cytometer in such a manner, that both the X- and Y-chromosome bearing sperm are collected using a "high purity sort" (in other words only live X- and Y-chromosome bearing sperm are collected) or to program the flow cytometer to collect both the X- and Y-chromosome bearing sperm using an "enriched sort" (in other words it will collect droplets containing live cells that were not previously sorted and excluding all initial dead cells again by the use of Boolean Gate logic available with the computer that controls the flow cytometer). The Boolean Gate logic can also be used to collect only one of either the X- or Y-chromosome bearing sperm.

Initially, a stream of sperm under pressure, is deposited into the nozzle 15 from the sperm source 11 in a manner such that they are able to be coaxially surrounded by a sheath fluid supplied to the nozzle 15 under pressure from a sheath fluid source 16. An oscillator 17 which may be present can be very precisely controlled via an oscillator control mechanism 18, creating pressure waves within the nozzle 15 which are transmitted to the coaxially surrounded sperm stream as it leaves the nozzle orifice 19. As a result, the exiting coaxially surrounded sperm stream 20 could eventually and regularly form droplets 21.

The charging of the respective droplet streams is made possible by the cell sensing system 22 which includes a laser 23 which illuminates the nozzle exiting stream 20, and the light emission of the fluorescing stream is detected by a sensor 24. The information received by the sensor 24 is fed to a sorter discrimination system 25 which very rapidly makes the decision as to whether to charge a forming droplet and if so which charge to provide the forming drop and then charges the droplet 21 accordingly.

A characteristic of X-chromosome bearing sperm is that they absorb more fluorochrome dye than Y-chromosome bearing sperm because of the presence of more DNA, and as such, the amount of light emitted by the laser excited absorbed dye in the X-chromosome bearing sperm differs from that of the Y-chromosome bearing sperm and this difference communicates to the sorter discrimination system 25 the type of charge to apply to the individual droplets which theoretically contain only a single X- or Y-chromosome bearing sperm. Dead cells (or those about to die) typically absorb the quenching dye which is communicated to the sorter discrimination system 25 not to apply a charge to the droplets containing such cells.

The charged or uncharged droplet streams then pass between a pair of electrostatically charged plates 26, which cause them to be deflected either one way or the other or not at all depending on their charge into respective collection vessels 28 and 29 to form respectively a gender enriched population of X-chromosome bearing and a gender enriched Y-chromosome bearing sperm having a DNA selective dye associated with their DNA The uncharged non-deflected sub-population stream containing dead cells (or those about to die) go to the waste container 30.

Alternatively, the cells of a sperm composition may be sorted or enriched using laser steering. This is often referred to as optical trapping or holographic optical trapping. Generally, tightly focused laser light, such as, for example, light focused by a microscope lens, will have a steep intensity gradient. Optical traps use the gradient forces of a beam of light to trap particles based upon the dielectric constant of the beam. To minimize its energy, a particle having a dielectric constant greater than the surrounding medium will move to a region of an optical trap where the electric field is highest. Such devices and methods are described, for example, in WO 2004/012133, U.S. Pat. No. 6,416,190 and related applications and patents, the content of each of which is hereby incorporated herein by reference. The cells of the sperm composition may be sorted accordingly into separate populations, wherein the spermatozoa of the populations comprises a certain percent X chromosome bearing or Y chromosome bearing sperm. Laser ablation/photo damage or fluid switching may also be used to create gender enriched populations.

Any of the steps of the cell sorting process may be carried out within a temperature range selected from the group consisting of about 5° C. to about 15° C.; about 15° C. to about 20° C.; about 20° C. to about 25° C.; about 25° C. to about 30° C.; about 30° C. to about 35° C.; about 35° C. to about 40° C. and about 40° C. to about 45° C.

Furthermore, it is contemplated that sorted or gender enriched sperm of the invention may comprise at least about 65% X chromosome bearing or Y chromosome bearing sperm, at least about 70% X chromosome bearing or Y chromosome bearing sperm, at least about 75% X chromosome bearing or Y chromosome bearing sperm, at least about 80% X chromosome bearing or Y chromosome bearing sperm, at least about 85% X chromosome bearing or Y chromosome bearing sperm, at least about 90% X chromosome bearing or Y chromosome bearing sperm, at least about 95% X chromosome bearing or Y chromosome bearing sperm, at least about 98% X chromosome bearing or Y chromosome bearing sperm, or at least about 99% X chromosome bearing or Y chromosome bearing sperm.

C. Collection of the Sorted Cells into Catch Media

Once sorted, the sorted cells are collected in a vessel that contains a catch media. Generally, the purpose of the catch media includes providing a fluid support for the cells. In one aspect of the invention, the catch media may comprise magnetic particles. Optionally, the catch media may further comprise any of the additives as discussed above with respect to cell sample collection, including but not limited to one or more OSRs, cryoprotectants, sterols, lipids, fatty acids and protein sources. If included in the catch media, the sterols, lipids, and fatty acids may be, for example, cholesterol.

Exemplary protein sources include milk (including heat homogenized and skim), milk extract, egg yolk, egg yolk extract, soy protein and soy protein extract. Such proteins may be used in a concentration from about 1% (v/v) to about 30% (v/v), preferably from about 10% (v/v) to about 20% (v/v), and more preferably about 10% (v/v).

Optionally, the catch media may also contain additives such as, an antibiotic, a growth factor or one or more OSRs, as discussed above with respect to cell sample collection. Each of these additives may be added to the catch media in accordance therewith.

One embodiment of a catch media is prepared by adding the appropriate amount of egg yolk to media comprising Tris(hydroxymethylaminomethane), sodium citrate dehydrate and citric acid anhydrous, mixing and then allowing the mixture set overnight at 5° C. The following day the mixture is centrifuged at 5000 g for 1.5 h. After centrifugation, the top layer of the supernatant is discarded, and the remaining supernatant, which comprises the low sugar catch media, is collected. One or more OSRs may also be added to the catch media, typically in the range of 0.01 to 5.0 mg/ml. The catch media should then be stored at 5° C. until use. Alternatively, the catch media can be frozen prior to storage and/or shipping. It should be understood that magnetic particles may be added during any of the aforementioned steps for preparing catch media including prior to use, prior to freezing or subsequent to thawing of the media.

Gender enriched sperm may be collected into a vessel containing or coated with a cryoextender comprising magnetic particles, a cryoprotectant and optionally, any of the additives as discussed above with respect to sperm collection. In one embodiment, prior to cryoextension, storage or use of collected sperm, the magnetic particles are removed from the catch media or the cryoextender prior to further processing or cryopreservation of the gender enriched sperm.

D. Cryopreservation of the Sorted Cells

Once the sperm have been sorted and caught in collection vessels, they may be used for inseminating female mammals. This can occur almost immediately, requiring little additional treatment of the sperm. In such an instance, the sperm may be stored in their current state for a period of time necessary to, for example, transport them to the location where the insemination is to take place. The sperm may, therefore, be stored and transported in, for example, the catch media.

Likewise, the sperm may be concentrated to a density appropriate for the particular mammalian species, for example, a density of about $10\times10^6$ sperm/ml to about $120\times10^6$ sperm/ml, and subsequently stored and transported. The selected density depends upon factors such as those discussed below with respect to fertilization, including the species of mammal from which the sperm were obtained. Such a range of densities based upon the species of mammal from which the sperm were obtained are well known to those of skill in the art.

Likewise, the sperm may also be cooled or frozen for use at a later date. In such instances, the sperm may benefit from the addition of a cryoextender to minimize the impact upon viability or post-thaw motility as a result of cooling or freezing.

A protein source may be added to provide support to the sperm. Examples of common protein sources include milk (including heat homogenized and skim), milk extract, egg yolk, egg yolk extract, soy protein and soy protein extract. Such proteins may be found in a concentration from about 3% (v/v) to about 30% (v/v); from about 10% (v/v) to about 20% (v/v); or about 20% (v/v).

A cryoprotectant is preferably included in the cryoextender to lessen or prevent cold shock or to maintain fertility of the sperm. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl®, and combinations thereof. If included, generally, these cryoprotectants are present in the cryoextender in an amount, by percent volume, of about 1-5%; 5%; about 5 to 10%; about 10%; about 10 to 20%; about 16.7%; about 20%; about 20 to 30%; or about 30 to 40%.

Optionally, the cryoextender may also contain additives as discussed above with respect to cell sample collection, including but not limited to an antibiotic, a growth factor, or one or more OSRs. Each of these additives may be added to the cryoextender in accordance therewith.

The following method of freezing porcine sperm can be used with the invention, but is presented by way of example only-any suitable cryopreservation method known in the art can be used.

After sorting, 50 ml tubes containing the sex sorted sperm (each with 20 million cells) can be divided into tubes of 15 ml, with approximately 12 ml of a sex-select sperm sample in each tube, each containing approximately 10 million sex sorted sperm. These tubes can be centrifuged at 3076 g at 21° C. for 4 minutes. The supernatant decanted, and the pellet can remain with some of the supernatant in approximately 50 μl.

To each pellet, a first cooling medium that may comprise a solution of 20% egg yolk and/or lactose can then be added at room temperature. The motility of the sperm can then be checked. If acceptable, the tubes can be taken to a programmable temperature control machine (PolyScience-Mini-Tube) or can be manually handled to decrease the temperature from about 21° C. to about 5° C. over a period of about 2 hours. After the timed temperature shift with the cells at 5° C. a freezing medium is added to the cells, which may comprise egg-yolk, lactose, glycerol and EquexPasteStem, or may just comprise a cryoprotectant such as glycerol, or the cryoprotectant with an osmotic stabilizer which is previously cooled to 5° C. is added to the samples. After 10 minutes, the sex sorted sperm composition can be placed in artificial insemination straws, and the straws then exposed to liquid nitrogen vapors (approximately 4 cm from the liquid nitrogen) for a short period of time (e.g. 10 minutes) or cryopreserved in programmable freezer and then placed directly into the liquid nitrogen for long term preservation.

When gender enriched sperm compositions are ready for use, straws can be unfrozen by thawing/warming the straws (e.g. place in a water bath set at about 37° C. for about 1 minute or 50° for 20 seconds). Post-thaw, motility and viability of the sperm can then be analyzed at 30, 90 and/or 150 minutes for standard comparisons. Magnetic particles can be added to the thawed sperm composition and then subsequently removed prior to any further processing or use in AI.

III. Storage of the Collected Cells

A Storage Period

Once the sperm have been collected from the source male, regardless of whether they are optionally sorted thereafter, the sperm may be stored for a period of time. The period of storage is dependent upon several factors, including for example, the temperature at which the cells are stored, the number of cells within the storage container, whether the sperm are sorted or unsorted or have been previously been subjected to other processes such as cryopreservation, the method of fertilization for which the cells will be used, and the female mammal being fertilized.

Generally, for example, the sperm may be stored for several hours, such as for example, 2, 4, 8, 12, or 24 hours; for several days, such as for example 1, 2, 3, 4, 5, 6, or 7 days; several weeks, such as for example, 1, 2, 3, or 4 weeks; or several months, such as for example, 1, 2, or 3 months. Typically, sperm may be stored for several hours to several days at a temperature of about 0° C. to about 30° C.; for several days to several weeks at a temperature of about −4° C. to about 5° C.; and for several weeks to several months at a temperature of about −196° C. (in liquid nitrogen vapor) to about −4° C. For porcine sperm, for example, a sample can be held at a temperature of 0-39° C. (typically 16-17° C.) for between about 12 hours to about 18 hours while it is being shipped from the collection point to the point of further processing or use. In other embodiments of the invention, the sample can be held at a temperature of 0-39° C. (typically 16-170 C) for more than 18 hours.

It is contemplated that in certain embodiments of the invention, magnetic particles are added to the storage medium and then subsequently removed either before or after the storage period, e.g., prior to use in AI. Magnetic particles may be added and removed to a sperm composition after the storage period and prior to use as well.

B. Storage Temperature

The sperm, whether sorted or unsorted, may be stored at a range of different temperatures. Selection of a storage temperature is dependent upon several factors, such as for example, the length of time for which the sperm will be stored, the concentration of sperm within the storage container, whether the sperm are sorted or unsorted, the method of fertilization for which the sperm will be used, and the female being fertilized. All of these factors affect the number of sperm that will remain viable during the storage period. By way of example, generally the greater the length of time for which the sperm may be stored, the lower the temperature at which the sperm may be stored. In certain species, a decrease in temperature generally permits a greater percentage of the stored sperm to remain viable over a longer period of time. In other species, such as with porcine sperm, this may not be true.

Accordingly, sperm may be stored at a temperature of about −196° C. to about 30° C. For example, sperm may be stored at a relatively low storage temperature, i.e., a temperature range of about −196° C. to about −4° C.; in this embodiment, the temperature is typically from about-12° C. to about −4° C.; from about −10° C. to about −4° C.; or about −4° C. Alternatively, the sperm may be stored at an intermediate storage temperature, i.e., a temperature range of about −4° C. to about 5° C.; in this embodiment, the temperature is typically at about −3° C. to about 5° C.; about 0° C. to about 5° C.; or about 5° C. In addition, the sperm may be stored at a moderately high storage temperature, i.e., a temperature range of about 5° C. to about 30° C.; in this embodiment, the temperature is typically from about 10° C. to about 25° C.; from about 12° C. to about 23° C.; from about 15° C. to about 20° C.; or about 18° C.

C. Storage Container

The sperm composition may be stored in a range of different containers. While the containers may vary in size, generally suitable containers will be capable of containing the sperm composition; that is to say, the containers will be constructed of a material that is not susceptible to leaking or deterioration as a result of contact with fluids generally, and sperm compositions specifically, regardless of whether such contact occurs on the inside or outside of the container. Examples of suitable containers include, for example, flasks, beakers, test tubes, ampules, and other such containers that are generally constructed of glass, plastic, or other similar materials. In a particular embodiment, the container is of a type of construction that is used in the insemination of a female, such as for example, an elongated container. Such elongated containers may generally have a length to diameter ratio of about 1000:1 to about 100:1; a length to diameter ratio of about 900:1 to about 200:1; a length to diameter ratio of about 800:1 to about 300:1; a length to diameter ratio of about 700:1 to about 400:1; a length to diameter ratio of about 600:1 to about 400:1; a length to diameter ratio of about 500:1 to about 400:1; and in one particular embodiment, a length to diameter ratio of about 450:1. Such elongated containers may generally have a volume of 10 about 0.1 cc to about 100 cc, the volume of the container selected to be used being based upon the species of mammal from which the semen was collected. For example, the volume of such elongated containers may be from about 0.1 cc to about 0.7 cc, preferably a volume of about 0.2 cc to about 15 0.6 cc, more preferably a volume of about 0.23 cc to about 0.5 cc, and most preferably a volume of about 0.3 cc to about 0.4 cc.

In a particular embodiment, the elongated container is what is commonly referred to in the artificial insemination industry as a straw, having a volume of about 0.23 cc and a length to diameter ratio of about 133:1. In another particular embodiment, the elongated container is what is commonly referred to in the artificial insemination industry as a straw, having a volume of about 0.5 cc and a length to diameter ratio of about 67:1. Typically containers of these volumes are used for the storage of bovine sperm.

Alternatively, the volume of the elongated containers may be from about lee to about 100 cc; about 10 cc to about 75 cc; about 15 cc to about 50 cc; about 20 cc, to about 40 cc; or a volume of about 25 cc to about 30 cc. In a particular embodiment, the elongated container is what is commonly referred to in the artificial insemination industry as a straw, having a volume of about 25 cc and a length to diameter ratio of about 445:1. Typically, containers of this volume are used for the storage of porcine sperm.

The advantage of storing the sperm composition in a straw is that the composition may remain stored therein until it is to be used for insemination of a female, at which time the contents of the straw may be placed into the uterus of a female.

IV Fertilization or Insemination

Another aspect of the present invention is the fertilization of an egg or insemination of a female, generally employing the novel process for processing and/or storing spermatozoa as described above.

Once a sperm composition has been formed as discussed in greater detail above with respect to the collection and/or processing of a sperm sample, the sperm composition may be used to inseminate a female. Insemination may be performed according to any of a number of ART methods well known to those of skill in the art. These methods include, for example, artificial insemination, including standard artificial insemination, deep uterine insemination and laparoscopic insemination, and other methods well known to those of skill in the art. For example, a sperm composition comprising magnetic particles and one or more OSRs may be used to inseminate a female, such as for example, by artificial insemination. In a particular embodiment, the sperm composition may be in an elongated container for use in the insemination of a female mammal.

Alternatively, the sperm composition may be used to fertilize an egg, and more particularly, an egg in vitro, such as for example, by microinjection, including intracytoplasmic sperm injection (ICSI), and other methods well known to those in the art. The fertilized egg may thereafter be introduced into the uterus of a female by any of a number of means well known to those of skill in the art, such as for example embryo transplant. In another aspect of the invention, zygotes and/or embryos from artificially inseminated females can be recovered and then cultured and/or cryopreserved/vitrified.

Insemination of a female mammal or fertilization of an egg in vitro (followed by introduction of the fertilized egg into the uterus of a female) using a sperm composition may occur shortly after formation of the sperm composition, such as for example, within about 120 hours; within about 96 hours; within about 72 hours; within about 48 hours, and in a particular embodiment, within about 24 hours after formation of the sperm composition. In such instances, generally the sperm compositions may not have been cryopreserved prior to insemination of a female or fertilization of an egg in vitro (i.e., the composition is fresh or comprises fresh sperm) instead it may have been refrigerated at temperatures of about 4° C. to about 25° C.; about 10° C. to about 25° C.; about 15° C. to about 20° C.; or about 18° C. Alternatively, the sperm composition may be cryopreserved and then thawed prior to insemination of a female or fertilization of an egg in vitro (i.e., the dispersion is frozen/thawed or comprises frozen/thawed sperm). Typically, in such an instance, the cryopreserved sperm composition will be thawed immediately, such as, for example, within about 15 minutes, before insemination of a female or fertilization of an egg in vitro. Alternatively, the cryopreserved dispersion may be thawed over a period of time or thawed and subsequently stored for a period of time, such as for example less than about 5 days; less than about 2 days; less than about 1 day; or less than about 12 hours.

Example 1 Particle Preparation for Magnetic Removal of Dead/Damaged Sperm

Magnetic Cores: Magnetic cores may be fabricated such as by co-precipitation of $Fe_3Q_4$ with $Fe_2O_3$ so that the magnetic susceptibility of the particles in a chosen magnetic field may be sufficiently high to provide rapid separation of magnetically labeled cells from non-labeled cells. The core may be comprised of any magnetic material; possible non-limiting examples include: (1) ferrites such as magnetite, zinc ferrite, or manganese ferrite; (2) metals such as iron, nickel, or cobalt; and (3) chromium dioxide. In one embodiment, the iron cores are comprised of magnetite ($Fe_3Q_4$). In other embodiments the core may be extended to include substances such as other iron oxide based nanoparticle materials including composites having the general structure $MFe_2O_4$ (where M may be Co, Ni, Cu, Zn, Mn, Cr, Ti, Ba, Mg, or Pt).

Thus, in this one non-limiting example, a reaction chamber containing 400 mL of $dH_2O$ in a water kettle was warmed to 60° C. To the 400 mL of warmed $dH_2O$, 23.4 g of $FeCl_3 \cdot 6H_2O$ and 8.6 g of $FeCl_2$ or the like was added and the mixture was stirred under $N_2$ gas. To this solution, 30 mL of 25% $NH_3$. $H_2O$ was added and mixing was continued under $N_2$ gas. Almost immediately, the orange salt mixture turned to a dark brown/black solution. The heat was turned off and the ferrofluid slurry was allowed to cool while being vigorously stirred for 30 min. The precipitate was collected magnetically and the supernatant was decanted. To the magnetically collected ferrofluid, 800 mL of $dH_2O$ was added, swirled, and the magnetic collected process was repeated. The washing process was repeated four times to remove substantially all residual $NH_3$. $H_2O$ and any non-magnetic particles. The final wash step may include a solution of 800 mL 0.02 M NaCl in $dH_2O$ or the like. The collected iron core sizes were between approximately 3 and approximately 10 nm.

Coating of Iron Cores with a Functionalizable Surface: The final outer layer may comprise a polymer coat that interacts with the aqueous environment and serves as an attachment site for proteins and ligands. Suitable polymers may include polysaccharides, alkylsilanes, biodegradable polymers such as, for example, poly(lactic acids) (PLA), polycaprolactone (PCL), and polyhydroxybutyrate-valerate (PHBV); composites, and polyolefins such as polyethylene in its different variants. More specifically, polysaccharide chains may include dextrans, arabinogalactan, pullulan, cellulose, cellobios, inulin, chitosan, alginates, and hyaluronic acid. Silicon containing compounds such as alkylsilanes may also be employed to encapsulate the magnetic core. Alkylsilanes suitable for embodiments of the described methods and processes, may include but are not limited to, n-octyltriethoxysilane, tetradecyltrimethoxysilane, hexadecyltriethoxysilane, hexadecyltrimethoxysilane, hexadecyltriacetoxysilane, methylhexadecyldiacetoxysilane, methyl-hexadecyldimethoxysilane, octadecyltrimethoxysilane, octadecyltrichlorosilane, octadecyltriethoxysilane, and 1,12-bis(trimethoxysilyl) dodecane. In one example, the ratio of iron to silicon containing compound coating may be approximately 0.2. In other embodiments, the ratio of iron to silicon containing compound coating may be greater than about 0.2, such as about 0.4 or 0.8, with a view toward completely coating the iron cores such that the iron cores may be removed from the cell suspension within the magnetic field. Undercoated particles may result in the free metal oxide crystals which may be detrimental to cell viability. In still other embodiments, the ratio of iron to silicon containing compound coating may be less than 0.2. Indeed, the iron concentration divided by the silicon containing compound concentration may be from about 0.1 to about 1.

For the examples of magnetic removal of dead/dying or compromised cells such as sperm, a silicon containing compound may be used to encapsulate the iron cores.

The iron core precipitate may be allowed to settle. With the understanding that throughout this disclosure all amounts, times, and values may be varied up or down such as by 10%, 20%, 30%, or even 40% in any permutation or combination for some embodiments, 67.1 mg of the ferrofluid were added to 100 mL of 10% 2-(carbomethoxy) ethyltrimethoxysilane. 2-(carbomethoxy)ethyltrimethoxysilane is yet another example of a silicon containing compound that is suitable for use in the described methods and processes as a silicon containing compound coating. The pH was adjusted to 4.5 using >99.5% glacial acetic acid, and the suspension was reacted at 70° C. for 2 h under $N_2$ gas with vigorous mixing. After cooling, the particles may be magnetically collected and washed with $dH_2O$. After washing, the silane-coated magnetic nanoparticles may be suspended in 5 mL of 0.05 M 2-(N-morpholino) ethanesulfonic acid (MES) Buffer, TRIS Buffer, TALP buffer, or it may remain in the $dH_2O$ until use for separation. The resuspension buffer may be at a pH that retains or creates a net negative zeta potential of the particles.

Iron concentration may be determined using Inductively Couple Plasma-Optical Electron Spectroscopy (ICP-OES), and the iron concentration may be adjusted according to milligrams per milliliter needed for optimal dead cell removal. The particles may have an average hydrodynamic diameter of 300 nm, and need to be in a range of 300 to 1000 nm to stay suspended in solution so that maximum interaction between the cells and particles is achieved by keeping the particles in suspension and not settling out due to larger sizes.

Coupling of proteins and ligands to the particle surfaces: In the event that the surface of the particles needs to be treated and conjugated to a protein or antibody, the following methods may be used. Periodate treatment of dextran and other polymers are one method for the attachment of proteins due largely to the large number of reactive groups that are available for modification. Mild sodium periodate treatment may create reactive aldehyde groups by oxidation of adjacent hydroxyl groups or diols. Proteins, antibodies, streptavidin, and amino-modified nucleic acids may be added at high pH to allow amines to form Schiff bases with the aldehydes. The linkages may be subsequently reduced to stable secondary amine linkages by treatment with sodium borohydride or sodium cyanoborohydride, which may reduce unreacted aldehyde groups to alcohols. Another method of coupling proteins to the magnetic nanoparticles may be to create stable hydrazine linkages. For example, a protein may be coupled to dextran using succinimidyl 4-hydrazinonicotinate acetone hydrazone (SANH; Solulink Inc, San Diego, Calif). The reaction may use five-fold less protein, and the resulting protein density may appear as high as with other methods. The SANH reagent may allow more efficient and gentle coupling of ligands to the dextran surface. Ligand attachment on silica-coated magnetic nanoparticles may be completed using (3-aminopropyl)triethoxysilane (APTS) to introduce amines on the particle surface while (3-mercaptopropyl)triethoxysilane (MPTMS) introduces SH groups. The heterobifunctional coupling agent (Succinimidyl 4-[N-maleimidomethyl]cyclohexane-1-carboxylate) may then be used to link thiols to the amines. As examples, amines on the particle surface may be linked to thiols on streptavidin molecules, and thiols on the particle surface may be linked to amines on streptavidin. There are several methods of crosslinking proteins through chemical modifications known in the art that may be used for the present embodiments of the described methods and processes. For this example, the carboxylic acid functionalized silane may attach proteins and ligands through EDC chemistry.

EDC Activation of COOH groups on Particle Surface Activation: The silanized particles were re-suspended in 0.05 MMES buffer, collected magnetically, and the supernatant may be aspirated and discarded. Another 5 mL of MES buffer (0.05 M, pH 4.7-5.2) per 10 mg of iron was added to the particles and the suspension was vigorously shaken. Particles were magnetically collected, and the supernatant was aspirated and discarded. This step may be repeated two or so additional times. Frozen EDC was allowed to thaw at room temperature for 30 min. EDC (also known as EDAC or EDCI, 1-ethyl-3-(3-dimethylaminopropyl) carbodiimide), commonly obtained as a hydrochloride, is a water soluble carbodiimide, which is typically employed at pH in the range between 4.0 and 6.0. EDC may be used as a chemical crosslinker for collagen, reacting with the carboxylic acid groups of the collagen polymer which may then bond to the amino group in the reaction mixture.

1.6 mg of EDC/mg iron was added to the particle suspension and the suspension was shaken vigorously. Each tube or the like containing particles and EDC was placed on a laboratory rocker at room temperature for 30 min. After 30 min., particles were magnetically collected, and the supernatant was aspirated and discarded. Buffers of varying salt concentrations, molarities, including but not limited to, 0.1 M to 1 M, and pH ranges from 10 to 4.7 may be used for protein conjugation to the various surfaces. The function of each antibody, protein and ligand optimizes at different pH ranges and molarities, as is known in the art (Hermanson, Bioconjugate Techniques, 2008). In this example, the particle pellet was added to 0.05M MES buffer, particles may be magnetically collected, and supernatant may be aspirated and discarded. This step may be repeated three or so times. 10 mg of protein, ligand or stain was suspended in 0.05M MES buffer and added to the particles so that the total labeling volume was about 5 mL per 10 mg of iron.

A stoichiometric balance of 1 mg of protein, ligand, or stain per 1 mg of iron was used for the coupling reaction. Some experiments suggested that the best binding of dead or compromised cells is concentration dependent and may occur at about this concentration (with the above percentage variations applicable, of course). The range in antibody or protein used may include, but is not limited to, 0.125 mg to 5 mg of antibody per mg of iron. Tubes were shaken and placed on a laboratory rocker at room temperature for 24 h, and particles were magnetically collected. The supernatant was aspirated and discarded. Each particle suspension was suspended in 5 mL of MES buffer. To each tube, 5 mL of quenching solution (IM glycine, pH 8.0) was added and the tubes were shaken vigorously. Quenching solutions may include, but are not limited to, 2-mercaptoethanol, ethanolamine, glycine, UV exposure, size exclusion and magnetic collection. Each tube was placed on a laboratory rocker for 30 min. at room temperature. After 30 minutes, 5 mL of wash buffer was added to each tube and shaken to mix. The particles were magnetically separated, and the supernatant was aspirated and discarded. This step may be repeated 4 or so times. After the conjugation process was complete, particles were magnetically collected, washed, and filtered to obtain a size distribution of 50 to 400 nm. After the wash steps, each particle suspension was suspended in a buffer for the particular cells, such as for sperm cells or other such cells, with a pH (6.0-8.0) and osmolarity (250-350) suitable for optimal sperm or other cell viability such as but not limited to TRIS solution, Sodium Citrate solution, TEST solution, egg yolk-TRIS (pH 6.5-7.4), egg yolk-sodium citrate (pH 6.5-7.4), egg yolk-TEST (pH 6.5-7.6), milk extenders (pH 6.5-7.4), commercially available extenders marketed by IMV International, Maple Grove, Minn., USA and MiniTube GmbH, Vernona, Wis., USA and chemically defied media including but limited to TALP (pH 6.0-8.0) Tyrodes (pH 6.0-8.0) and Hepes BGM-3 (pH 6.0-8.0) so that the resultant working iron concentration was about 4 mg/mL as confirmed by Inductive Coupled Plasma-Optical Emission Spectroscopy (ICP-OES).

The particles may be advantageously on the order of about 300 nm so that interaction between the particles and that of the damaged or dead cells is maximized in solution. If particles are too large, such interaction may not occur due to the settling effect of the larger sized particles in solution. If particles are smaller than approximately 30 nm, they may either not be sufficiently magnetic and higher magnetic susceptibility core materials within a chosen magnetic energy field will have to be generated, or these small particles may contribute to nonspecific binding; that is, they may bind to viable cells as well as to dead and dying cells. If nonspecific binding relating to particle size is problematic, particle size may either be increased, or a blocking agent dependent upon the particular cells involved, such as nonfat dried milk or serum albumin for sperm, may be added to the labeling buffer solution to minimize such nonspecific binding.

The surface charged particles are comprised of $Fe_3Q_4$ coated with 2-(carbomethoxy)ethyltrimethoxysilane without further activation or functionalization. The ratio of iron to silicon containing compound coating is approximately 0.2.

Example 2 Removal of Dead Sperm

Three lots of magnetic particles were produced: Lot 1 was the first batch and used for field trial; Lot 2A was similar to Lot 1; Lot 2B was made using less silane per concentration of iron cores that Lot 1 and Lot 2A; and Lot 3 was larger than Lot 2A and 2B combined and had a slightly larger load of iron per L. Also, Lot 3 was sonicated and compared to Lot 3 without sonication.

All lots were sent for ICP and Zeta potential analysis. See FIG. 2.

4

Lot 3 represents a 6 fold scale up of the step of production of magnetite cores and 150 fold scale up from the step of silane coating of cores and magnetic recovery. The scale of Lot 3 produced −20 grams (iron content), which using 1 mg/160 million sperm results in sufficient particles to treat −3000 billion sperm. Assuming an average ejaculate of 10 billion sperm, approximately 300 ejaculates could be processed with 20 grams of magnetic particles. Relatedly, since 50 semen straws can be produced per billion sperm, −150,000 straws could be produced with 20 grams of magnetic particles.

Lots 1, 2A, 2B and 3 were compared for dead removal capacity and Post-Thaw quality control data (e.g., motility, percent intact acrosomes [PIA] and progressive motility).

Procedure

1. Check volume, concentration, motility, morphology and pH of ejaculates from 5 bulls. Add antibiotics.
2. Extend the ejaculates 1:3 with TRIS media, pH 7.30.
3. Centrifuge and adjust concentration to −1200 million sperm per mL.
4. Stain a 20 mL sample in modified TALP (20% yellow no. 6 [Y6] with antioxidants), pH 7.4 at a concentration of 120 Million sperm cells/mL with Hoechst 33342.
5. Wash magnetic particles (2×) with modified TALP, pH 7.4, and concentrate to 20 mg/mL.
6. Divide sample in five 4 mL samples:
   a. Control—keep as it is
   b. Lot 1—add 1 mg of Lot 1 particles for every 160 million sperm
   c. Lot 2A—add 1 mg of Lot 2A particles for every 160 million sperm
   d. Lot 2B—add 1 mg of Lot 2B particles for every 160 million sperm
   e. Lot 3—add 1 mg of Lot 3 particles for every 160 million sperm
7. Incubate for 60 minutes at 34 C.
8. Magnetically remove particles from treated samples.
9. Check concentration of each treated sample.
10. Place samples on the flow cytometer and record parameters. See results in FIGS. 3 and 4.

10. Sex-sort 10 million cells into 3.5 mL of Tris A for each treatment.
11. Place in the cold room and cryopreserve samples.
12. Perform post-thaw QC of each treatment (e.g., 0 and 3 Hour Visual and IVOS Motility, membrane integrity via propidium iodide (PI), and intact acrosomes via peanut agglutinin (PNA)). See results in FIG. 5.

Procedure

Figure 8:
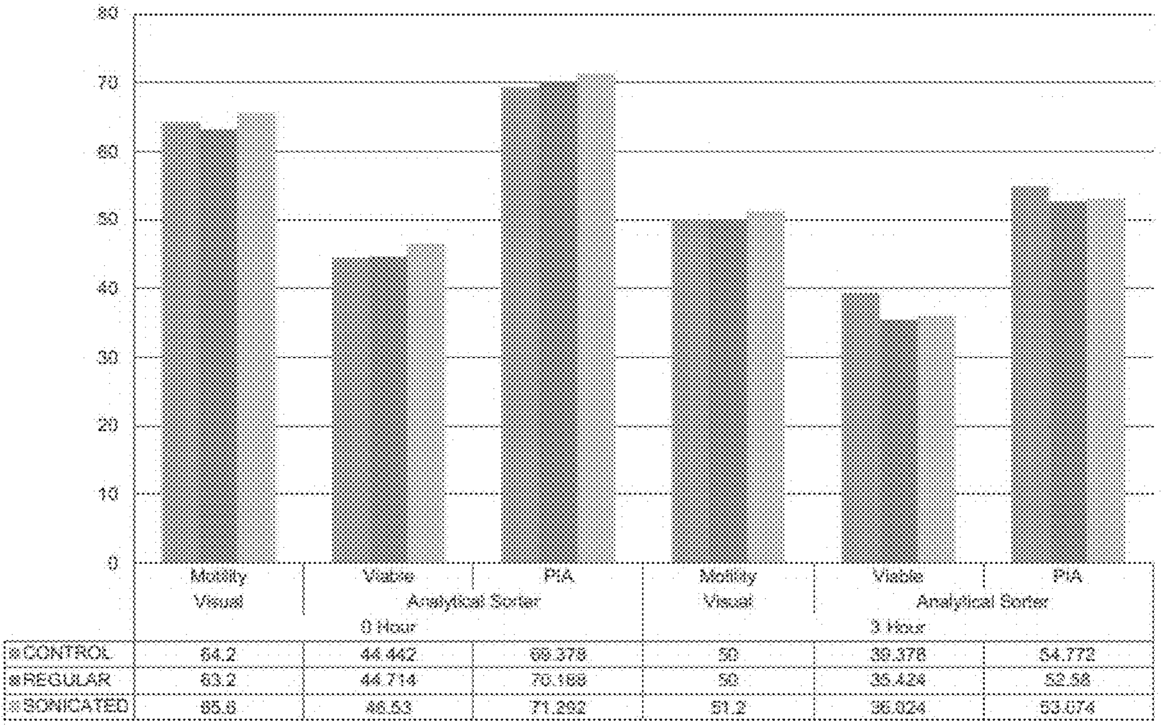
FIG. 8 shows post-thaw motility and viability of sperm treated with sonicated and non-sonicated magnetic particles in Example 2.

1. Check volume, concentration, motility, morphology and pH of ejaculates from 5 bulls. Add antibiotics.
2. Extend the ejaculates 1:3 with TRIS media, pH 7.30.
3. Centrifuge and adjust concentration to –1200 million sperm per mL.
4. Stain $2.4\times10^9$ sperm in 20 mL of modified TALP (20% Y6 with antioxidants), pH 7.4 using Hoechst 33342.
5. Wash magnetic particles (2×) with modified TALP, pH 7.4, and concentrate to 20 mg/mL.
6. Divide sample in five 4 mL samples:
   a. Control—keep as it is
   b. Lot 3 particles—add 1 mg of Lot 1 particles for every 160 million sperm
   c. Lot 3 sonicated particles—add 1 mg of Lot 2A particles for every 160 million sperm
7. Incubate for 60 minutes at 34 C.
8. Magnetically remove particles from treated samples.
8. Check concentration of each treated sample
9. Place samples on the flow cytometer and record parameters. See results in FIGS. 6 and 7.
10. Sex-sort 10 million cells into 3.5 mL of Tris A for each treatment.
11. Place in the cold room and cryopreserve samples.
12. Perform post-thaw QC of each treatment. See results in FIG. 8.

Example 3 Use of Magnetic Particles During Staining

Procedure

Figure 9:
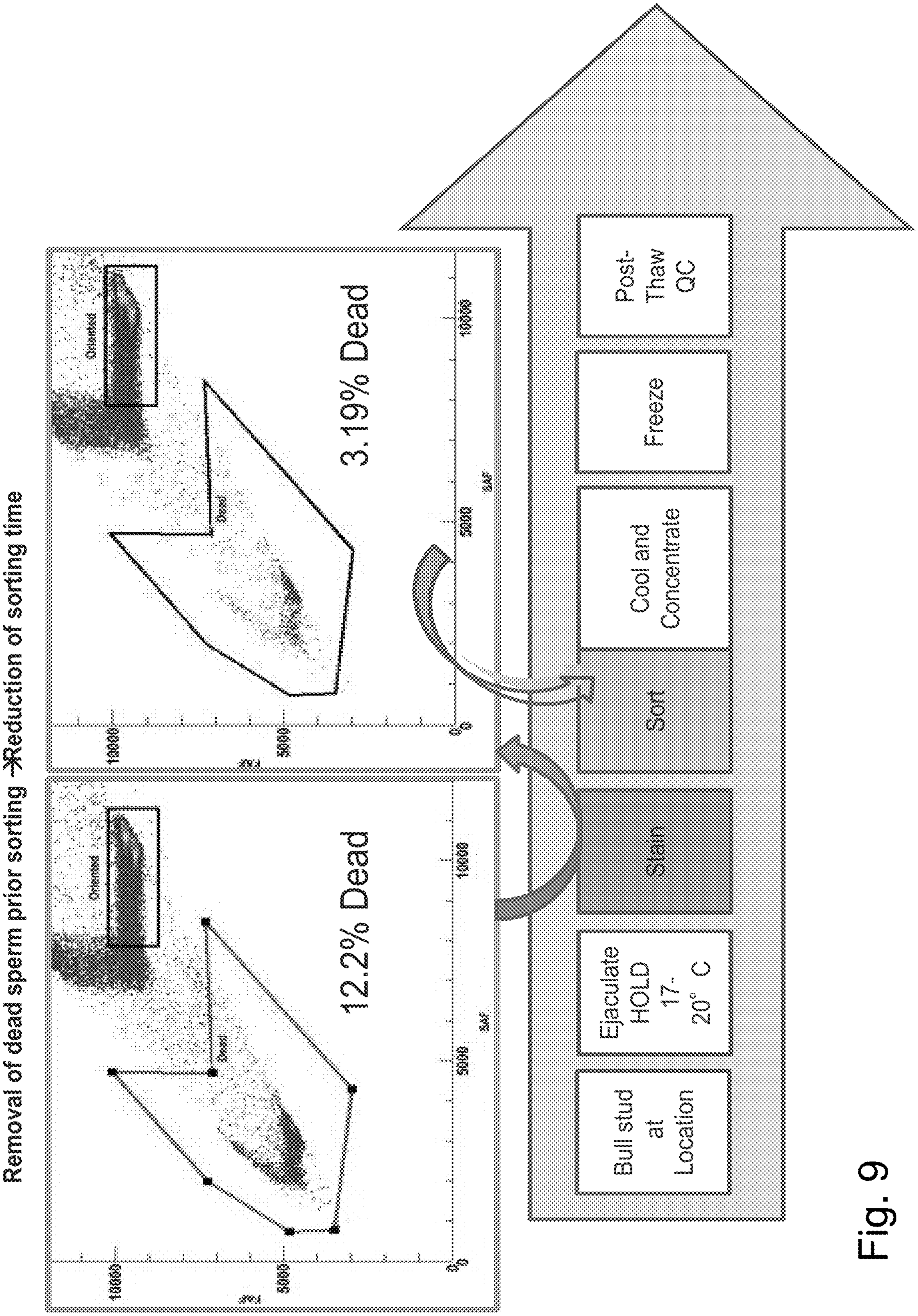
FIG. 9 is a flow cytometer image indicating the percentage of dead sperm removed by magnetic particles.
Figure 10:
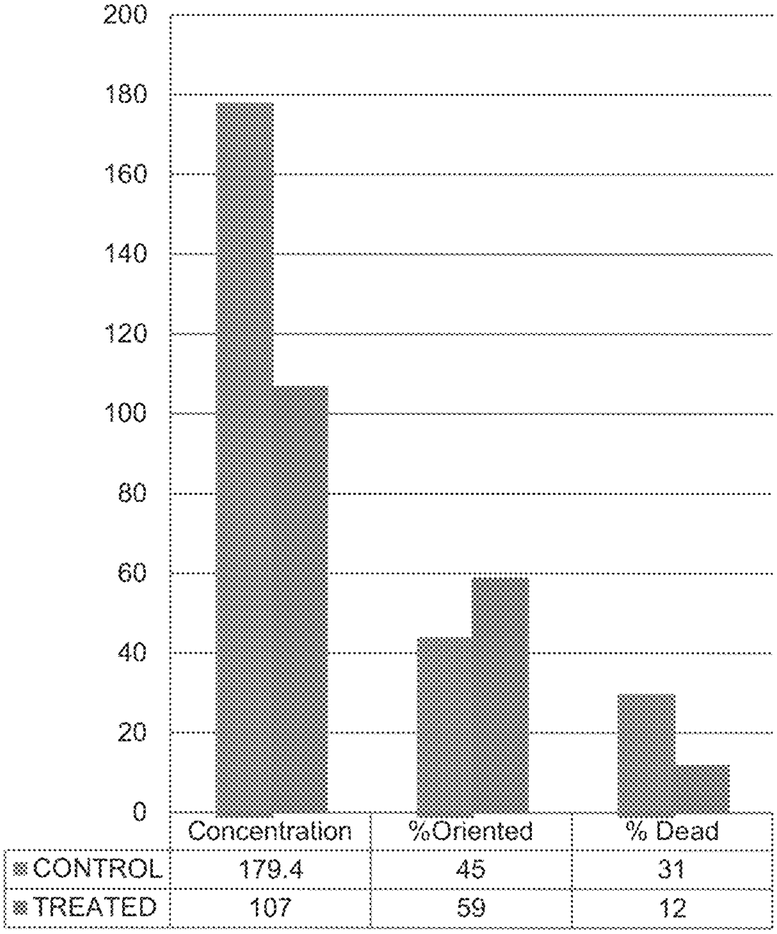
FIG. 10 shows various sort parameters and percentage of dead sperm removed by magnetic particles in Example 5.
Figure 11:
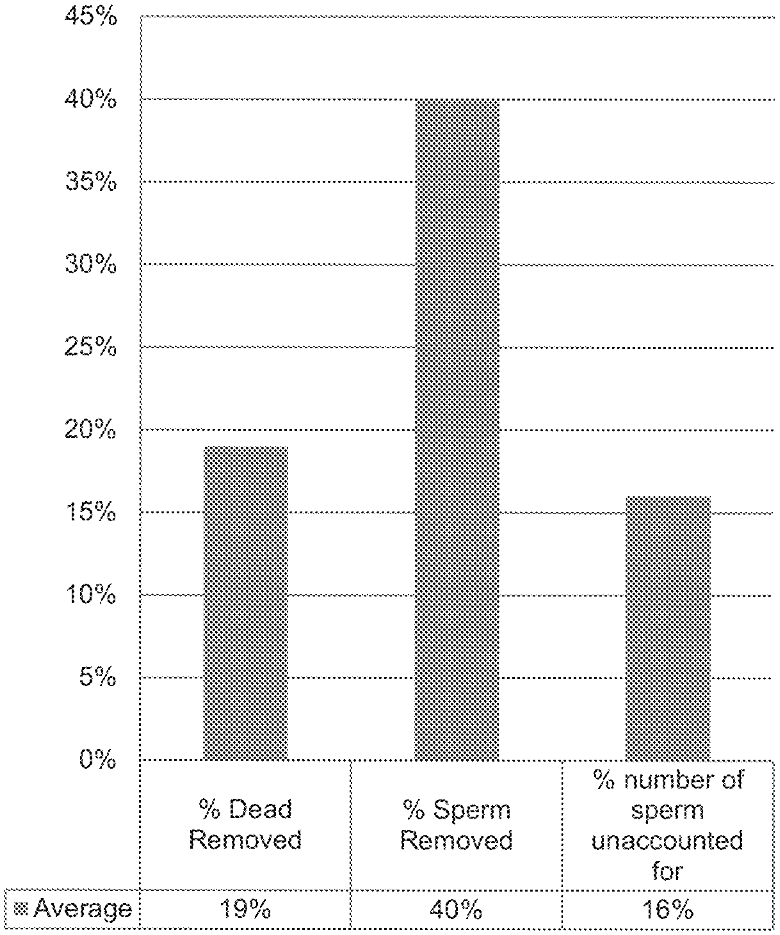
FIG. 11 shows the percentage of dead sperm removed by magnetic particles in Example 5.
Figure 12:
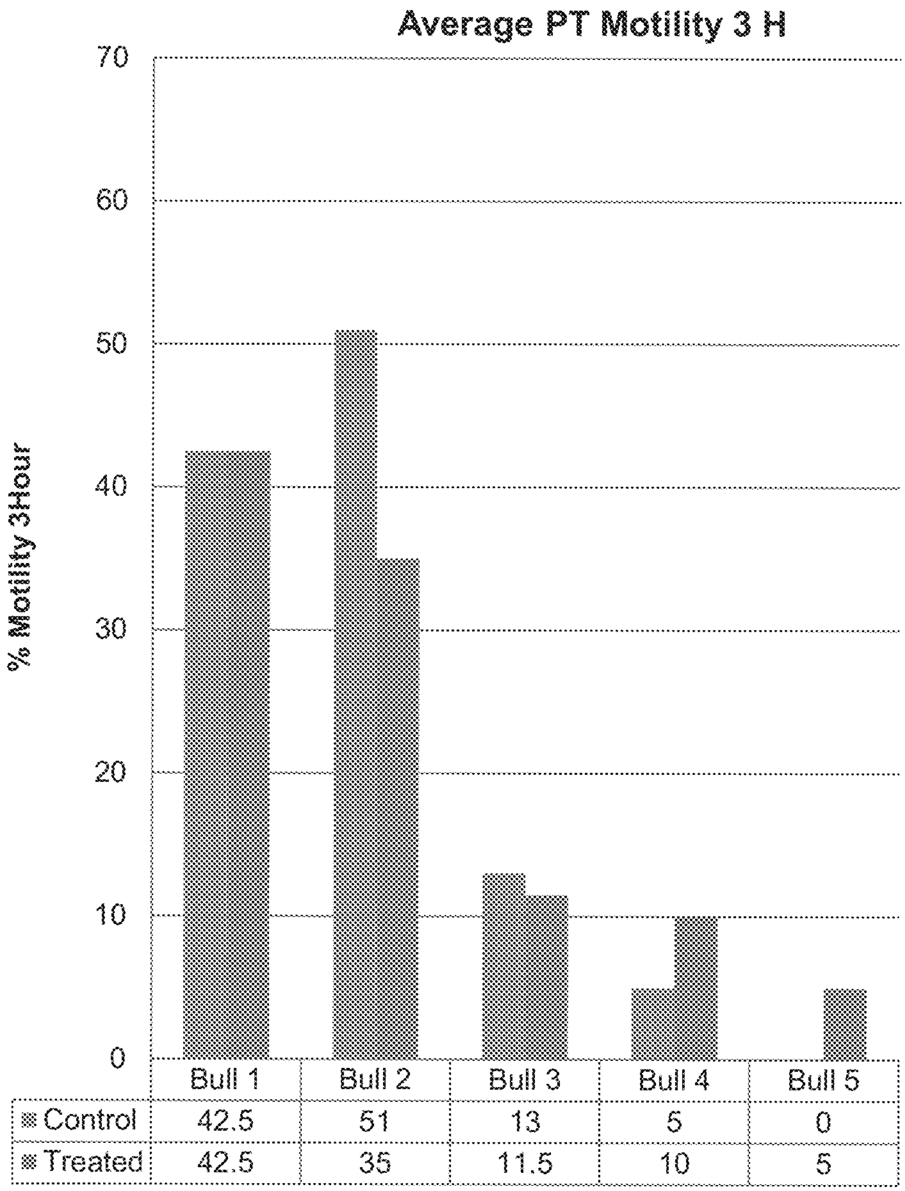
FIG. 12 shows 3-hour post-thaw motility of sperm treated with magnetic particles in Example 5.
Figure 13:
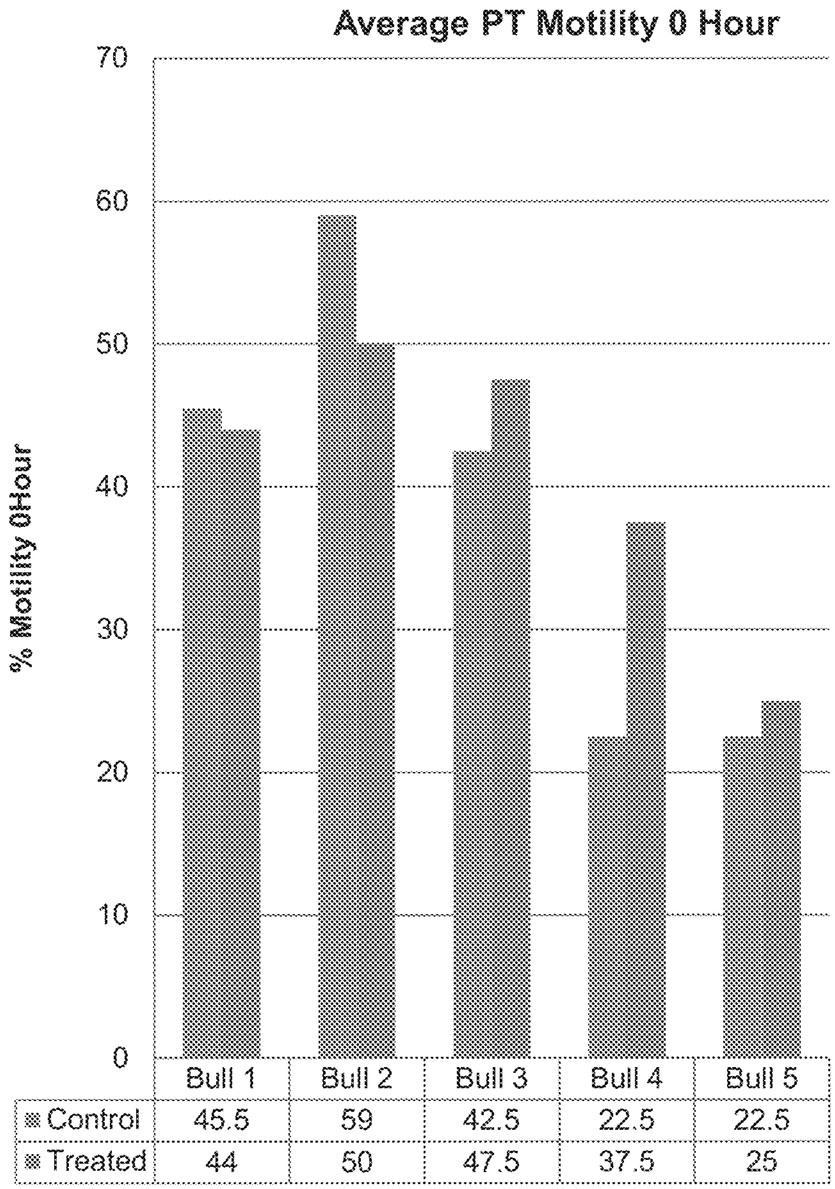
FIG. 13 shows 0-hour post-thaw motility of sperm treated with magnetic particles in Example 5.
Figure 14:
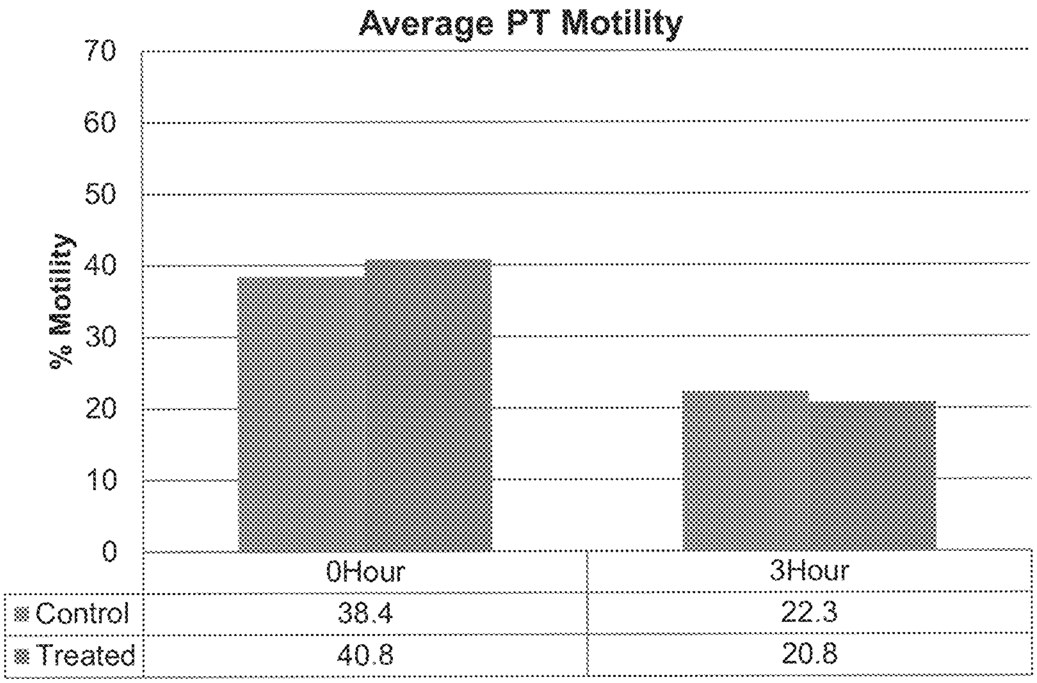
FIG. 14 shows the average 0- and 3-hour post-thaw motility of sperm treated with magnetic particles in Example 5.
Figure 15:
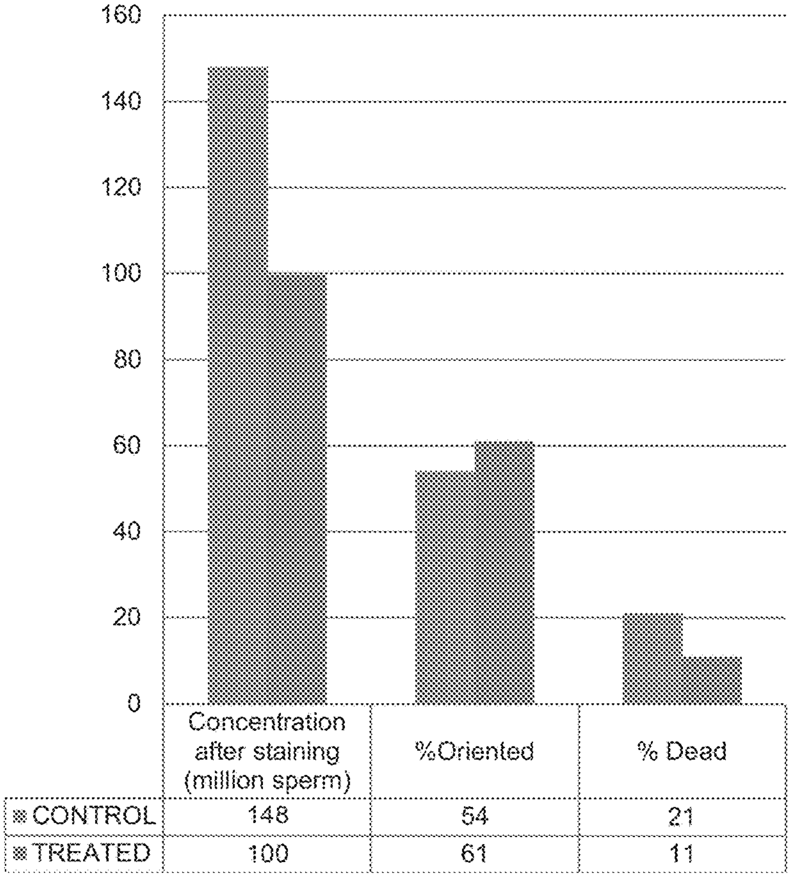
FIG. 15 shows various sort parameters and percentage of dead sperm removed by magnetic particles in Example 6.
Figure 16:
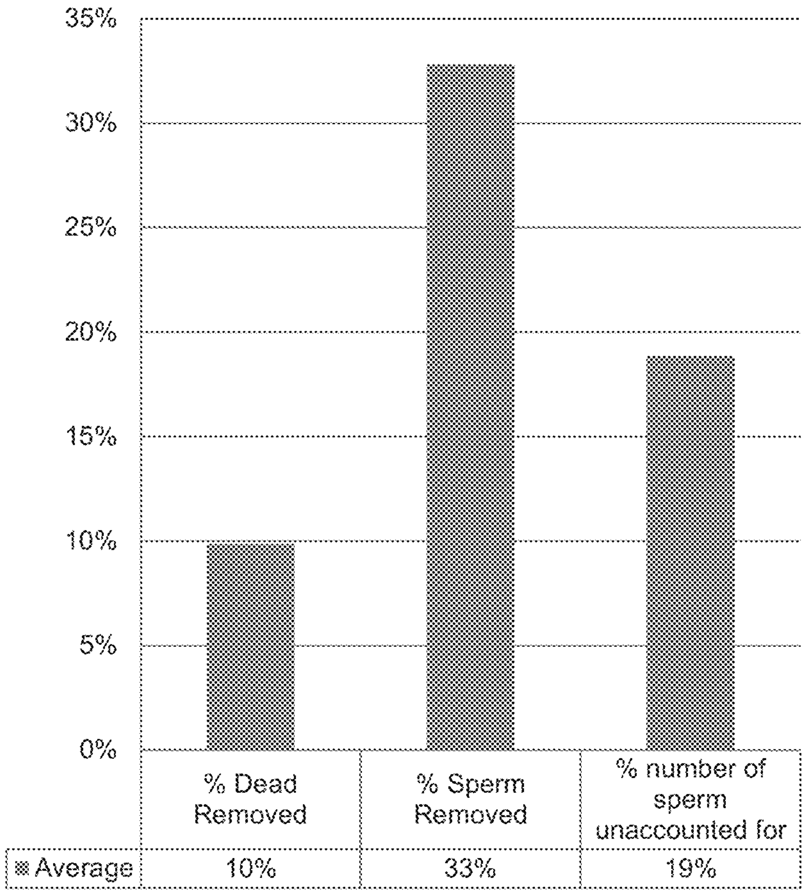
FIG. 16 shows the average percentage of dead sperm removed by magnetic particles in Example 6.
Figure 18:
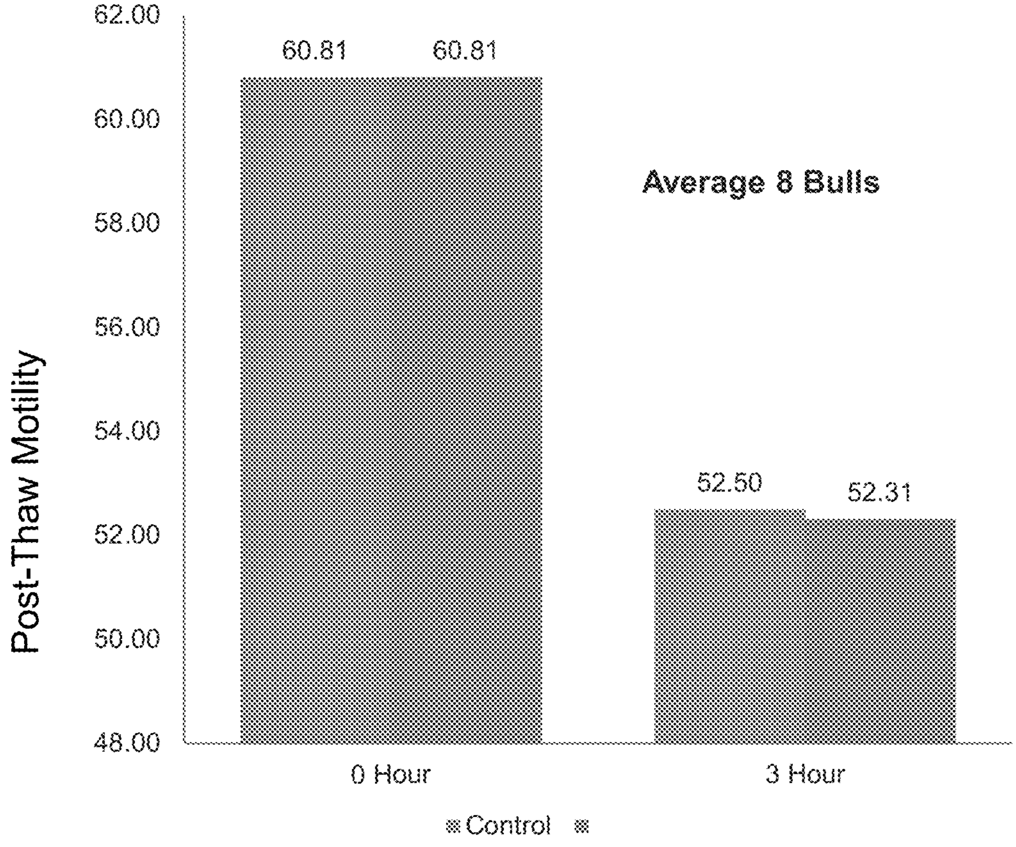
FIG. 18 shows the average 0- and 3-hour post-thaw motility of sperm treated with magnetic particles in Example 6.

1. Collect ejaculates.
2. Check volume, concentration, viability, motility, morphology and pH. Add antibiotics.
3. Standardize with TRIS media, pH 7.20, dilution 1:3.
4. Centrifuge and concentrate to 1700-1800 million sperm/mL.
5. Stain samples in modified TALP (20% Y6 with antioxidants), pH 7.4, at 160 million sperm per ml.
6. Add 2 mg of particles/320 million sperm in modified TALP, pH 7.4.
7. Incubate at 34° C. for 45 minutes.
8. Magnetically collect particles for 2 minutes.
9. Sort on flow cytometer. See results in FIG. 9.

Example 4 Removal of Dead Sperm in Modified TALP

Procedure

1. Collect ejaculates from 4 bulls. Check volume, concentration, viability, motility, morphology and pH. Add antibiotics.
2. Stain ejaculates with Hoechst 33342 in modified TALP (20% Y6 with antioxidants) (in 50 mL tubes), pH 7.4. The sperm concentration in modified TALP will be 160 million sperm per mL.
3. After 45 minutes of incubation at 34° C., divide samples in two:
   A 2 mL of treated sample (320 mill sperm total)
   B. 2 mL of control sample (320 mill sperm total)
4. Treated samples will be treated with 3.6 mg magnetic particles in 300 μL of modified TALP, pH 7.4.
5. Control samples will be treated with the same μL of modified TALP, pH 7.4 (without particles).
6. Incubate samples 20 minutes at room temperature.
7. Remove magnetic particles with magnet and place samples in 4 mL tubes.
8. Add 2 mL of red TALP to each sample.
9. Check sperm concentrations in the samples (NucleoCounter—final concentration of the control should be 80 million cells per mL).
10. Place samples on the flow cytometer and record parameters.

Treatment with magnetic particles in modified TALP, pH 7.4, at 320 million total sperm significantly removed dead cells in every bull (n=4). The average % of dead sperm removed according to the flow cytometer was 16%, taking samples from 20% to 4% dead. This increased sort speed from 3800 to 4900 at an event rate of 20,000 events per second (eps).

The average % sperm removed according to the NucleoCounter was 32%, 14% of cells were unaccounted for (when comparing NucleoCounter and flow cytometer data).

Example 5 Bulk-Sorting Sperm after Removal of Dead Sperm in Modified TALP

Procedure

1. Collect ejaculates from 5 bulls. Check volume, concentration, viability, motility, morphology and pH Add antibiotics.
2. Stain ejaculates with Hoechst 33342 in modified TALP (20% Y6 with antioxidants) (in 50 mL tubes), pH 7.4. The sperm concentration in modified TALP will be 160 million sperm per mL.
3. After 45 minutes of incubation at 34° C., divide samples in two:
   A 2 mL of treated sample (320 mill sperm total)
   B. 2 mL of control sample (320 mill sperm total)
4. Treated samples will be treated with 3.6 mg magnetic particles in 300 μL of modified TALP, pH 7.4.
5. Control samples will be treated with the same μL of modified TALP, pH 7.4 (without particles).
6. Incubate samples 20 minutes at room temperature.
7. Remove magnetic particles with magnet and place samples in 4 mL tubes.
8. Add 2 mL of red TALP to each sample.
9. Check sperm concentrations in the samples (NucleoCounter—final concentration of the control should be 160 million cells per mL).
10. Bulk sort 10 million cells per sample, check parameters, cryopreserve and perform post-thaw QC. See results in FIGS. 10-14.

Treatment with magnetic particles in modified TALP, pH 7.4, at 320 million total sperm increased sort rate from 2600 to 3200 at an event rate of 20,000 eps.

Example 6 Sex-Sorting Sperm after Removal of Dead Sperm in Modified TALP

Procedure

1. Collect ejaculates from 8 bulls. Check volume, concentration, viability, motility, morphology and pH. Add antibiotics.
2. Stain ejaculates with Hoechst 33342 in modified TALP (20% Y6 with antioxidants), pH 7.4

3. Place 1 mL of the stained sample in a 50 mL tube and treat with magnetic particles in modified TALP, pH 7.4.
4. Place 1 mL from the stained sample in a 4 mL tube and treat it with 250 μL of modified TALP, pH 7.4, without magnetic particles.
5. Incubate at room temperature for 20 min.
6. Remove magnetic particles with magnet and place treated sample in a 4 mL tube.
7. Check concentration of control and treated sample in NucleoCounter.
8. Add 1 mL of red TALP to each sample.
9. Sex-sort 10 million sperm for control, 10 million for treated sample, check parameters, cryopreserve and perform post-thaw QC. See results in FIGS. 15-18.

Example 7 Removal of Dead Sperm with Magnetic Particles and IVF

Procedure

Figure 20:
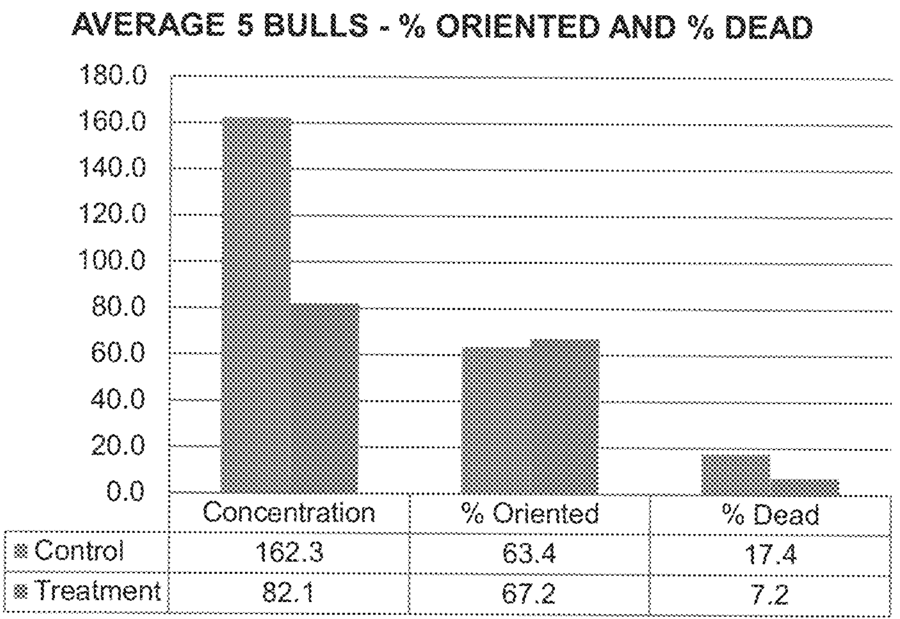
FIG. 20 shows the percentage of dead sperm removed by magnetic particles in Example 7.
Figure 21:
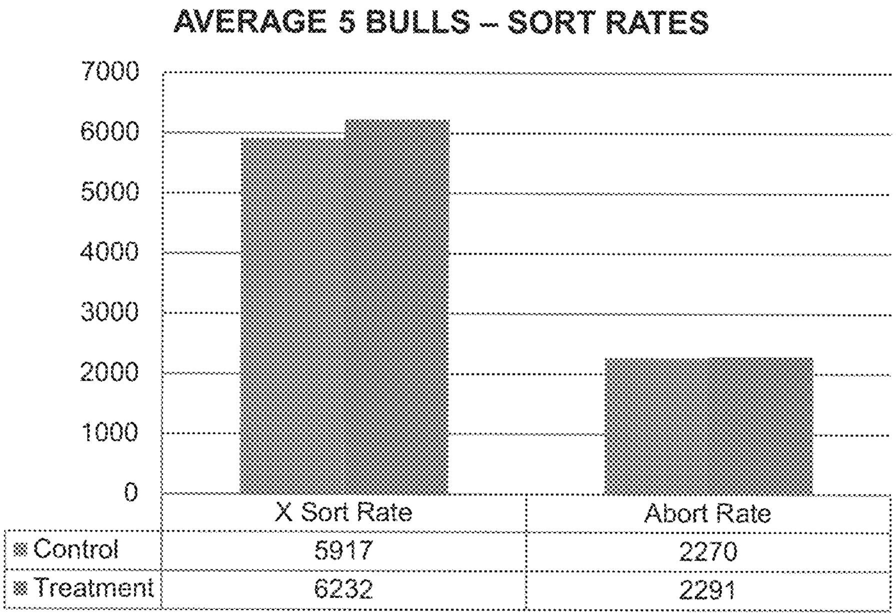
FIG. 21 shows the average sort and abort rates achieved in Example 7
Figure 22:
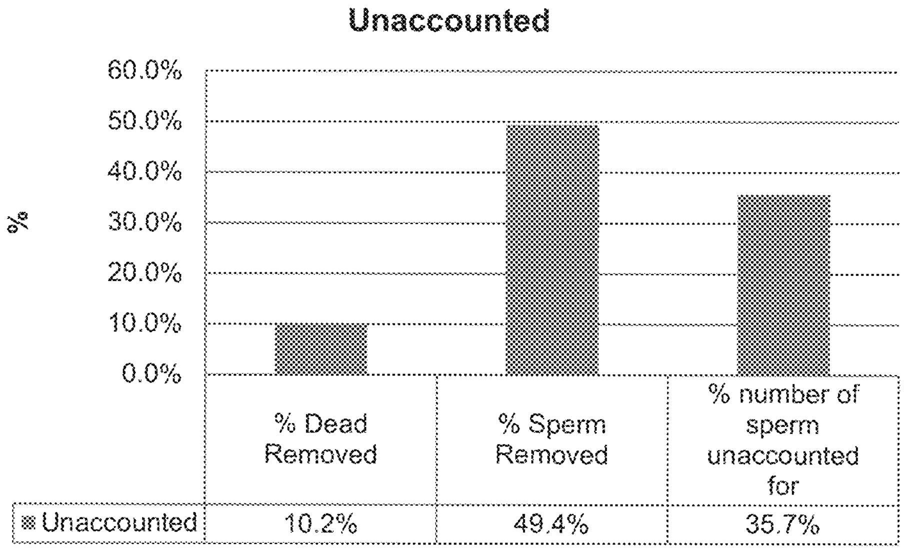
FIG. 22 shows the percentage of dead sperm removed by magnetic particles in Example 7.

1. Collect ejaculates from 8 bulls. Check volume, concentration, viability, motility, morphology and pH. Add antibiotics.
2. Staining volume in modified TALP (20% Y6 with antioxidants), pH 7.4 and Hoechst 33342 will be 4 mL. After 45 minutes of incubation at 34° C., samples divided in two: one will be used as control and the other will be treated with magnetic particles (each one will a total of 320 million sperm in 2 mL).
3. 3.6 mg of particles in water, collected with the magnet and re-suspended in 600 μL of modified TALP, pH 7.4, will be used for each sample at a concentration of 320 million sperm.
4. After adding the particles, the samples will be incubated 20 minutes at room temperature. Control samples will be kept in the same conditions but without the particles.
5. After treatment with magnetic particles, sperm concentrations will be determined in the treated and the control samples to quantify the % of total sperm (dead+unaccounted) removed by the particles and 2 mL of red TALP will be added for dead sperm quenching. Data from individual sorter histograms (using production sorters) will provide results for the amount of dead sperm (with and without treatment) as well as flow cytometer performance. See results in FIGS. 20-22.
6. Samples will be sex-sorted, frozen (5 straws per treatment for each bull) and sent to IVF trials. Standard post-thaw QC analysis will also be performed. See results in FIGS. 23 and 24.

Example 8 Production of Magnetic Particles

Procedure

Production of Cores:

1. Measure out $dH_2O$ and place in glass beaker (200 mL).
2. Weight out $FeCl_3 \cdot 6H_2O$ (11.68 grams).
3. Weigh out $FeCl_3 \cdot 4H_2O$ (4.30 grams)
4. Dissolve iron salts separately in cold water (use 1/3 of the total volume of $H_2O$ to dissolve each salt).
5. Mix both salts.
6. Use the remaining water to recuperate as much iron as possible from the beakers where the salts were dissolved.
7. Insert nitrogen source via tubing into the $H_2O$. Turn on nitrogen taking care not to exceed ~15 psi so as not to cause splashing.
8. Insert Mixer and start mixing the salts slowly.
9. Turn on the water kettle or water bath—Target temperature is 85° C.
10. Allow 15 minutes for appropriate mixing of the iron salts.
11. Add 25% $NH_3 \cdot H_2O$ slowly to the iron salt mixture (30 mLs).
12. Turn heat off and maintain mixing for 15 minutes.
13. Allow ferrofluid to cool to room temperature.
14. Place on glass beaker and place in magnetic holder. After ferrofluid has collected, decant off supernatant.
15. Repeat ferrofluid magnetic collection and wash with $dH_2O$—3 times.
16. After the final $dH_2O$ wash has been completed, wash ferrofluid with 0.02 M NaCl.
17. Once wash with 0.02 M NaCl is complete, magnetically collect ferrofluid again and resuspend in $dH_2O$.
18. Dehydrate 10 mL of particles, weight and calculate the amount of iron and the dilution in water to achieve a concentration of 33.0 mg/mL.

Silane Coating of Cores:

1. Ferrofluid (67.6 mgs) is added to 10% Carboxyethylsilanetriol sodium salt in water (35.5 mLs).
2. The pH is adjusted with >99% glacial acetic acid so that the pH reads 4.5.
3. The suspension is reacted at 70° C. for 2 hours with mixing (evaporate ~1/2 of the volume).
4. Allow coated particles to cool. Magnetically collect them in glass beaker and decant the supernatant.
5. Wash the particles with water and magnetically collect again—repeat 4 times.
6. After washes, the silane coated magnetic nanoparticles are resuspended in storage buffer (pH 7.4) at a known volume.
7. A sample is sent out for ICP analysis, and the resultant iron measurement dictates the resuspension volume of iron (usually 4 mg/mL).

Example 9

A batch of iron cores was produced (1 L, 58.4 grams of $FeCl_3 \cdot 6H_2O$ and 21.5 grams of $FeCl_2 \cdot 4H_2O$).

After the reaction of the iron salts (using 25% $NH_3 \cdot H_2O$ at 85° C.), the cores were washed in water and 0.02M NaCl in a volume of ~250 mL. Cores were kept in water at 4° C. Iron concentration in the ferrofluid measured 14.76 mg/mL of iron (53% yield).

Figure 25:
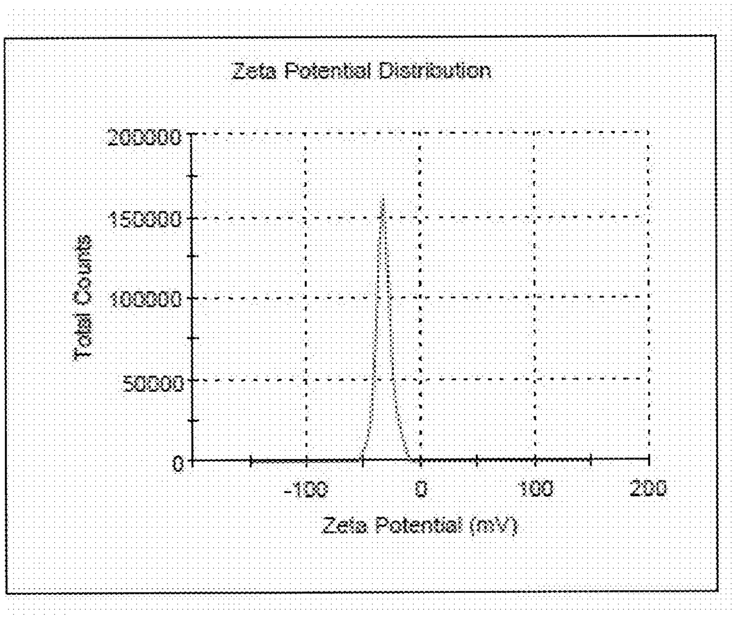
FIG. 25 shows Zeta potential distribution form magnetic particles produced according to Example 9.

67.6 mg of the ferrofluid was used for the production of coated magnetic particles. After the reaction with 10% carboxyethylsilanetriol sodium salt, the particles were washed in water and kept in bead storage buffer. Analyzed iron concentration using ICP measured 3.342 mg/ml. Zeta potential was measured to make sure that all the magnetic particles were properly coated. See FIG. 25.

Example 10 Titration of Magnetic Particles

Procedure

Figure 26:
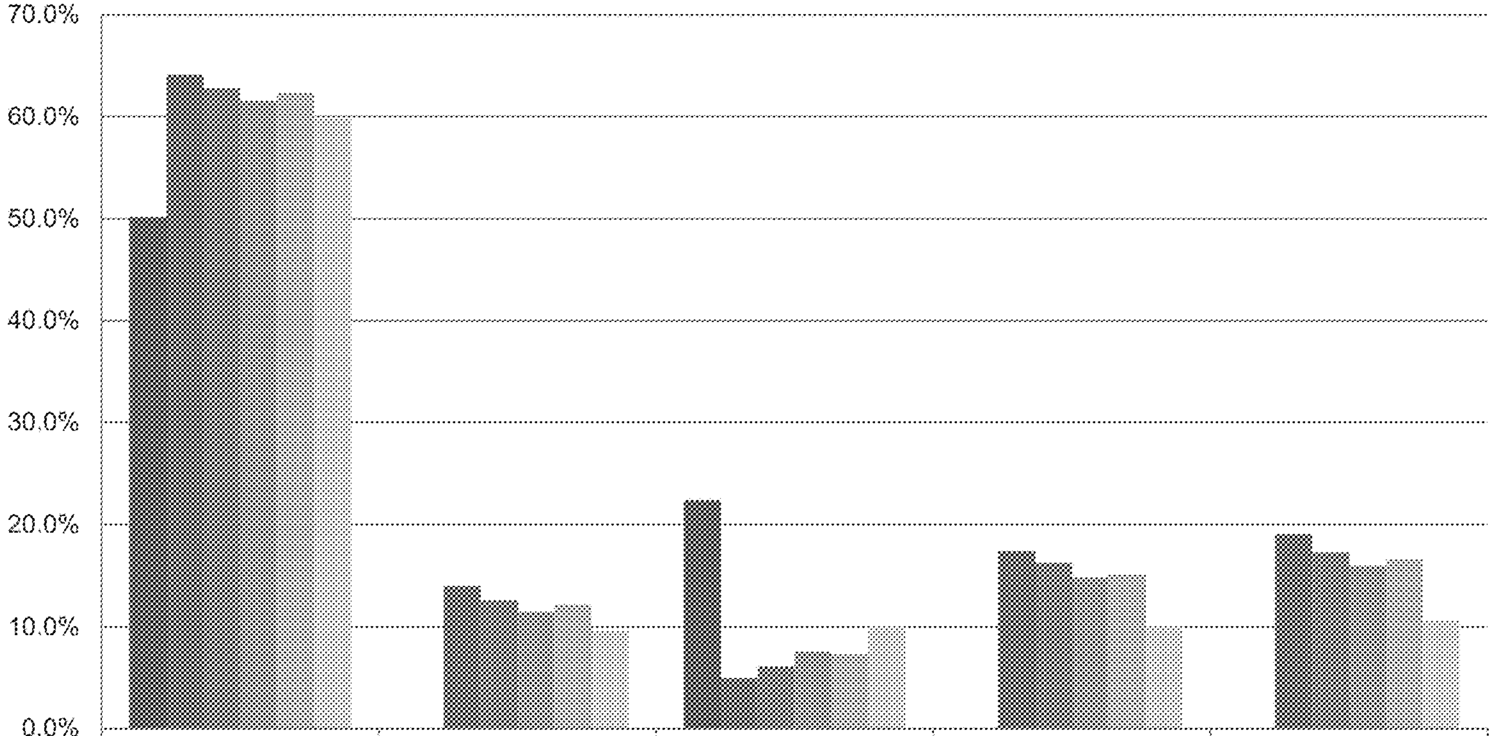
FIG. 26 shows the percentage of oriented sperm and the percentage of dead sperm in Example 10.
Figure 27:
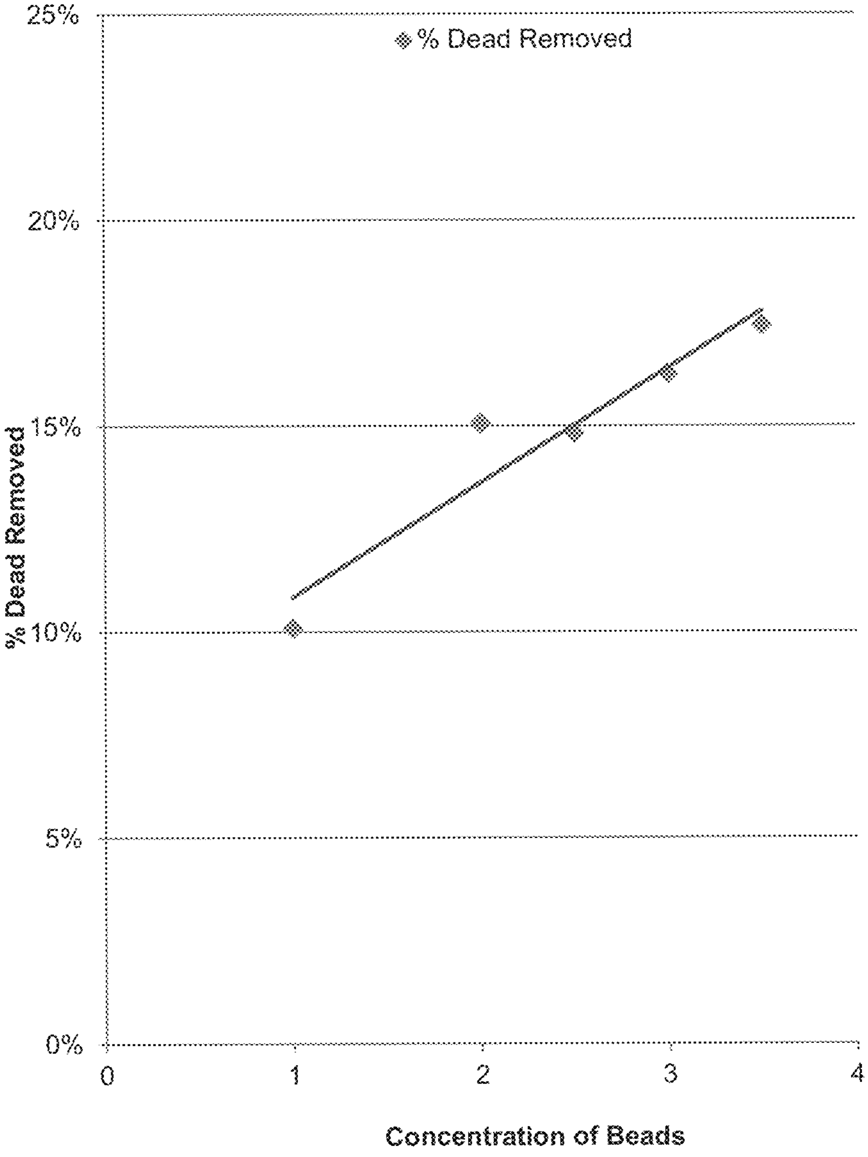
FIG. 27 shows the percentage of dead sperm removed by magnetic particles in Example 10.

1. Obtain ejaculates from 15 bulls.
2. Treat with TALP medium, pH 7.3 (1:3 dilution).
3. Stain samples in modified TALP (20% Y6 with antioxidants), pH 7.4, at a 160 million sperm per mL using Hoechst 33342.
4. Incubate 45 minutes.
5. Divide sample in 5 aliquots:
   Control
   3.5 mg of particles for every 320 million sperm 3.0 mg of particles (in 200 μL modified TALP, pH 7.4) for every 320 million sperm
2.5 mg of particles (in 200 μL modified TALP, pH 7.4) for every 320 million sperm
2.0 mg of particles (in 200 μL modified TALP, pH 7.4) for every 320 million sperm
1.0 mg of particles (in 200 μL modified TALP, pH 7.4) for every 320 million sperm 6. Add 300 μL of modified TALP, pH 7.4, to the control sample to keep the volumes equal.
7. Incubate samples for 20 minutes at room temperature.
8. Check concentration on NucleoCounter.
9. Place samples on the flow cytometer and record parameters. See results in FIGS. 26 and 27.

Example 11 Magnetic Particles Used in Live and Dead Sperm Mixed Samples

Procedure

1. Take a good quality neat ejaculate (total of 10 ejaculates).
2. Dilute ejaculate with 3× the amount of TALP medium, pH 7.3.
3. Centrifuge and resuspend to 1600 million sperm per mL.
4. Divide treated ejaculate in two parts: A and B.
5. Place part A in the cabinet and part B in the freezer for 1 hour.
6. Thaw part B.
7. Mix parts A and B in the following proportions: Only A (low % dead sample)
   3A:1B
   2A:2B
   1A:3B (very high % dead sample)
8. Stain each mix at 160 million sperm per mL in modified TALP (20% Y6 with antioxidants), pH 7.4 (2 mL samples) with Hoechst 33342. Incubate 45 minutes.
9. Add treatment with magnetic particles (2 mg per 320 million).
10. Incubate 20 minutes.
11. Magnetically collect particles. Place modified TALP, pH 7.4, with live sperm in a 4 mL tube.
12. Check concentration (NucleoCounter).
13. Place samples on the flow cytometer and record parameters. See results in FIG. 28.

Example 12 Magnetic Particles Used Before/During Staining in Modified TALP

Procedure

1. Take 6 neat ejaculates.
2. Dilute ejaculates with 3× the amount of TALP medium, pH 7.3.
3. Centrifuge and resuspend to 1800 million sperm per mL.
4. Stain in modified TALP (20% Y6 with antioxidants), pH 7.4, at 160 million sperm per mL (9 mL samples) in Hoechst 33342.
5. Divide 9 mL in 3 aliquotes of 3 mL:
   A Control
   B. Particles before incubation
   C. Particles during incubation
   D. Particles after incubation
6. Add magnetic particles (2 mg/360 million sperm) only to sample B.
7. Incubate for 25 minutes.
8. Take samples out of the water bath and add magnetic particles (2 mg/360 million sperm) only to sample C.
9. Place into incubator for another 20 minutes.
10. Take samples out of the water bath and add magnetic particles (2 mg/360 million sperm) only to sample D (incubate for 20 minutes).
11. Add the same volume of modified TALP, pH 7.4, without particles to sample A
12. Magnetically collect particles in samples B, C and D. Place modified TALP, pH 7.4, with live sperm in a 4 mL tube.
13. Check concentration (NucleoCounter).
14. Place samples on the flow cytometer and record parameters. See results in FIGS. 29 and 30.

Example 13 Magnetic Particles Used Before Staining in Modified TALP

Procedure

1. Get 5 fresh ejaculates.
2. Check volume, concentration, motility, morphology and pH. Add antibiotics.
3. Standardize with TALP medium, pH 7.2 (dilution 1:3).
4. Centrifuge and concentrate to 1700-1800 million sperm/mL.
5. Dilute each sample to 160 million sperm per mL in a 4 mL final volume in modified TALP (20% Y6 with antioxidants), pH 7.4.
6. Divide each sample in 2: Control and Treatment.
7. Add magnetic particles to the "Treatment" sample (2 mg/320 million sperm) and equal volume of modified TALP to the "Control" sample.
8. Incubate for 10 minutes.
9. Add Hoechst 33342 stain to all the samples (17 μL per 320 million sperm).
10. Incubate 45 minutes at 34° C.
11. Magnetically collect the particles in the treated sample.
12. Place samples on the flow cytometer and record parameters. See results in FIGS. 31 and 32.

Example 14 Magnetic Particles Recovery after Second Wash

Procedure

1. Get 5 fresh ejaculates.
2. Treat with TALP medium, pH 7.3 (1:3 dilution).
3. Stain a 4 mL sample in modified TALP (20% Y6 with antioxidants), pH 7.4, at a 160 million sperm per mL.
4. Divide sample in 2 aliquots (2 mL each): Control and Treated
5. Add magnetic particles (2 mg/320 million sperm) to Treated sample and equivalent volume of modified TALP, pH 7.4, to Control sample.
6. Incubate 45 minutes. Collect magnetic particles.
7. Check concentration.
8. Place samples on the flow cytometer and record parameters.
9. Analyze viability on control sample, treated sample and magnetic particles (resuspended in 300 μL of modified TALP, pH 7.4): Take 50 μL each sample and dilute into 1 mL of modified TALP, pH 7.4. Add 15 μL of SYBRSYBR®-14 and incubate 10 minutes at 34° C. Add 5 μL of PI. Check viability on analyzer. See results in FIGS. 33 and 34.

Example 15 IVF

Procedure

1. Get 5 fresh ejaculates.

2. Check volume, concentration, motility, morphology and pH. Add antibiotics.
3. Standardize with TALP medium, pH 7.2 (dilution 1:3).
4. Centrifuge and concentrate to 1700-1800 million sperm/mL.
5. Stain a 6 mL sample for each bull in modified TALP (20% Y6 with antioxidants), pH 7.4, at 160 million sperm per mL with Hoechst 33342.
6. Divide each sample in 2 tubes (4 mL tubes filled with 3 mL of sample):
   Control
   Treated
7. Treat sample B with 0.387 μL of pre-washed particles (=2 mg/320 million cells) and sample A with 0.387 μL of modified TALP, pH 7.4.
8. Incubate at 34° C. for ~45 minutes.
9. Collect particles.
10. Check concentration on NucleoCounter.
11. Sort 15 million cells on flow cytometer and record parameters. See result for 2 sets in FIGS. 35, 36 and 38-40.
12. Place in the cold-room for 90 minutes and cryopreserve 4-5 straws (2.1 million cells per ¼ cc straw) in TRIS AB.
13. Check post-thaw QC: Motility (0 and 3 hour), SYBR®-14/PI Viability and Purity. See results for 2 sets in FIGS. 37 and 41.
14. Conduct IVF trials. See results in FIG. 42.

Example 16 Field Trial

Ejaculates from 5 bulls were divided and treated with magnetic particles during staining with Hoechst 33342 and then sex-sorted on a flow cytometer after removal of the magnetic particles. 637 heifers and 731 cows were then inseminated with either control samples (sex sorted, no treatment with magnetic particles) or samples treated with magnetic particles. The pregnancy rate for the control group was 44.7% and for the treatment group was 43.9%. The conception rates for control cows was 32.94% (SE=3.7%), for control heifers 50.93% (SE=2.68%), for treatment cows 39.30% (SE=2.42%) and for treatment heifers 49.17% (SE=3.24%).

As can be easily understood from the foregoing, the basic concepts of the present invention may be embodied in a variety of ways. The invention involves numerous and varied embodiments using sex sorted sperm to increase the genetic progress of a line, including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

I claim:

1. A method of processing sperm cells comprising the steps of:
adding magnetic particles to a composition comprising sperm cells, the magnetic particles comprising magnetic particles 300 nm in size and a negative zeta potential charge, the magnetic particles forming complexes with the sperm cells solely through an electrical charge interaction; and
applying a magnetic field to the complexes.

2. The method of claim 1, the magnetic particles comprising an outer layer comprising a chargeable, or charged, moiety.

3. The method of claim 2, the chargeable, or charged, moiety comprising a metal, an oxide, a carboxylate, an amine, an amide, a carbamide, a sulfate, a sulfonate, a sulfite, a phosphonate, a phosphate, a halide or a hydroxide.

4. The method of claim 1, wherein the composition has a pH of 6.5 to 8.0.

5. The method of claim 1, wherein the composition comprises a buffer.

6. The method of claim 1, wherein the composition comprises sperm cells at a concentration of $120\times10^6$ cells/ml to $500\times10^6$ cells/ml.

7. The method of claim 1, wherein the magnetic particles are non-toxic to the sperm cells.

* * * * *